(12) United States Patent
Spence

(10) Patent No.: US 12,336,727 B2
(45) Date of Patent: *Jun. 24, 2025

(54) DEVICES, SYSTEMS AND METHODS TO REMOVE BLOOD CLOTS

(71) Applicant: Ischemicure Ltd., Louisville, KY (US)

(72) Inventor: Paul A. Spence, Louisville, KY (US)

(73) Assignee: Ischemicure Ltd., Louisville, KY (US)

(*) Notice: Subject to any disclaimer, the term of this patent is extended or adjusted under 35 U.S.C. 154(b) by 0 days.

This patent is subject to a terminal disclaimer.

(21) Appl. No.: 18/740,004

(22) Filed: Jun. 11, 2024

(65) Prior Publication Data

US 2024/0366246 A1 Nov. 7, 2024

Related U.S. Application Data

(63) Continuation of application No. 18/475,929, filed on Sep. 27, 2023, which is a continuation of application (Continued)

(51) Int. Cl.
*A61B 17/22* (2006.01)
*A61B 17/12* (2006.01)
(Continued)

(52) U.S. Cl.
CPC ........ *A61B 17/221* (2013.01); *A61B 17/1204* (2013.01); *A61B 17/12109* (2013.01); *A61B 17/22* (2013.01); *A61B 17/32037* (2013.01); *A61F 2/013* (2013.01); *A61F 2/844* (2013.01); *A61F 2/958* (2013.01); *A61M 1/75* (2021.05);
(Continued)

(58) Field of Classification Search
CPC .............. A61B 17/22; A61B 17/22031; A61B 2017/00323; A61B 2017/00867; A61B 2017/22079; A61B 2017/22081; A61B 2017/22051; A61B 2017/22048; A61F 2/844; A61F 2/958; A61F 2/013
See application file for complete search history.

(56) References Cited

U.S. PATENT DOCUMENTS

| 4,445,892 A | 5/1984 | Hussein et al. |
| 5,419,774 A | 5/1995 | Willard et al. |

(Continued)

FOREIGN PATENT DOCUMENTS

| CN | 1501825 A | 6/2004 |
| CN | 108113734 A | 6/2018 |

(Continued)

OTHER PUBLICATIONS

Examiner Interview Summary issued by The United States Patent and Trademark Office for U.S. Appl. No. 16/637,046, dated Apr. 6, 2021, 4 pages.

(Continued)

*Primary Examiner* — Katherine M Rodjom

(57) ABSTRACT

Systems, devices and methods for removing a blood clot (10) from a blood vessel (12). Various uses of suction pressure and positive pressure, proximal and/or distal to the blood clot (10) assist with clot dislodgement and removal. The pressure(s) may be constant and/or cycled/pulsed to assist with clot dislodgement and/or removal. Various further devices assist with separating the clot (10) from the vessel (12).

28 Claims, 58 Drawing Sheets

Related U.S. Application Data

No. 17/379,566, filed on Jul. 19, 2021, now Pat. No. 11,793,532, which is a continuation of application No. 16/637,046, filed as application No. PCT/US2019/015220 on Jan. 25, 2019, now Pat. No. 11,065,017.

(60) Provisional application No. 62/775,510, filed on Dec. 5, 2018, provisional application No. 62/654,693, filed on Apr. 9, 2018, provisional application No. 62/621,776, filed on Jan. 25, 2018.

(51) Int. Cl.
| | | |
|---|---|---|
| *A61B 17/221* | (2006.01) | |
| *A61B 17/3203* | (2006.01) | |
| *A61F 2/01* | (2006.01) | |
| *A61F 2/844* | (2013.01) | |
| *A61F 2/958* | (2013.01) | |
| *A61M 1/00* | (2006.01) | |
| *A61B 6/00* | (2006.01) | |
| *A61B 6/50* | (2024.01) | |
| *A61B 17/00* | (2006.01) | |
| *A61M 25/10* | (2013.01) | |
| *A61M 39/00* | (2006.01) | |

(52) U.S. Cl.
CPC ............... *A61M 1/79* (2021.05); *A61M 1/85* (2021.05); *A61M 1/87* (2021.05); *A61B 6/481* (2013.01); *A61B 6/501* (2013.01); *A61B 6/504* (2013.01); *A61B 2017/00323* (2013.01); *A61B 2017/00867* (2013.01); *A61B 17/12168* (2013.01); *A61B 2017/22079* (2013.01); *A61M 2025/1052* (2013.01); *A61M 2039/0009* (2013.01)

(56) References Cited

U.S. PATENT DOCUMENTS

| | | | |
|---|---|---|---|
| 5,487,649 A | 1/1996 | Dorsey, III et al. | |
| 5,628,761 A | 5/1997 | Rizik | |
| 5,728,123 A | 3/1998 | Lemelson et al. | |
| 5,730,717 A | 3/1998 | Gelbfish | |
| 5,772,674 A | 6/1998 | Nakhjavan | |
| 5,925,016 A | 7/1999 | Chornenky et al. | |
| 5,989,271 A | 11/1999 | Bonnette et al. | |
| 6,022,336 A | 2/2000 | Zadno-Azizi et al. | |
| 6,135,991 A | 10/2000 | Muni et al. | |
| 6,416,523 B1 | 7/2002 | Lafontaine | |
| 6,485,500 B1 * | 11/2002 | Kokish .................. A61F 2/013 604/101.03 |
| 6,575,932 B1 | 6/2003 | O'Brien et al. | |
| 6,685,722 B1 | 2/2004 | Rosenbluth et al. | |
| 6,695,858 B1 | 2/2004 | Dubrul et al. | |
| 7,220,269 B1 | 5/2007 | Ansel et al. | |
| 7,731,683 B2 | 6/2010 | Jang et al. | |
| 8,057,497 B1 | 11/2011 | Raju et al. | |
| 8,075,510 B2 | 12/2011 | Aklog et al. | |
| 8,152,782 B2 | 4/2012 | Jang et al. | |
| 8,444,661 B2 | 5/2013 | Nair et al. | |
| 8,858,497 B2 | 10/2014 | Di Palma et al. | |
| 9,149,609 B2 | 10/2015 | Ansel et al. | |
| 9,586,023 B2 | 3/2017 | Bonnette et al. | |
| 9,692,557 B2 | 6/2017 | Murphy | |
| 10,342,573 B1 * | 7/2019 | Walzman ............... A61L 29/145 |
| 11,065,017 B2 | 7/2021 | Spence | |
| 11,793,532 B2 | 10/2023 | Spence | |
| 11,950,795 B1 | 4/2024 | Spence | |
| 2002/0188276 A1 | 12/2002 | Evans et al. | |
| 2003/0050600 A1 | 3/2003 | Ressemann et al. | |
| 2004/0015150 A1 | 1/2004 | Zadno-Azizi | |
| 2004/0260333 A1 | 12/2004 | Dubrul et al. | |
| 2005/0096723 A1 | 5/2005 | Nash et al. | |
| 2006/0052797 A1 | 3/2006 | Kanamaru | |
| 2006/0064074 A1 | 3/2006 | Mallaby | |
| 2006/0200191 A1 | 9/2006 | Zadno-Azizi | |
| 2007/0287956 A1 | 12/2007 | Tal | |
| 2010/0145371 A1 | 6/2010 | Rosenbluth et al. | |
| 2011/0060212 A1 | 3/2011 | Slee et al. | |
| 2011/0213392 A1 | 9/2011 | Aklog et al. | |
| 2014/0257245 A1 | 9/2014 | Rosenbluth et al. | |
| 2014/0276602 A1 | 9/2014 | Bonnette et al. | |
| 2015/0250577 A1 | 9/2015 | Hall | |
| 2017/0056061 A1 * | 3/2017 | Ogle ............... A61B 17/320725 |
| 2017/0105743 A1 | 4/2017 | Vale et al. | |
| 2017/0189654 A1 | 7/2017 | Schwartz et al. | |
| 2017/0215890 A1 | 8/2017 | Turjman et al. | |
| 2017/0367718 A1 | 12/2017 | Georgilis et al. | |
| 2018/0064453 A1 * | 3/2018 | Garrison ........... A61M 25/0067 |
| 2018/0098778 A1 | 4/2018 | Ogle | |
| 2021/0068852 A1 | 3/2021 | Spence | |
| 2021/0386439 A1 | 12/2021 | Spence | |
| 2024/0130749 A1 | 4/2024 | Spence | |

FOREIGN PATENT DOCUMENTS

| | | | |
|---|---|---|---|
| FR | 2827152 A1 | 1/2003 | |
| WO | WO-2009132858 A2 | 11/2009 | |
| WO | WO-2014022145 A1 | 2/2014 | |
| WO | WO-2018019829 A1 | 2/2018 | |
| WO | WO-2019147985 A1 | 8/2019 | |
| WO | WO-2021097215 A1 | 5/2021 | |
| WO | WO-2021108371 A1 | 6/2021 | |

OTHER PUBLICATIONS

Extended European Search Report for Application No. 19744311.2, mailed on Aug. 25, 2021, 10 pages.

International Search Report and Written Opinion issued by the International Searching Authority for Application No. PCT/US2020/060426, dated Mar. 18, 2021, 15 pages.

International Search Report and Written Opinion issued by the International Searching Authority for Application No. PCT/US2020/061958, dated Apr. 2, 2021, 12 pages.

International Search Report and Written Opinion issued by the International Searching Authority for Application No. PCT/US2019/015220, dated May 30, 2019, 20 pages.

Non Final Office Action for U.S. Appl. No. 17/379,566 dated Jan. 20, 2023, 13 pages.

Non-Final Office Action issued by The United States Patent and Trademark Office for U.S. Appl. No. 16/637,046, dated Jan. 26, 2021, 26 pages.

Non-Final Office Action mailed on Dec. 9, 2021 for U.S. Appl. No. 17/379,566, 13 pages.

Office Action and Search report for Chinese Application No. CN201980010325.9 dated Nov. 30, 2023, 16 pages.

Office Action for European Application No. 19744311.2 dated Feb. 3, 2023, 6 pages.

Office Action for Japanese Application No. JP20210005733 dated Dec. 19, 2022, 12 pages.

Office Action for U.S. Appl. No. 17/379,566 dated Jun. 6, 2022, 26 pages.

Office Action issued by the Japanese Patent Office for Application No. JP2021-5733, dated Jul. 10, 2023, 9 pages including English translation.

\* cited by examiner

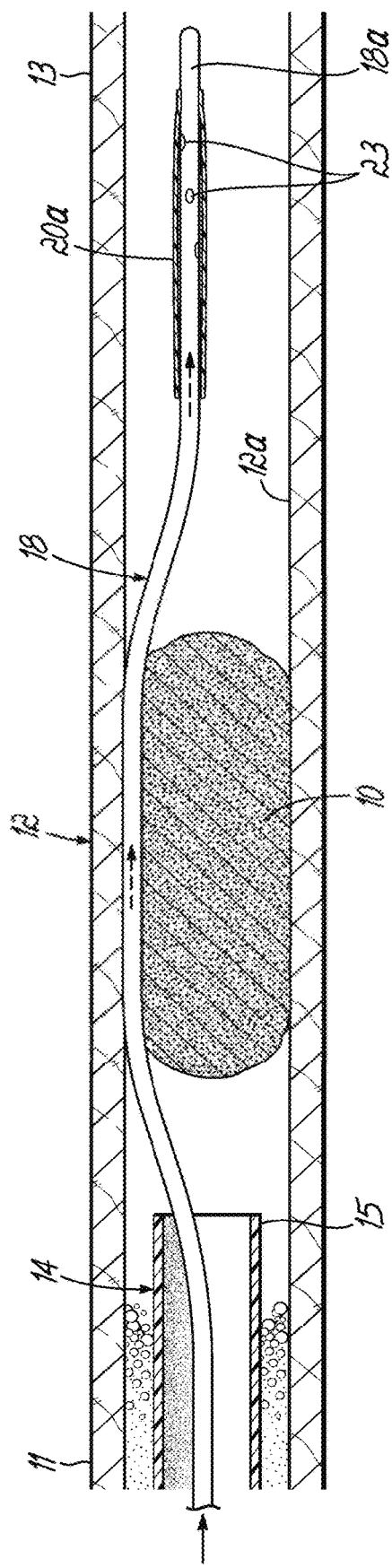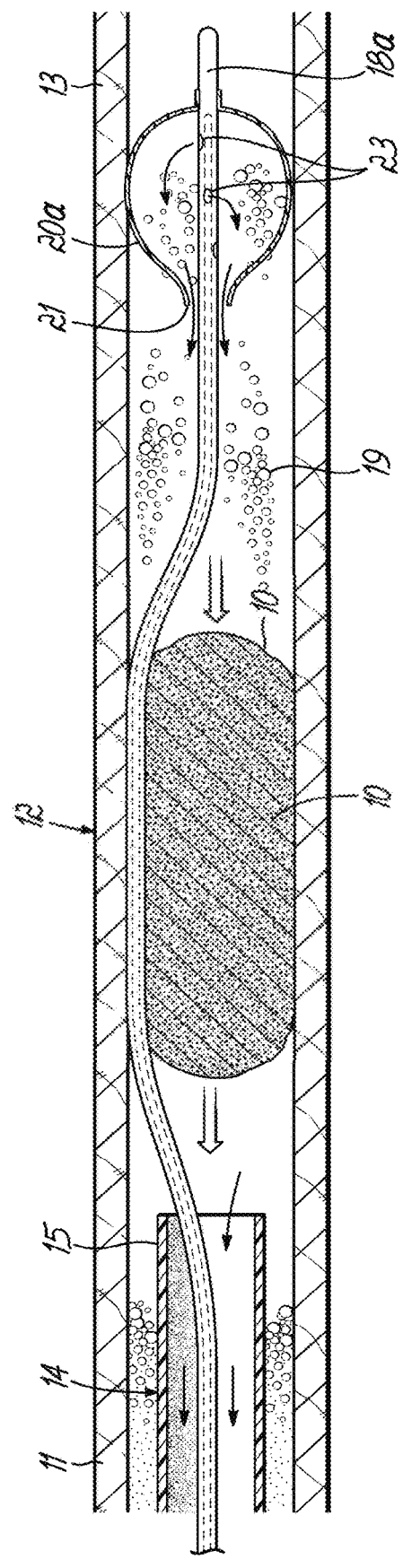

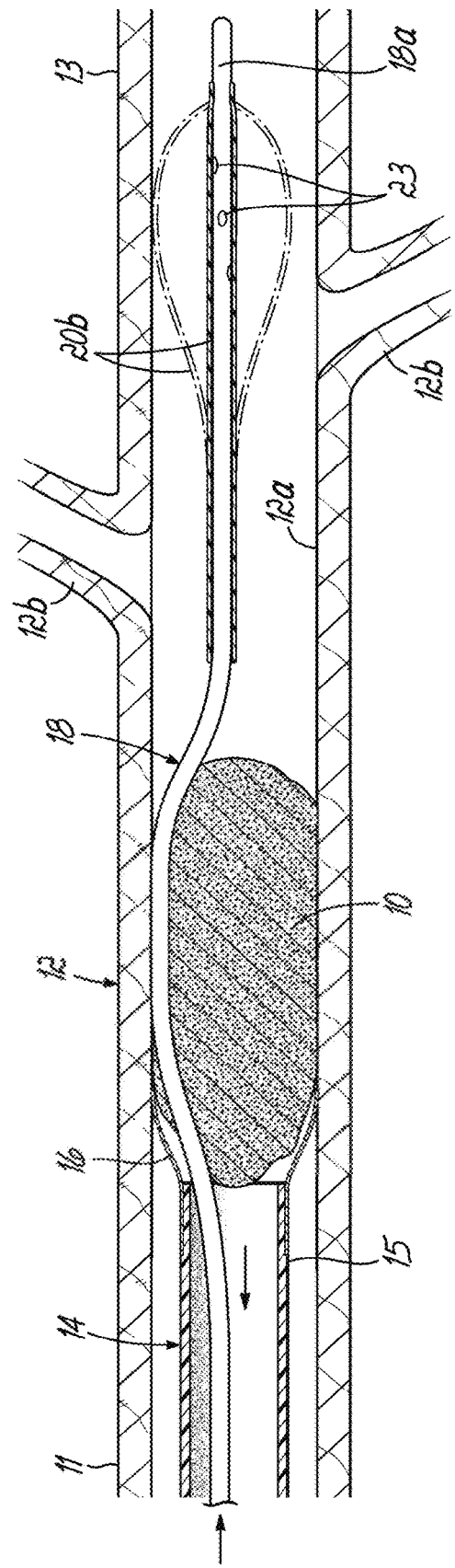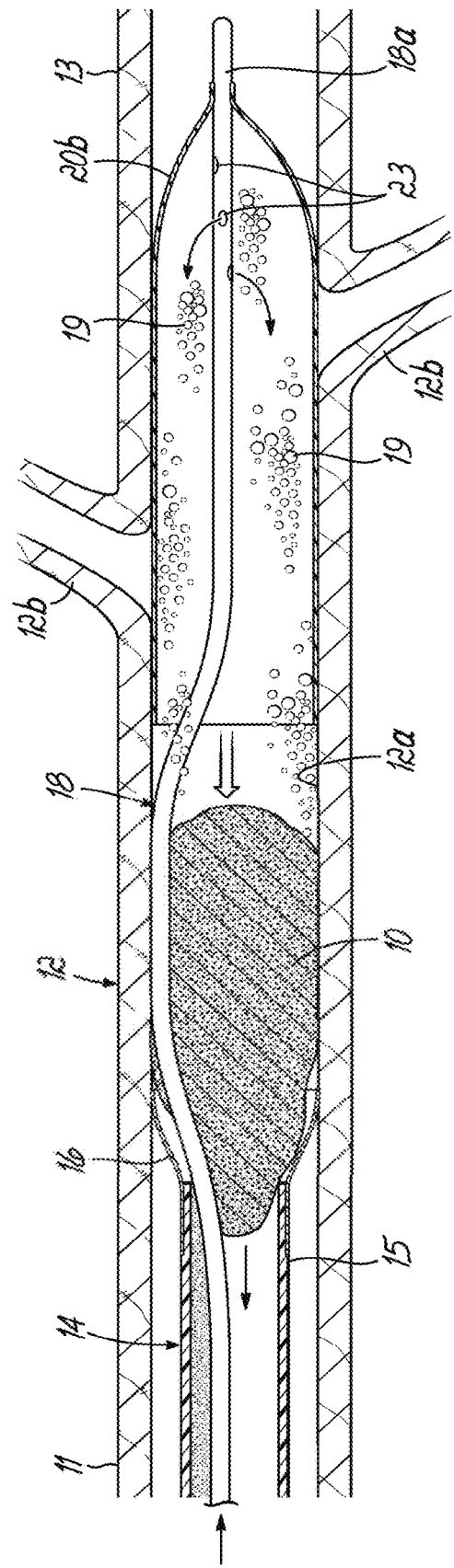
FIG. 3A
FIG. 3B

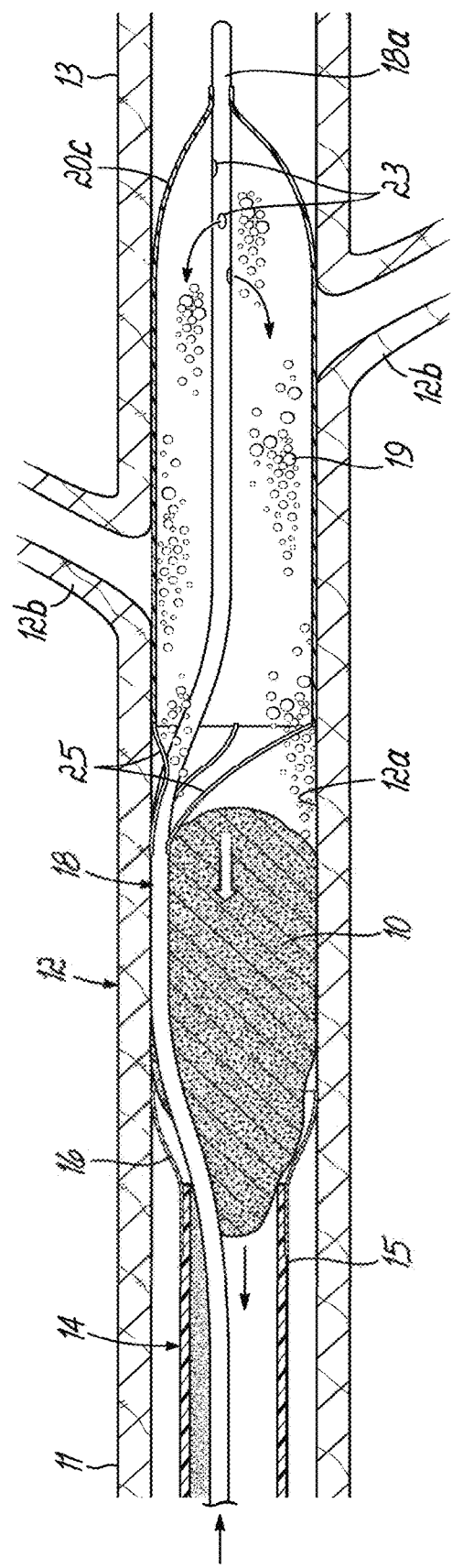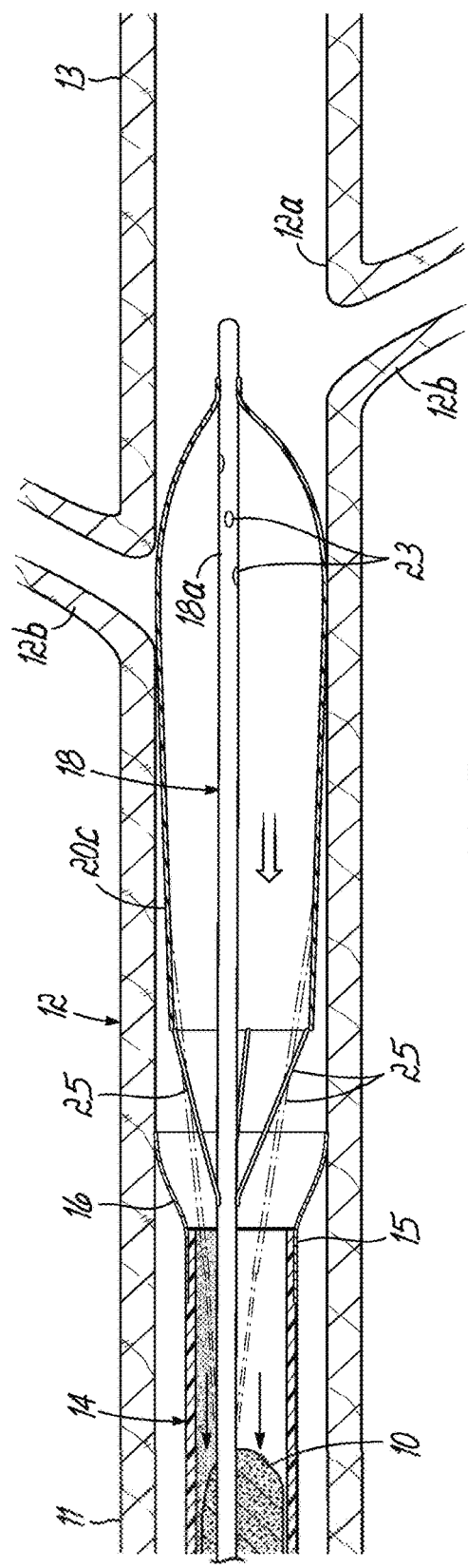
FIG. 3E
FIG. 3F

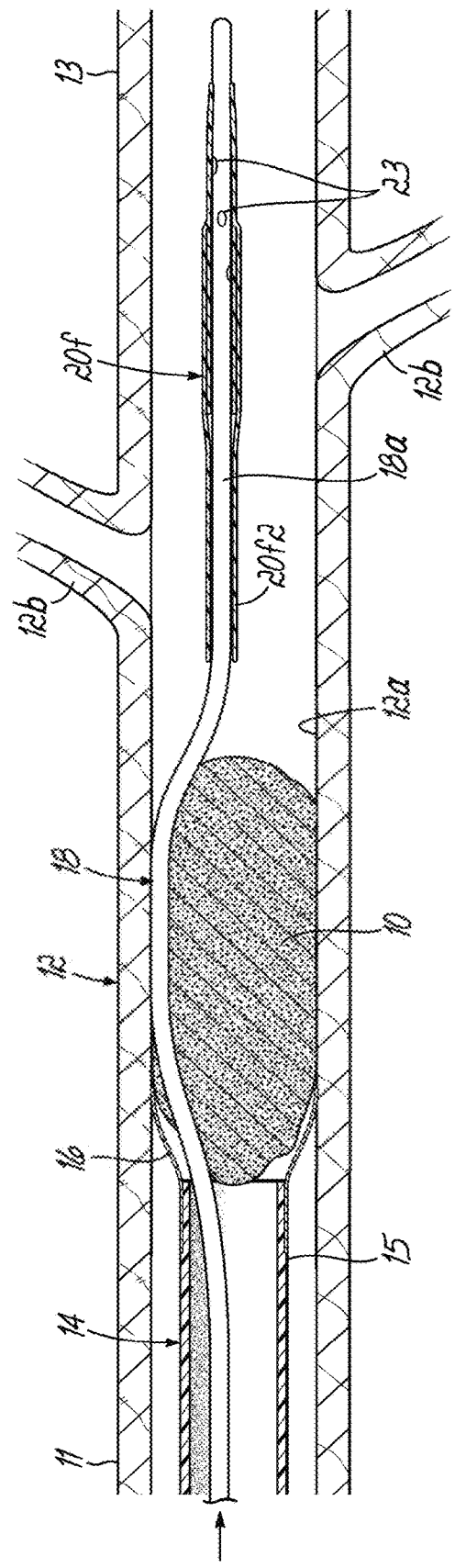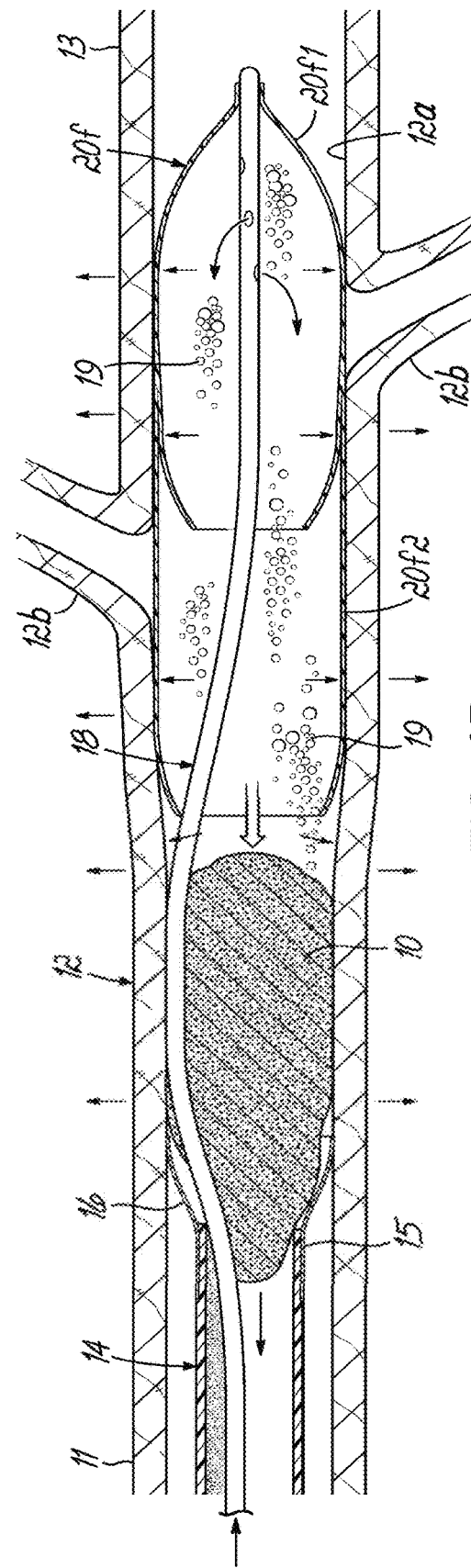
FIG. 4A
FIG. 4B

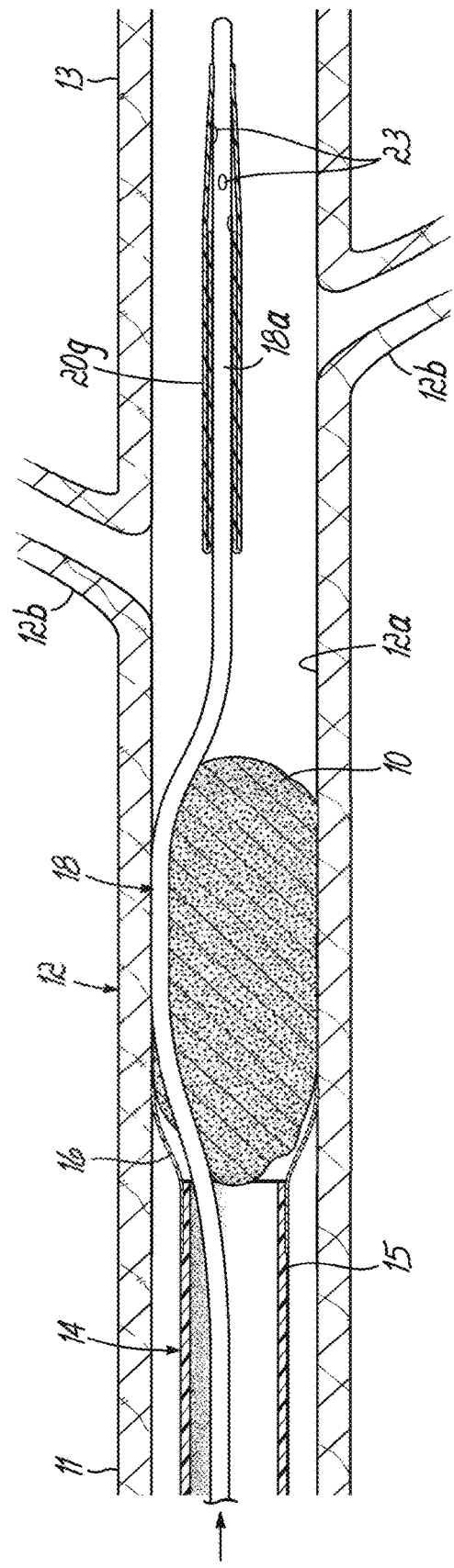
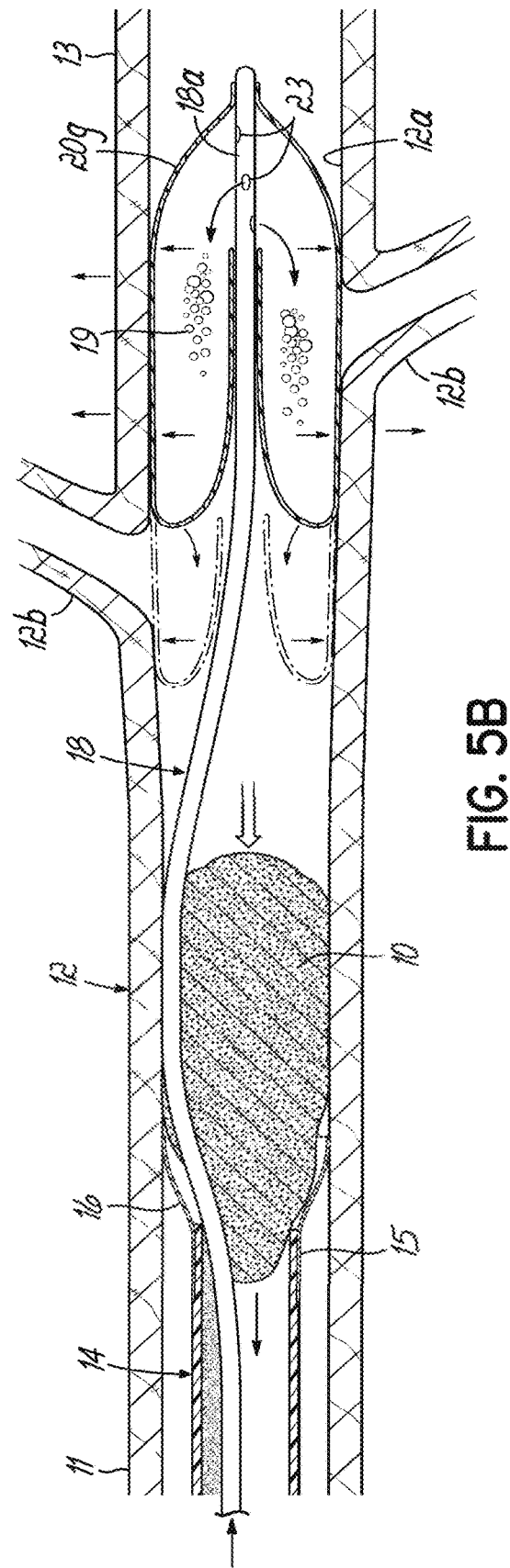
FIG. 5A
FIG. 5B

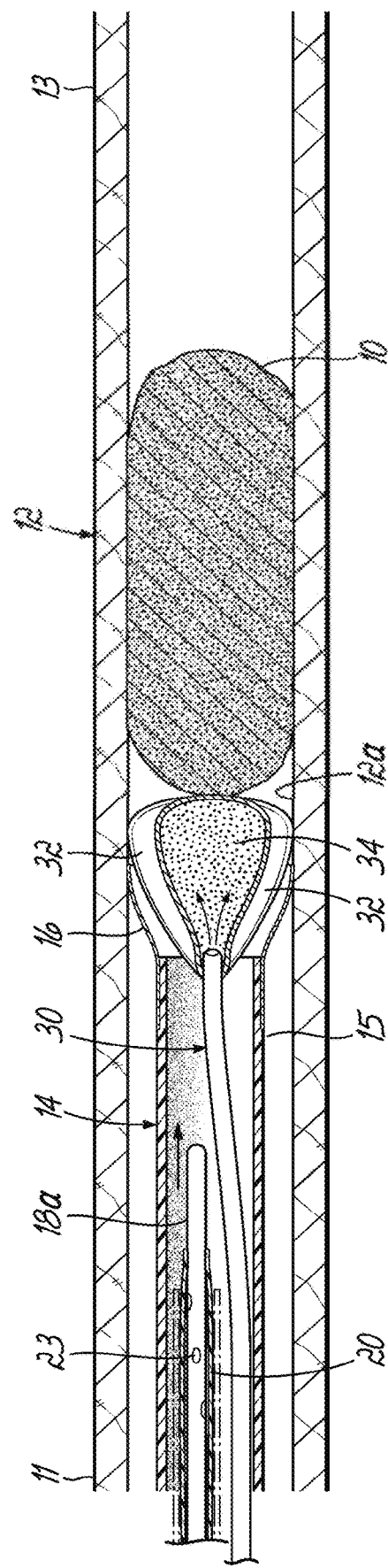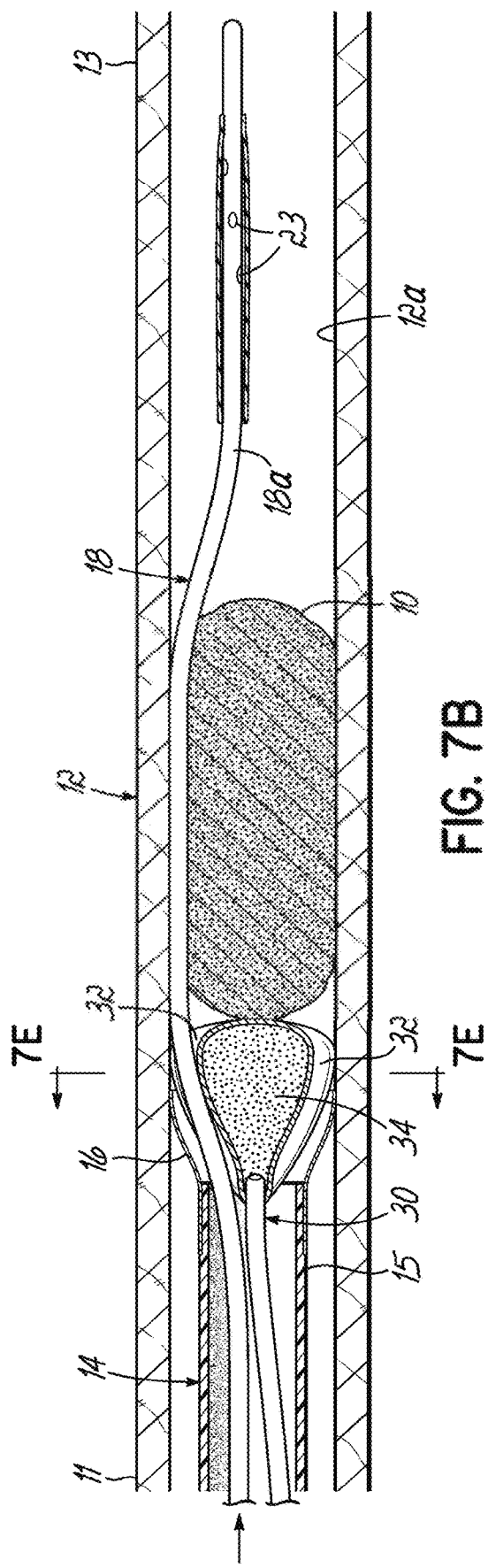
FIG. 7A
FIG. 7B

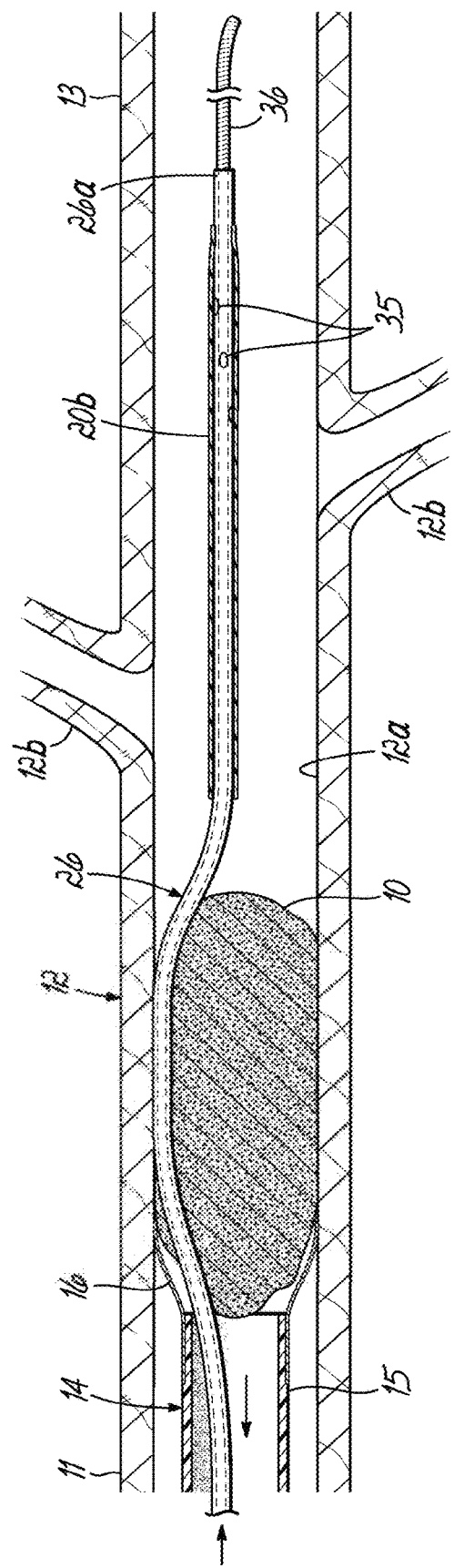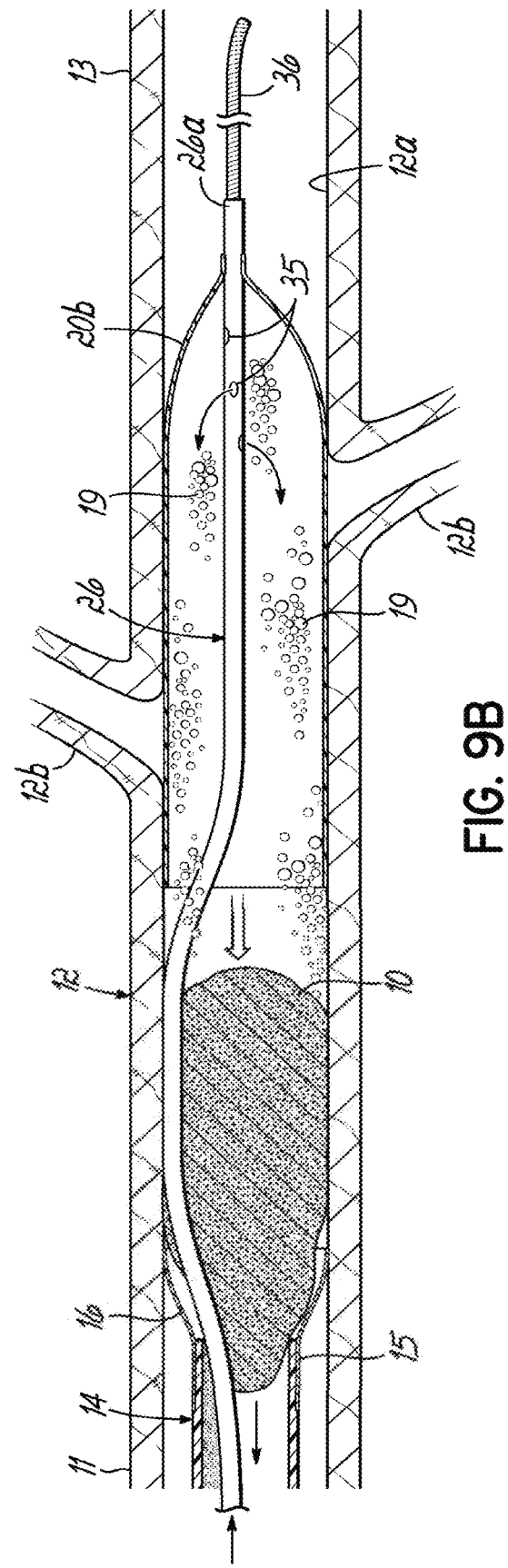

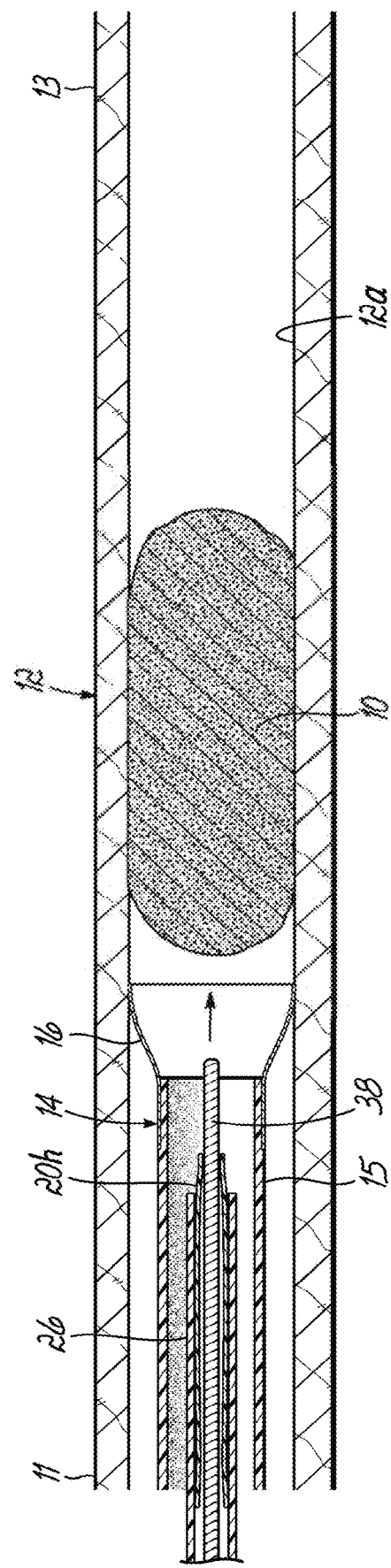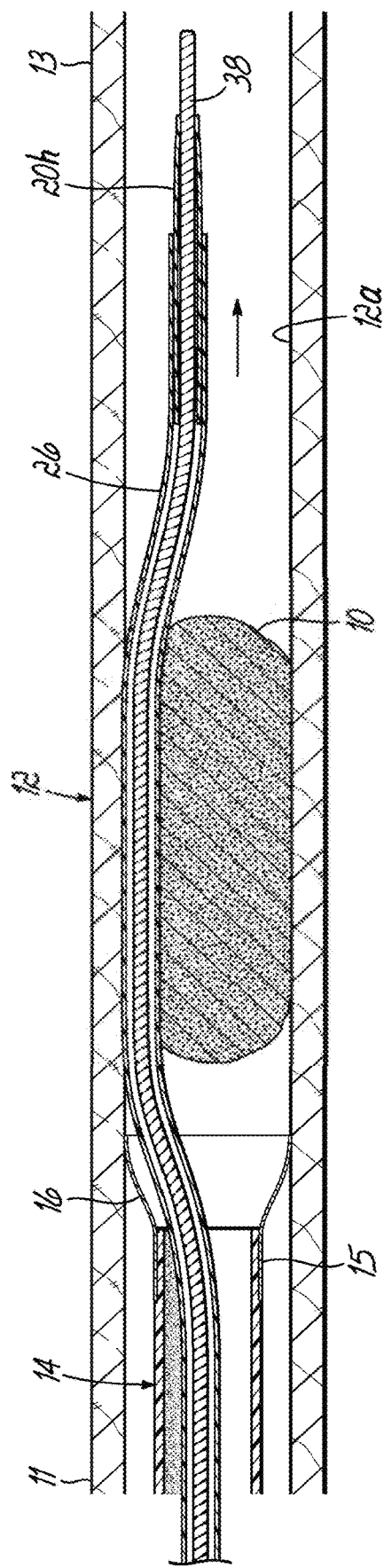
FIG. 10A
FIG. 10B

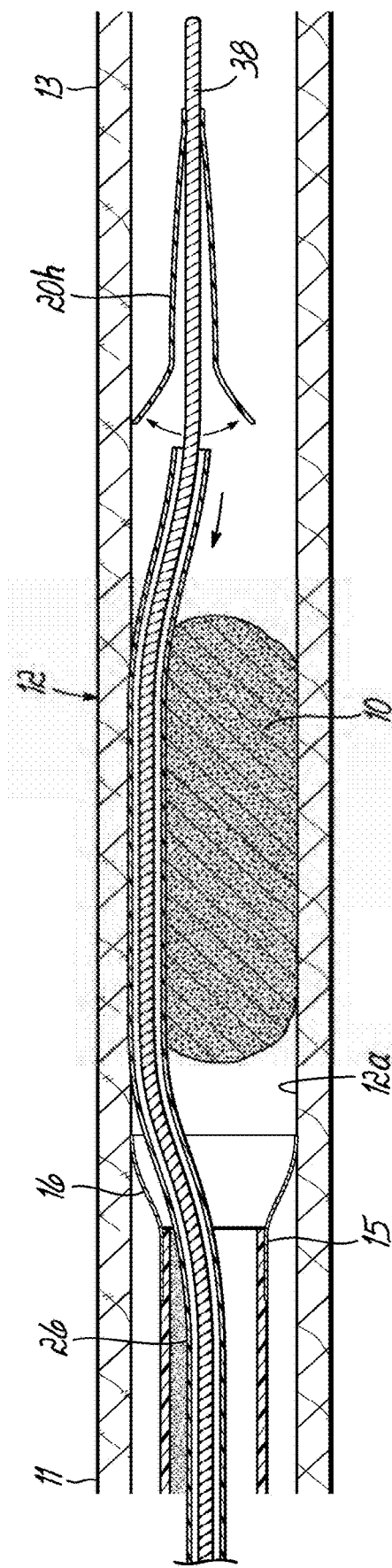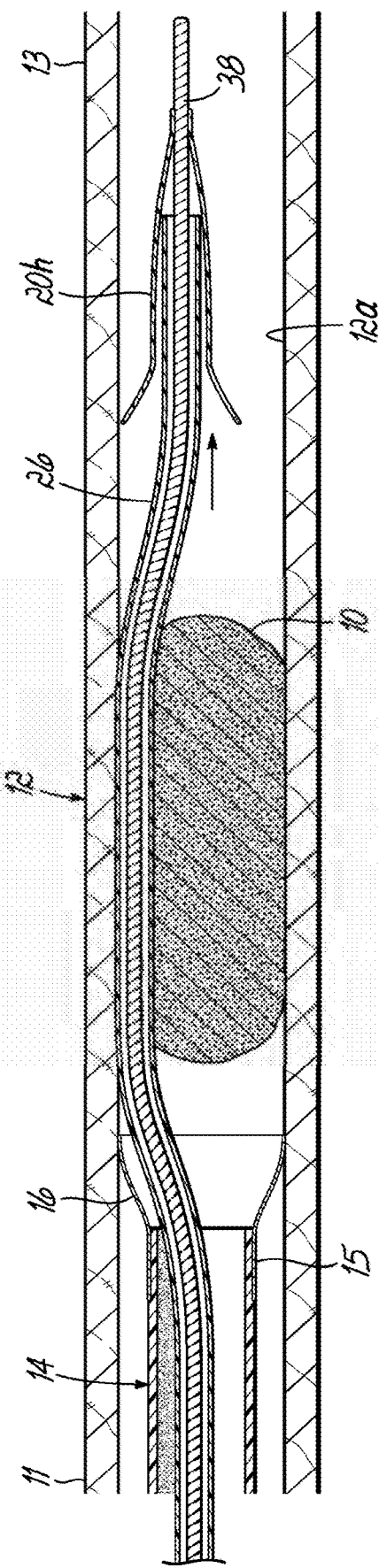

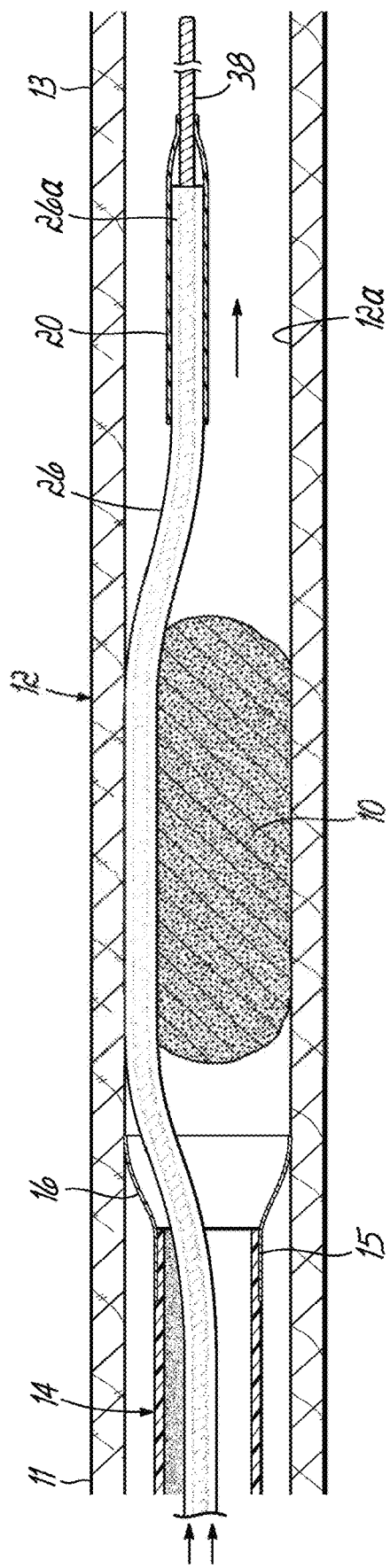
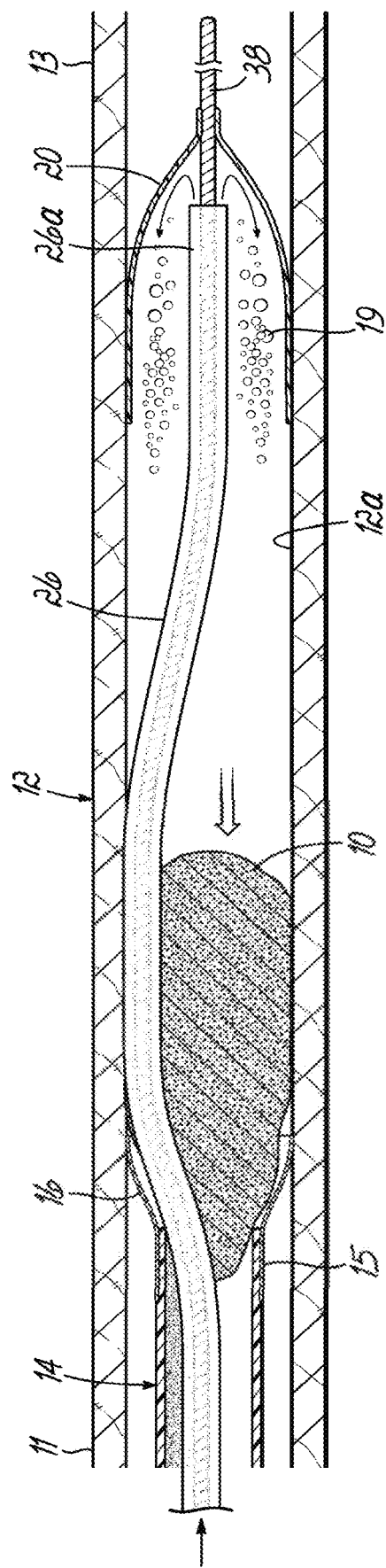
FIG. 11A
FIG. 11B

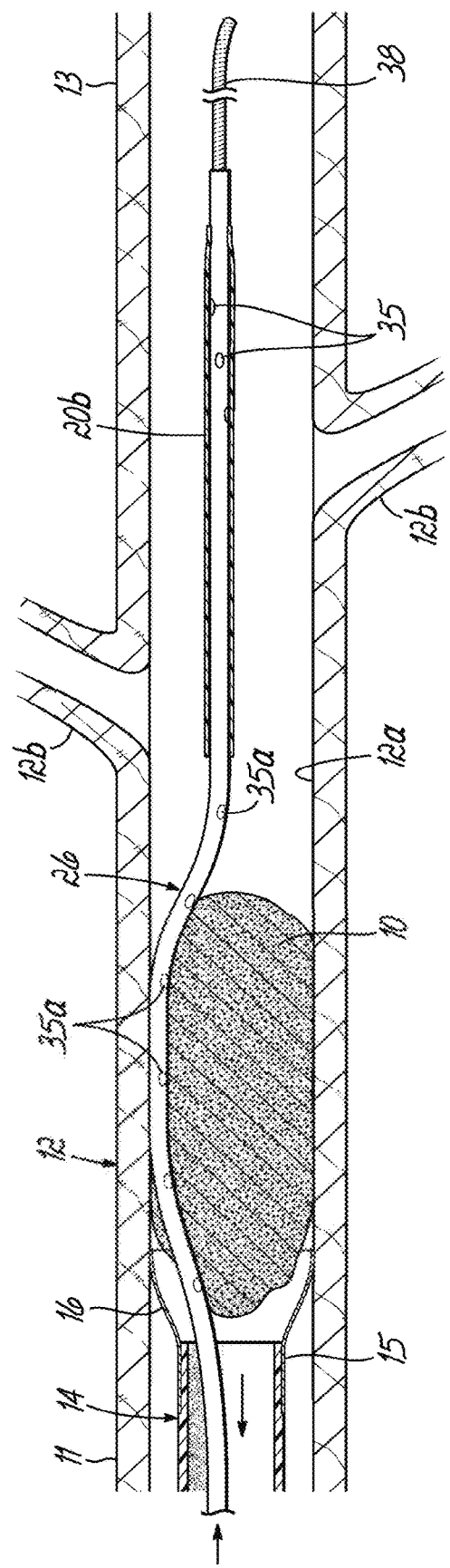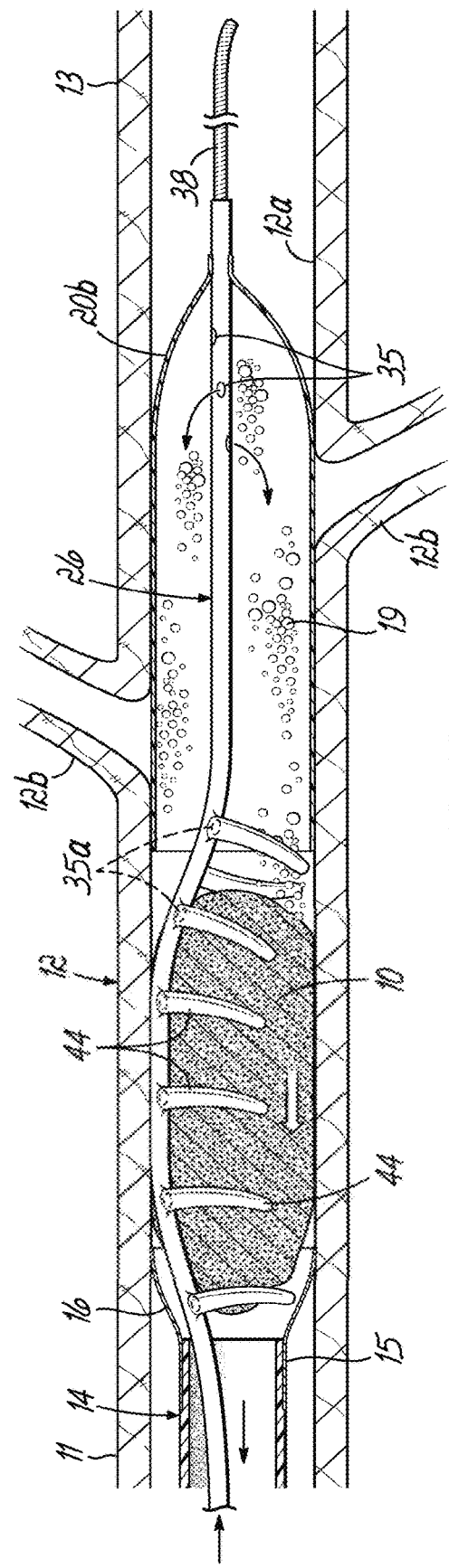
FIG. 12A
FIG. 12B

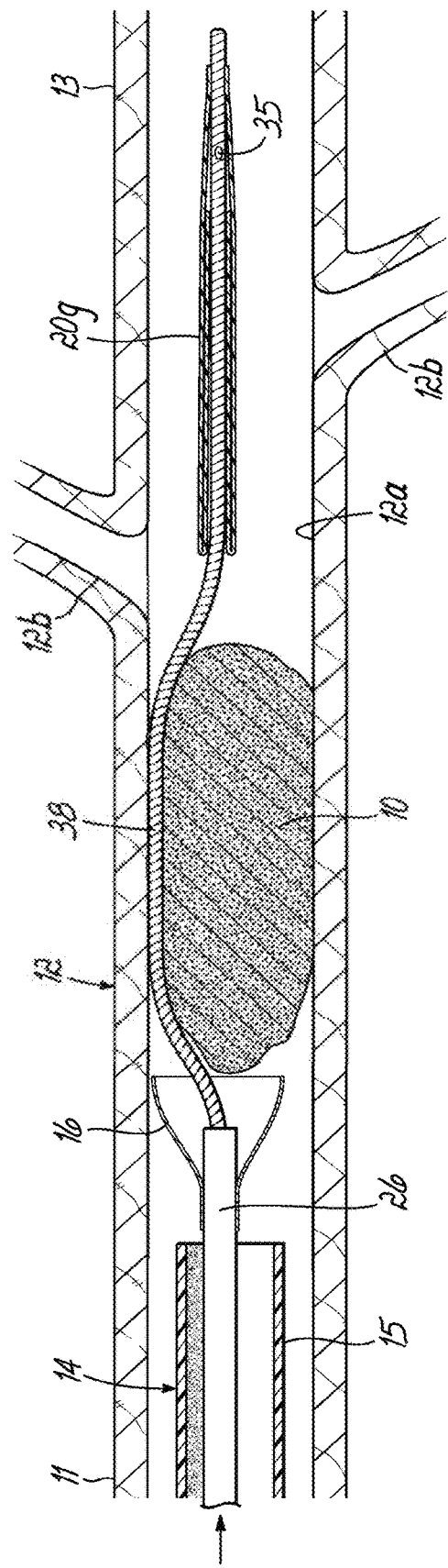
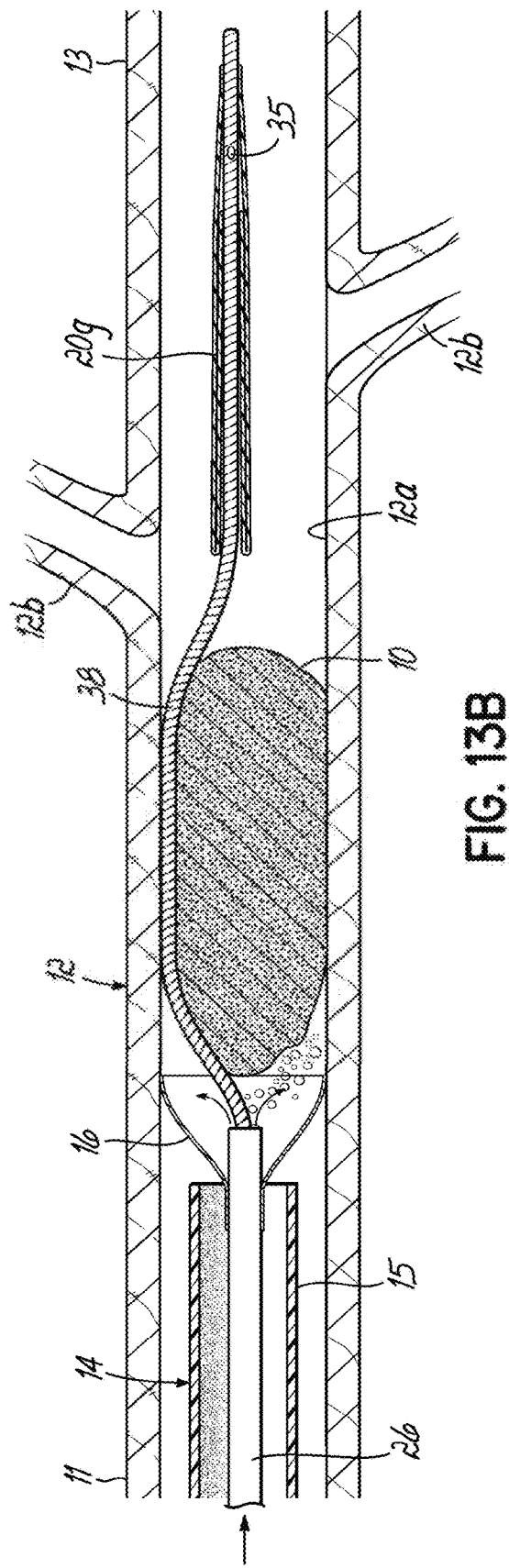
FIG. 13A
FIG. 13B

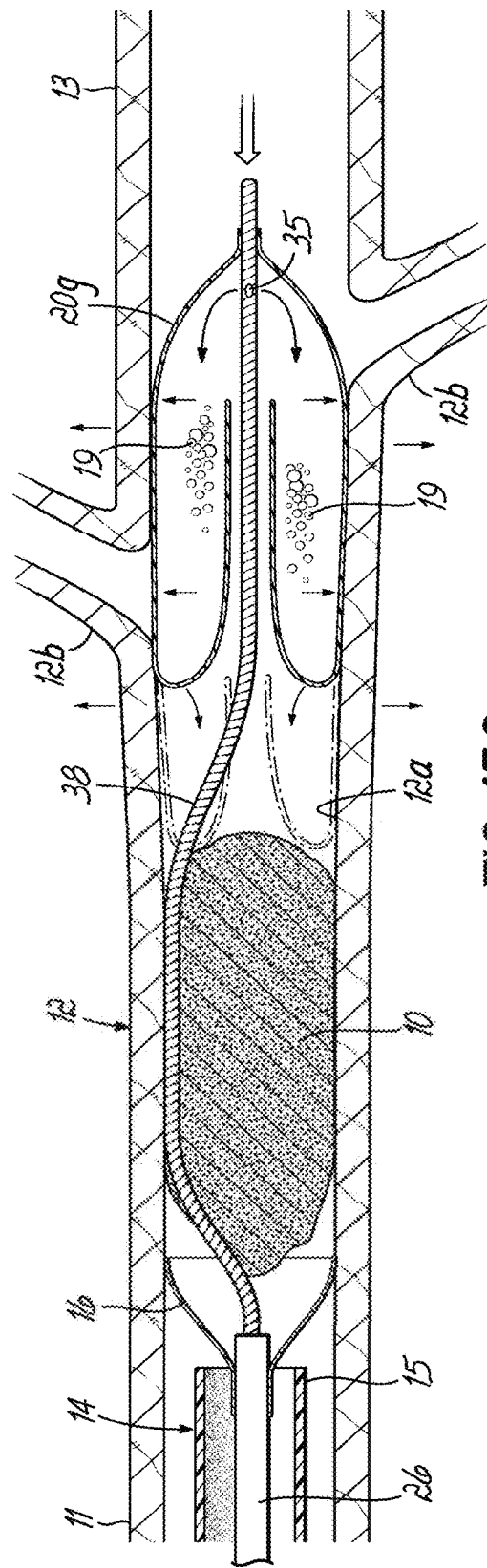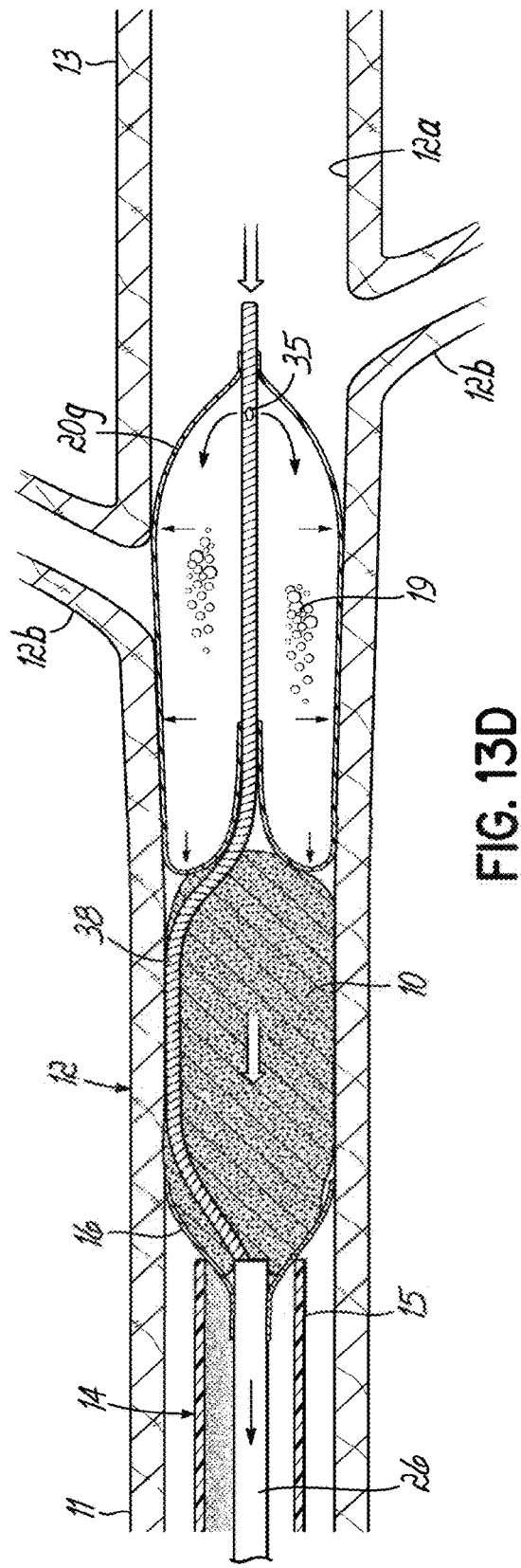
FIG. 13C
FIG. 13D

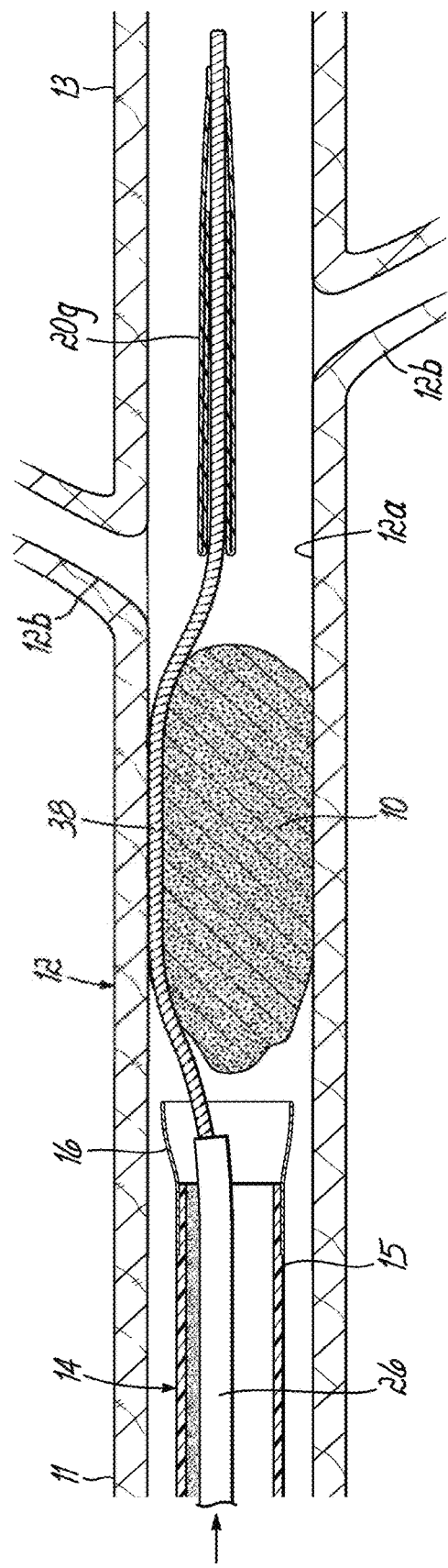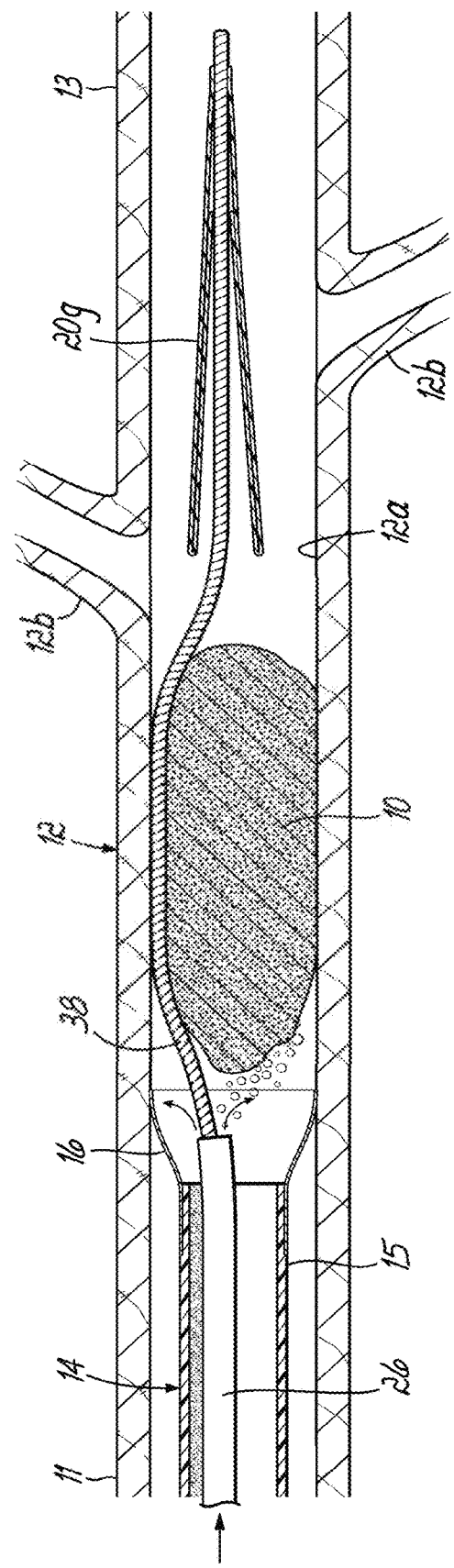
FIG. 14A
FIG. 14B

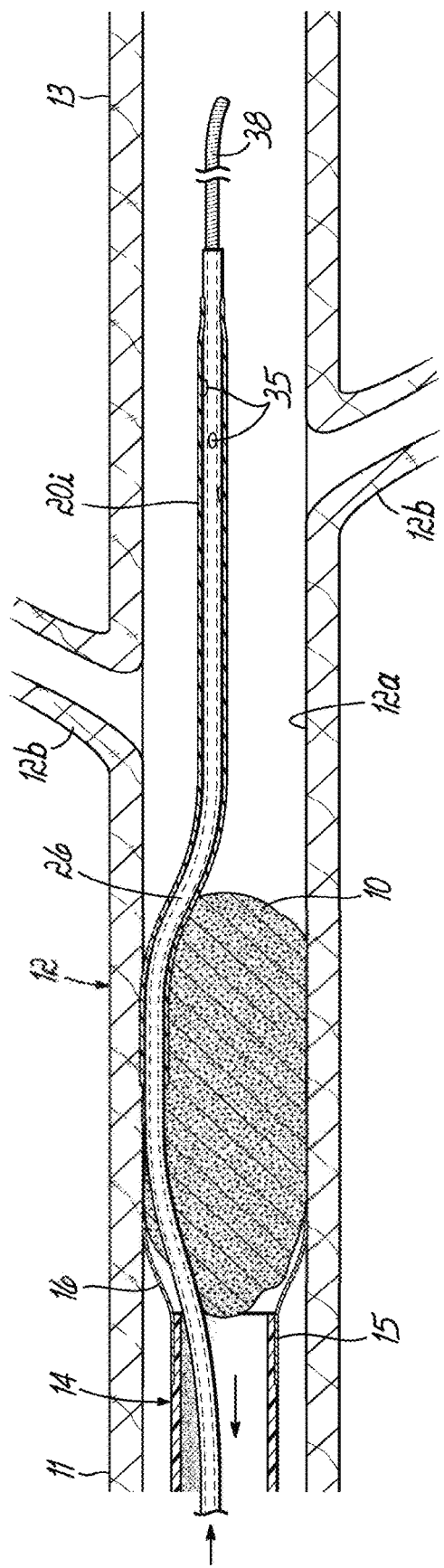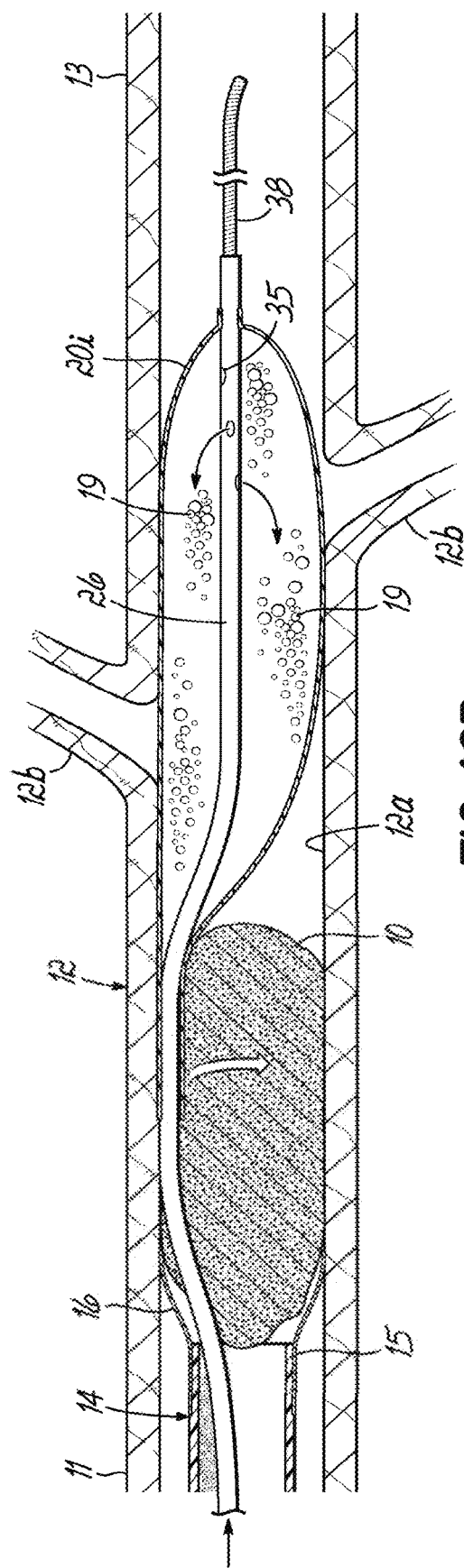
FIG. 16A
FIG. 16B

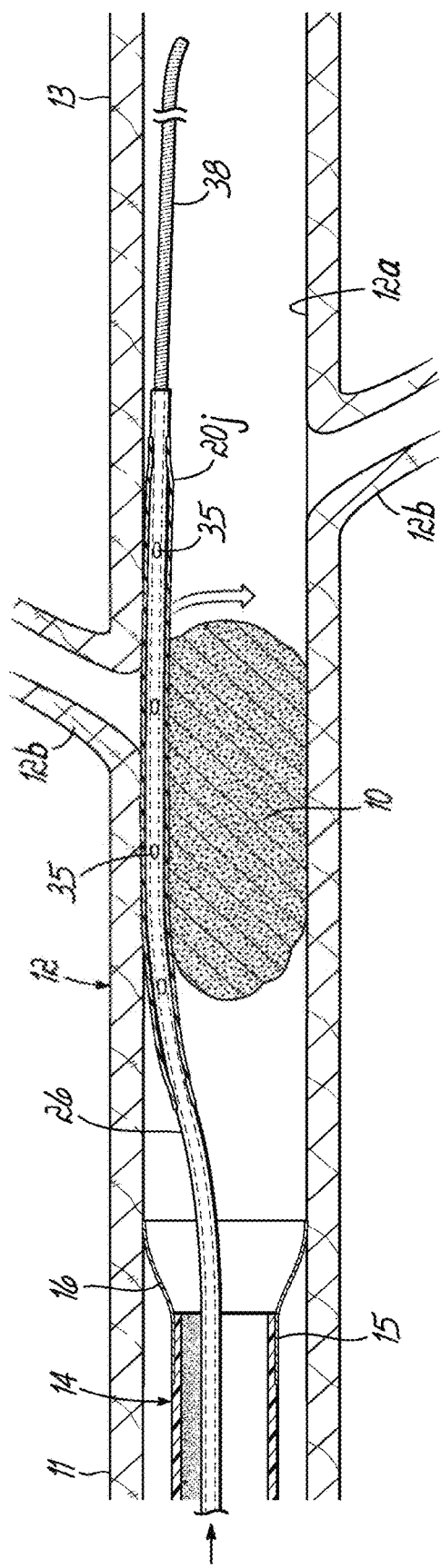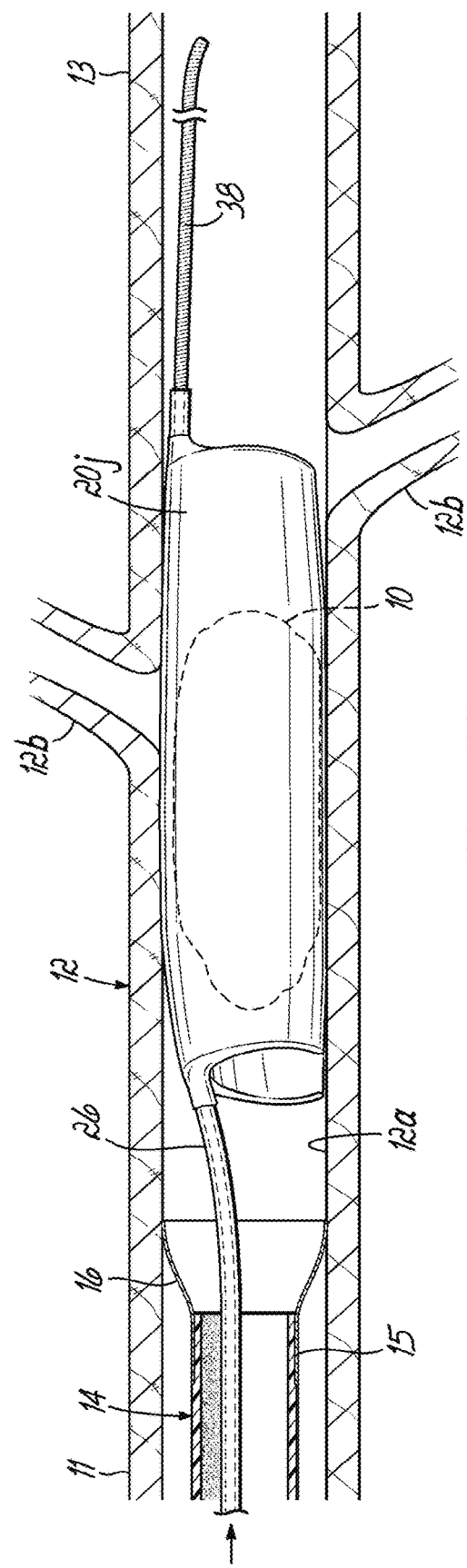

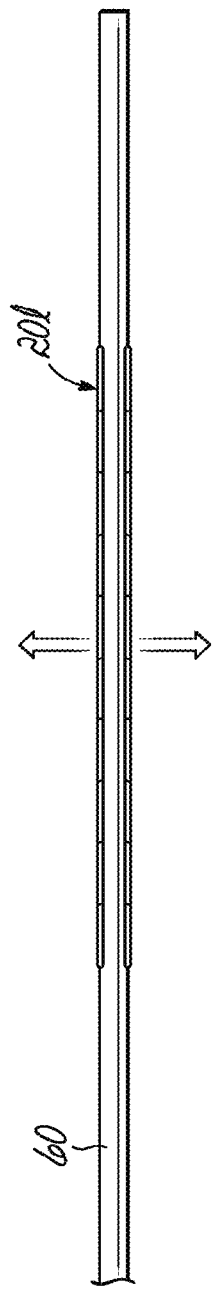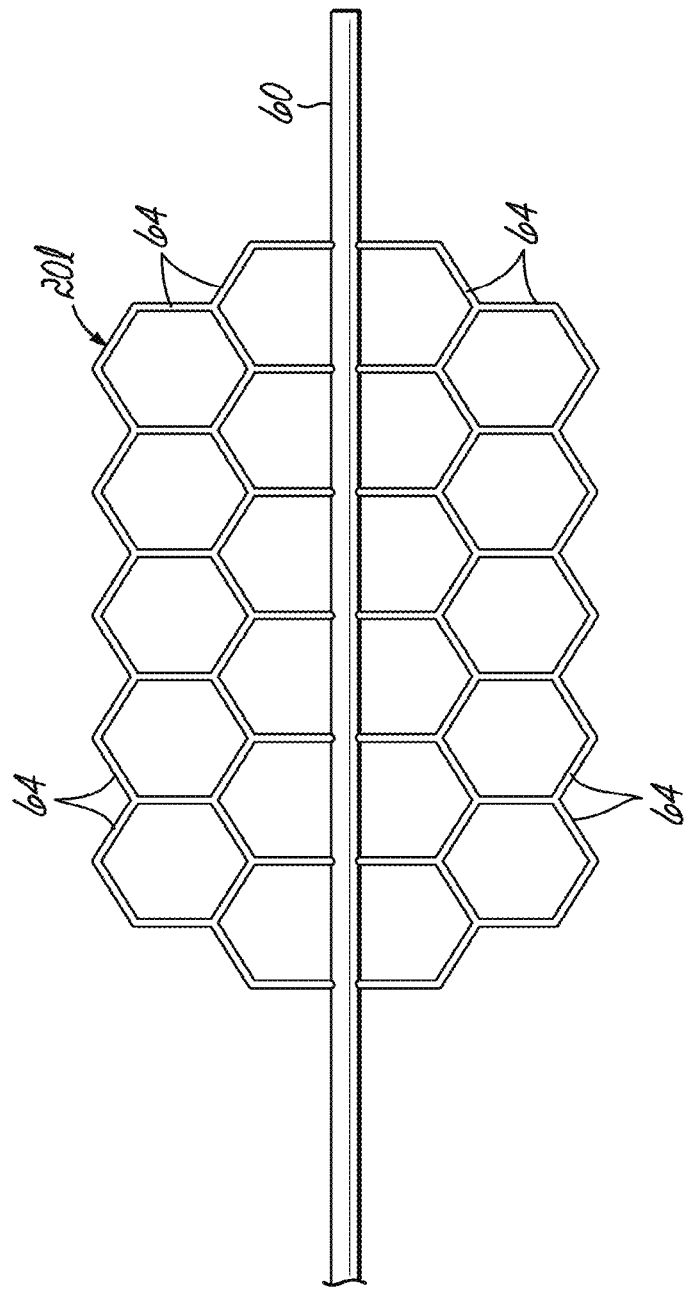

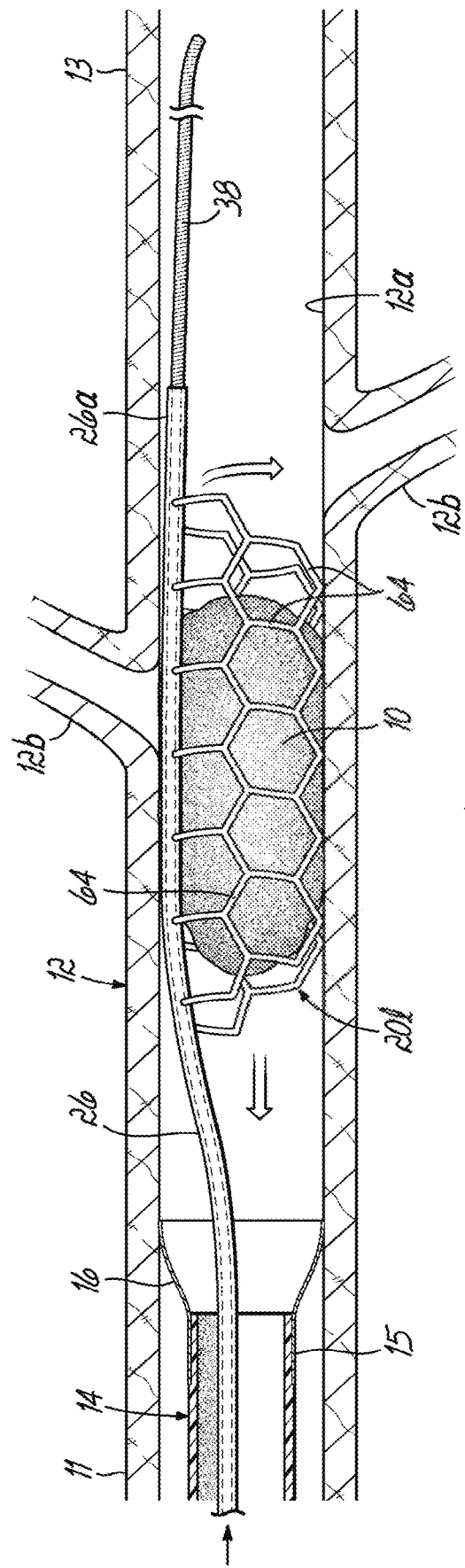

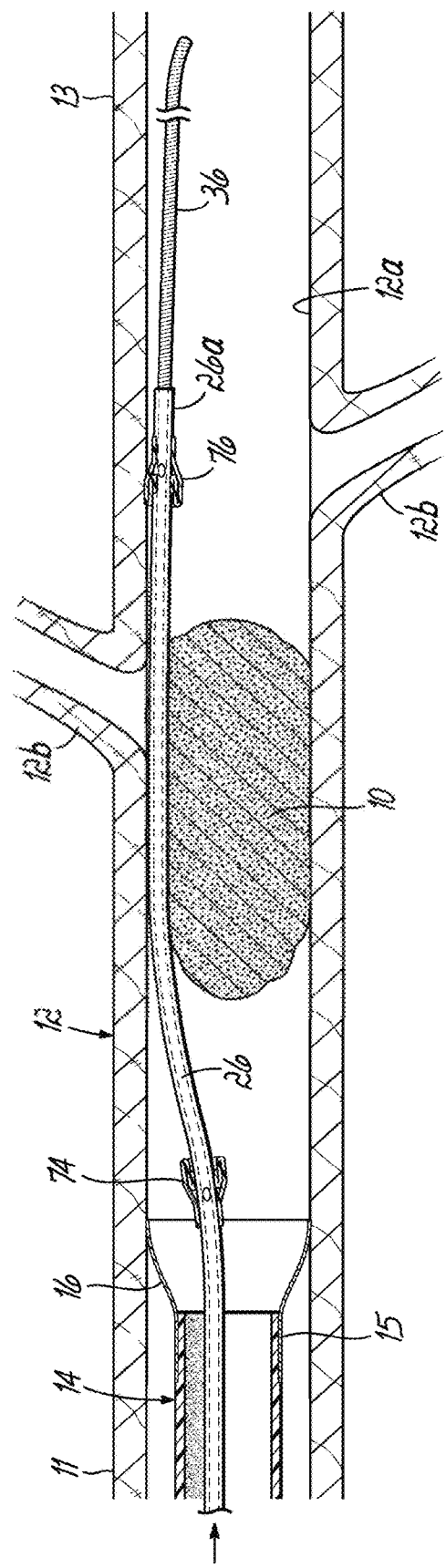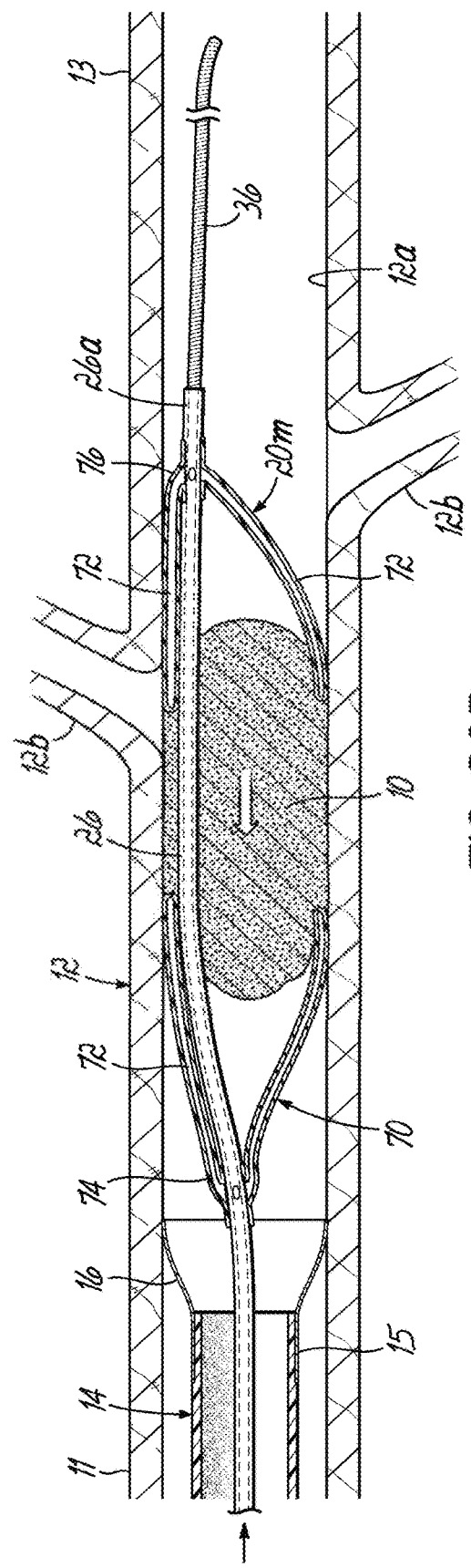
FIG. 20A
FIG. 20B

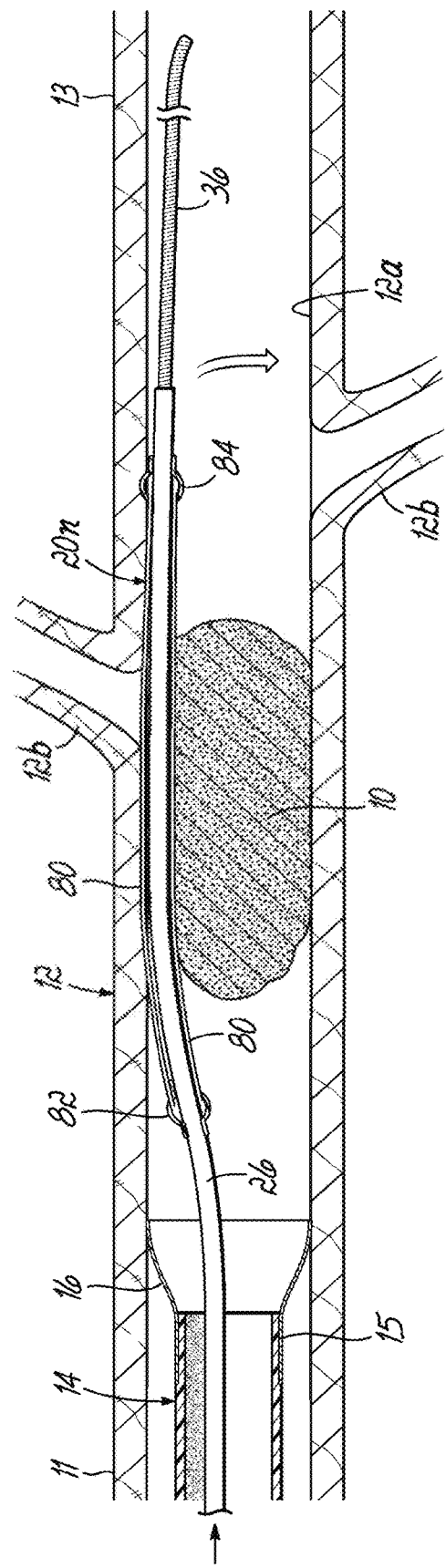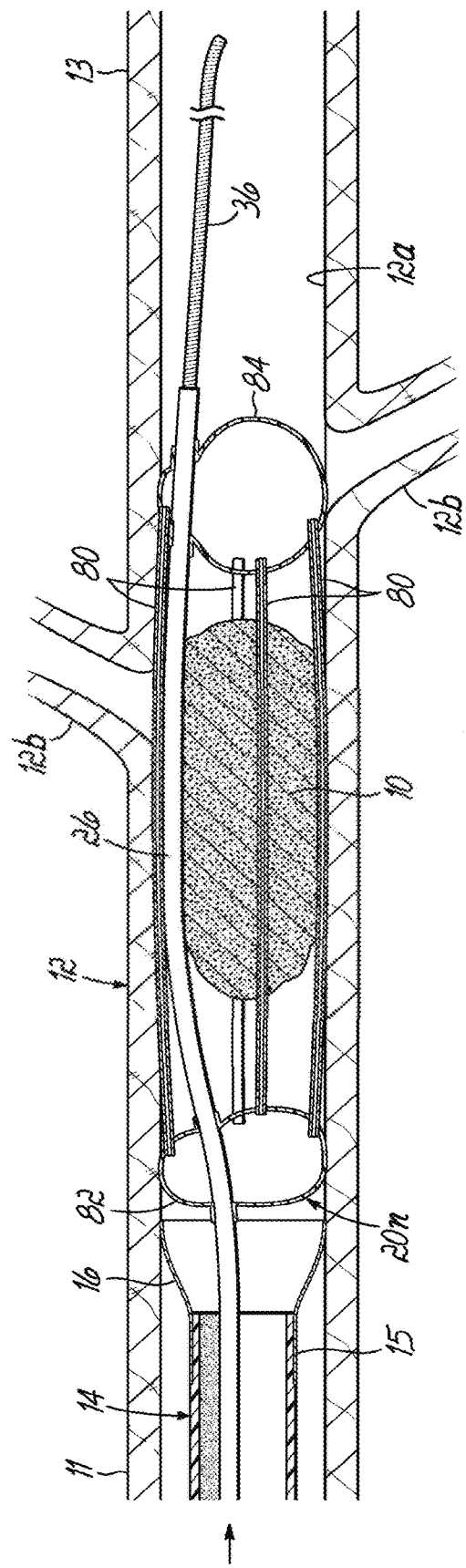

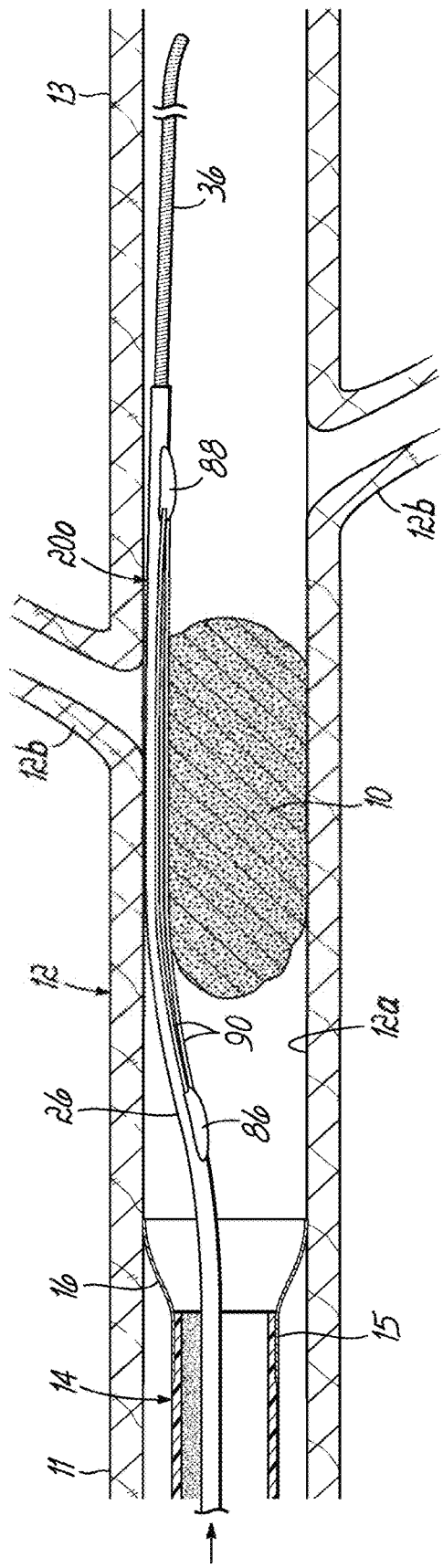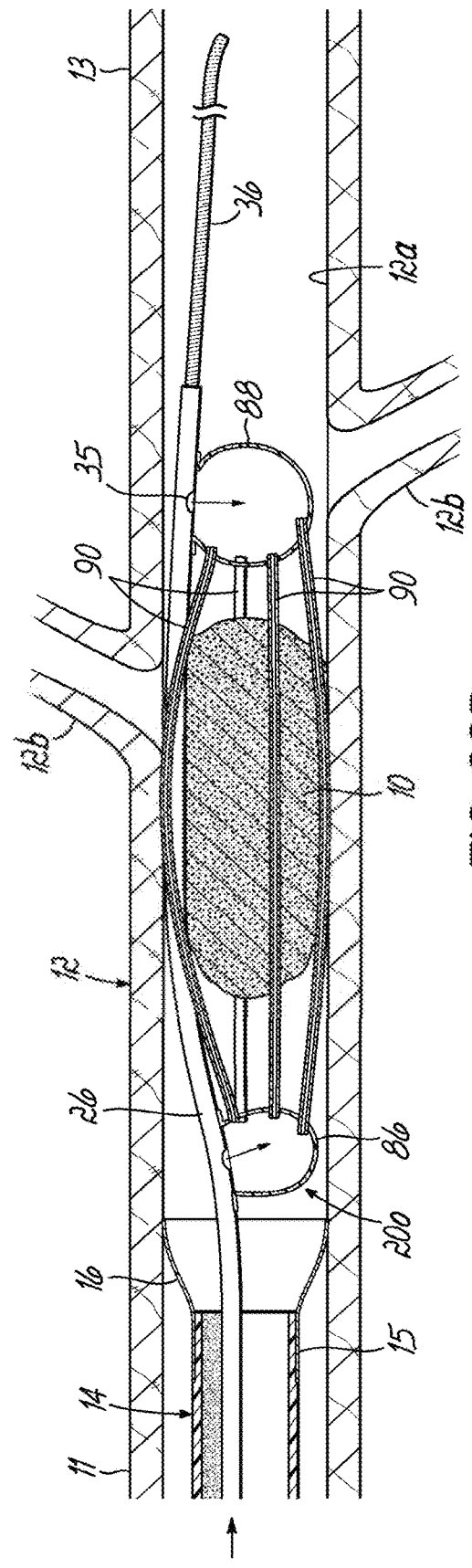
FIG. 22A
FIG. 22B

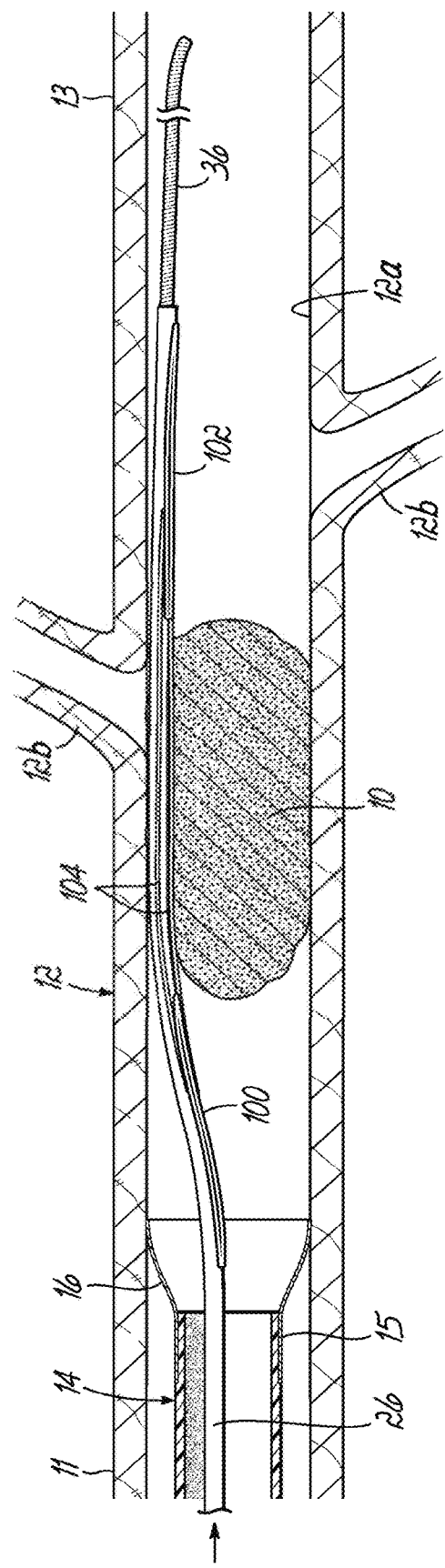
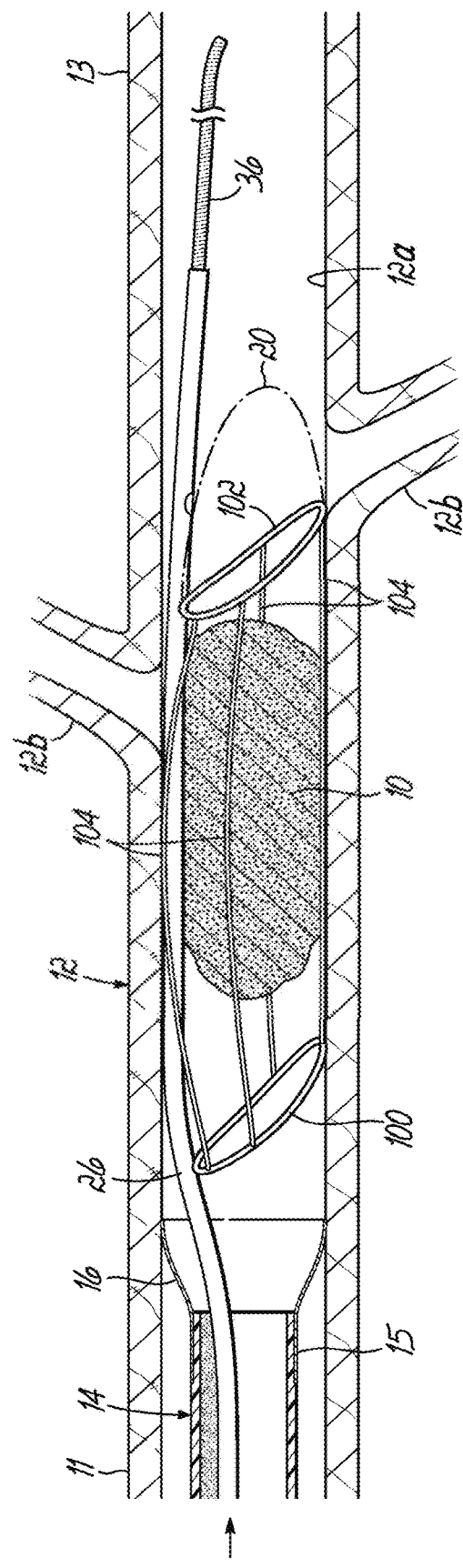
FIG. 24A
FIG. 24B

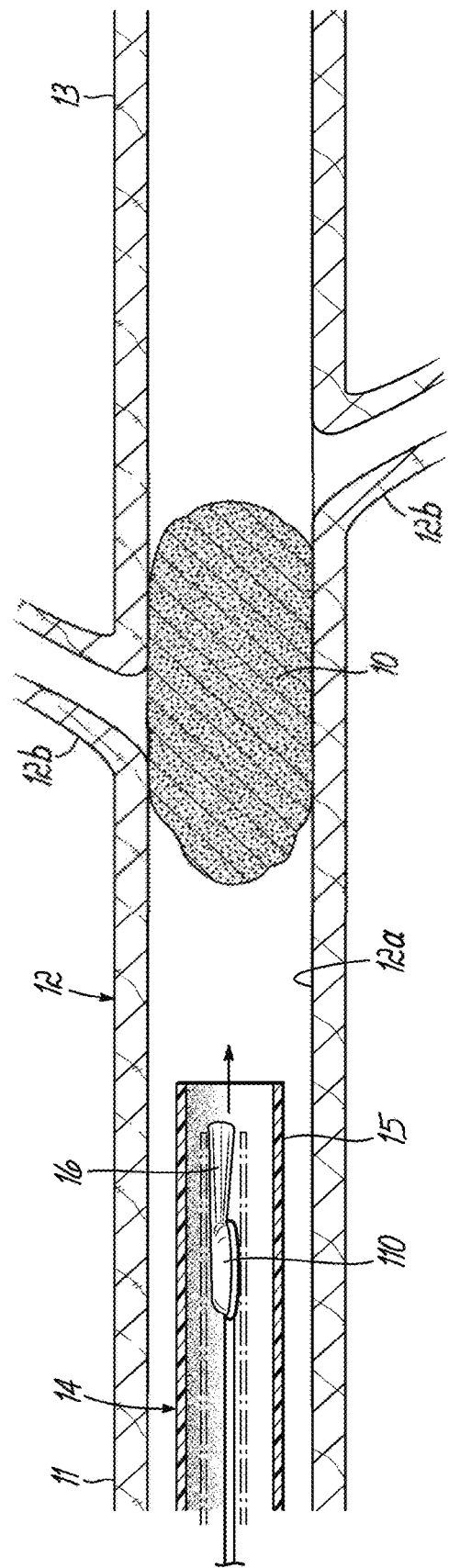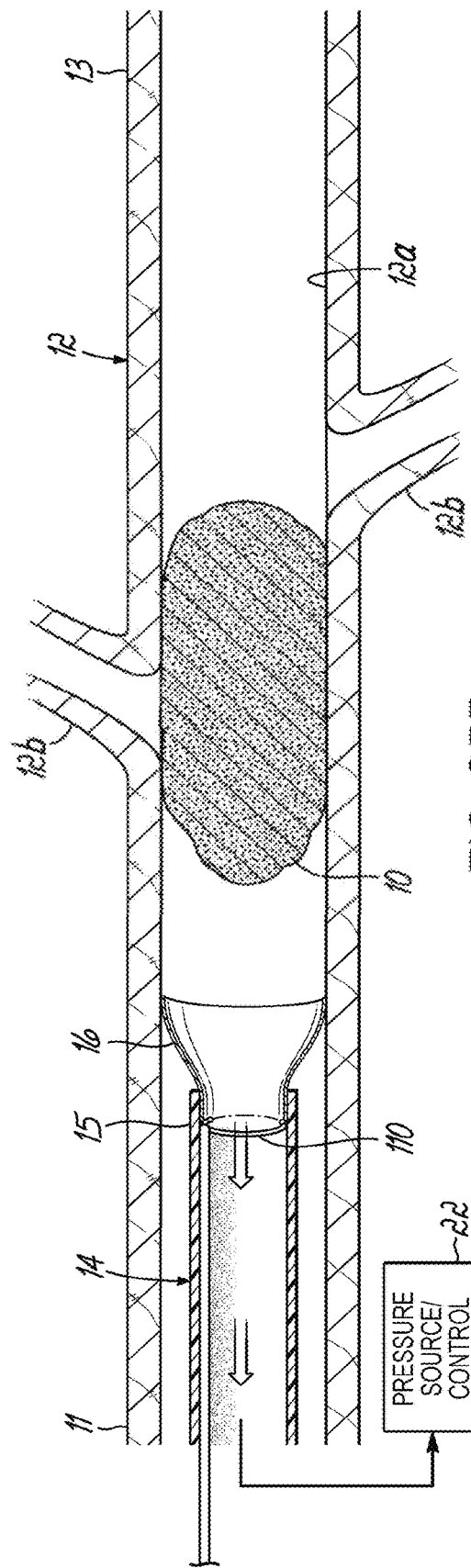

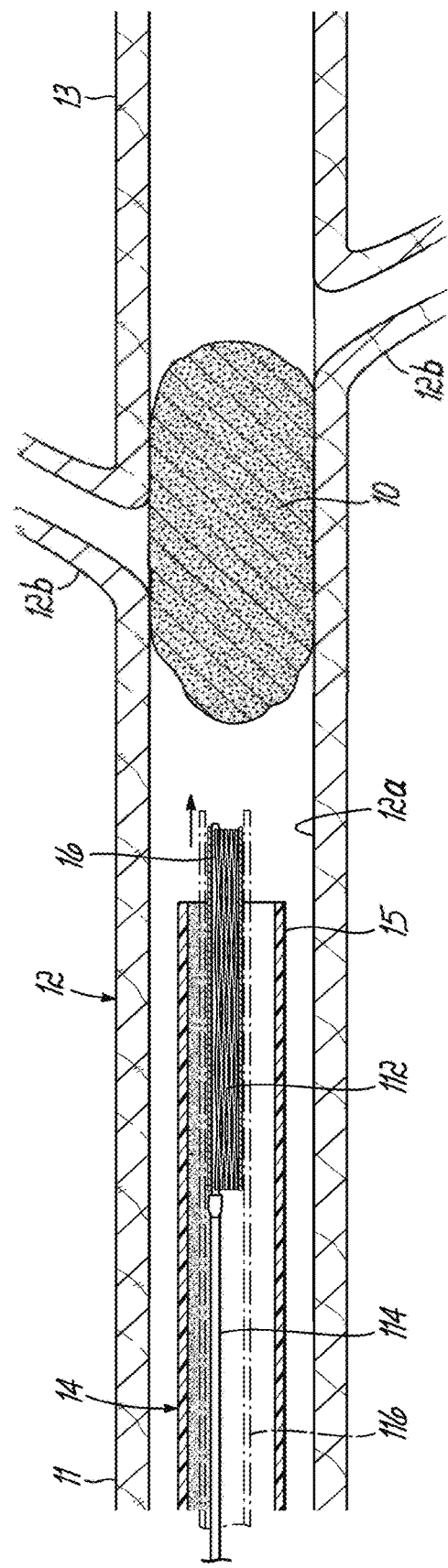
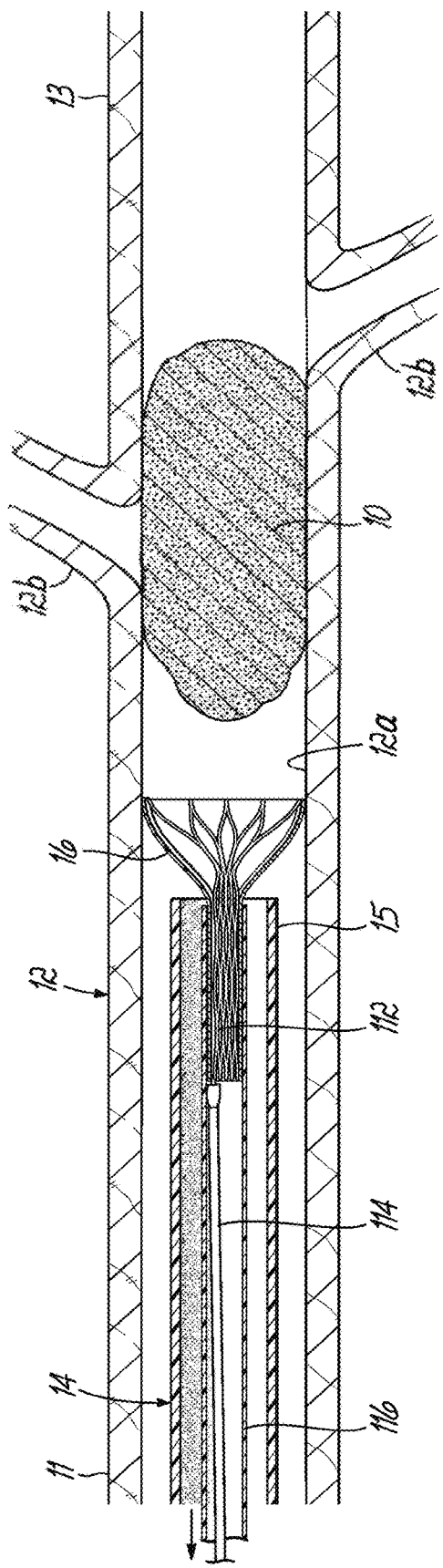
FIG. 26A
FIG. 26B

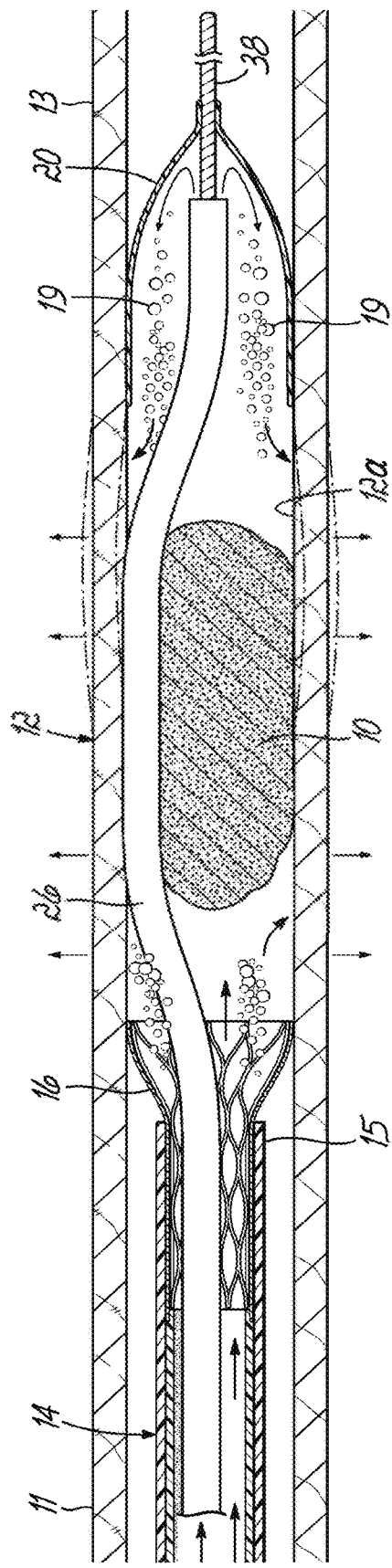
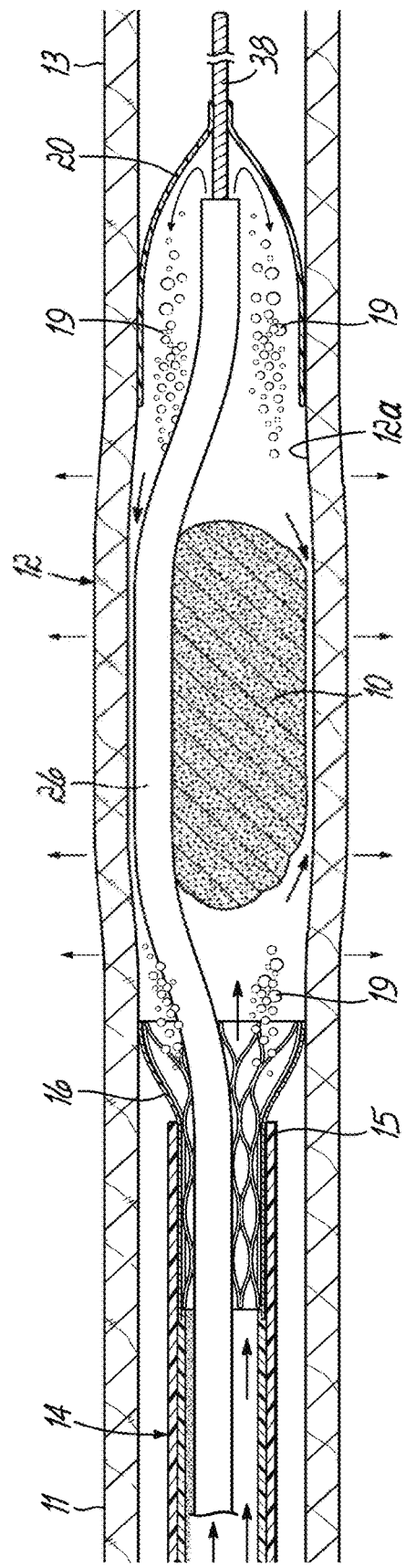
FIG. 28C
FIG. 28D

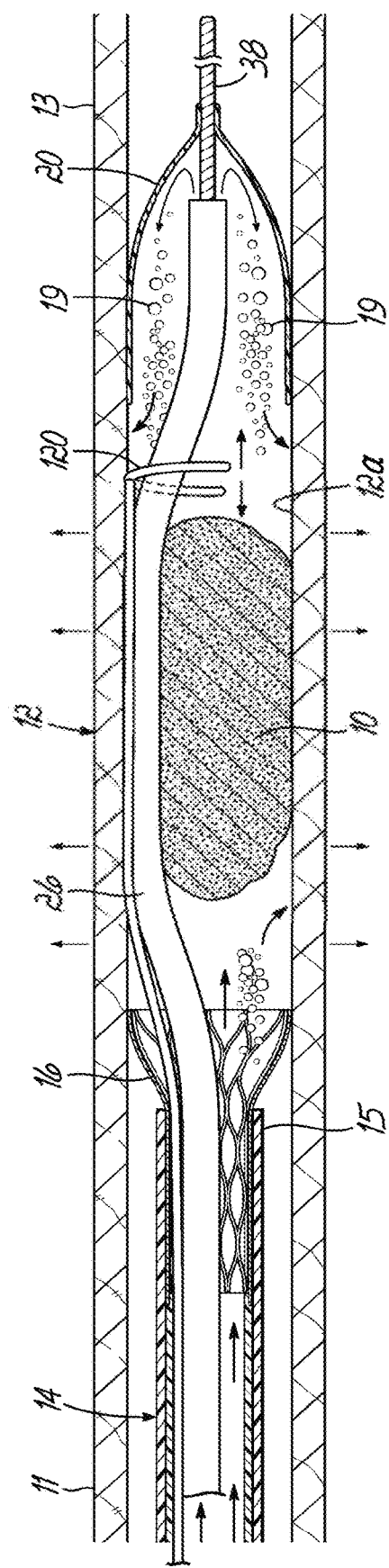
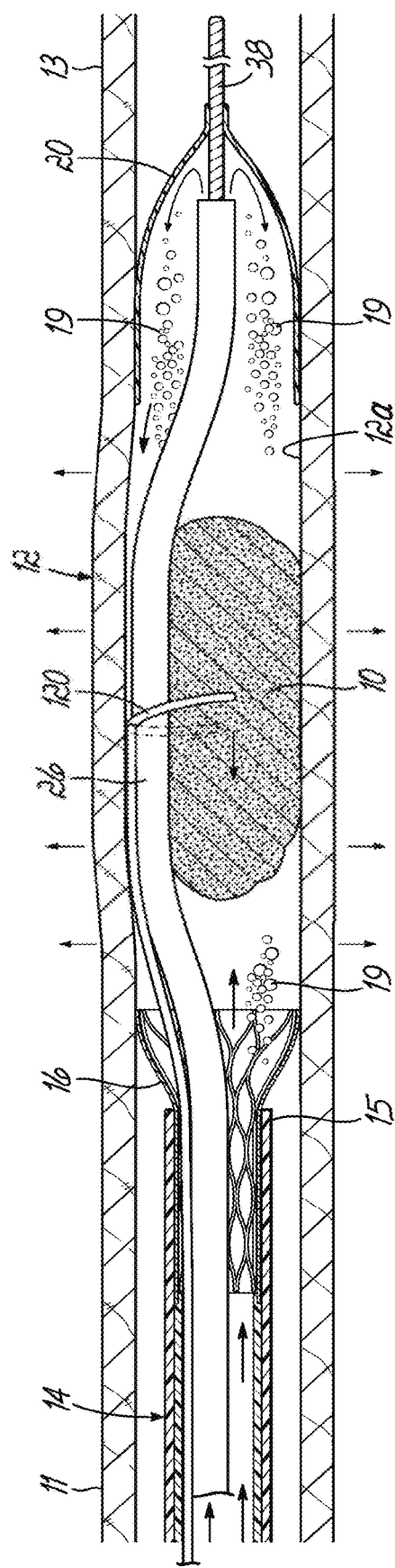
FIG. 29A
FIG. 29B

DEVICES, SYSTEMS AND METHODS TO REMOVE BLOOD CLOTS

CROSS-REFERENCE TO RELATED APPLICATION

This application is a continuation of U.S. patent application Ser. No. 18/475,929, filed Sep. 27, 2023, which is a continuation of U.S. patent application Ser. No. 17/379,566, now U.S. Pat. No. 11,793,532, filed Jul. 19, 2021, which is a continuation of U.S. patent application Ser. No. 16/637,046, now U.S. Pat. No. 11,065,017, filed Feb. 6, 2020, which is a 371 U.S. National Phase entry of International Application No. PCT/US2019/015220, filed Jan. 25, 2019, which claims the priority to and benefit of U.S. Provisional Patent Application Nos. 62/621,776, 62/654,693, and 62/775,510 filed on Jan. 25, 2018, Apr. 9, 2018, and Dec. 5, 2018, respectively, each entitled "Devices, Systems and Methods to Remove Blood Clots," the disclosures of each of which are incorporated herein by reference in their entirety.

BACKGROUND

Stroke is a sudden and often severely debilitating medical event for many people. Stroke can cause sudden death, and even survivors can lose the ability to speak, walk, feed and care for themselves. These patients frequently need long term care and have limited life expectancy.

The most common cause of a stroke is an obstruction of an artery in the brain caused by lodgment of a blood clot. The clot or embolus dislodges from a source such as the heart or an artery in the neck, and travels into a brain artery. As the artery narrows, the clot eventually becomes fixed or stuck in position. Flow ceases to the region of the brain beyond the obstruction and severe damage often occurs. The brain is very unforgiving of lost blood flow. Many regions are supplied by only one source of blood, and the function of the brain is not replicated. Once a motor or speech area is lost, there is limited ability for other segments of the brain to take over the lost function.

The typical treatment for stroke was conservative, watchful therapy. With this approach the outcome can often be unsatisfactory. Another form of therapy involves the use of clot dissolving agents. However, these agents can only provide limited benefit.

More recently, important advances have occurred in catheterized blood clot removal techniques. Now, if stroke patients are brought to a catheterization laboratory ("cath lab") promptly after the clot has lodged, the clot may be removed to more quickly restore blood flow. In such cases the survival and functional status of these patients can dramatically improve. Instead of most patients either dying or being transferred to nursing facilities, most patients survive and can live independently.

The tools currently developed and available to remove blood clots in the brain are still in their early development. An important aspect of treatment can be the use of constant suction pressure at a location proximal to the blood clot coupled with stent-like blood clot retrievers ("stent-trievers") that physically trap the clots and allow removal. There is still considerable room for improvement in these devices. In addition, a meaningful percentage of patients who enter the cath lab for clot removal have no restoration of blood flow. More effective systems, devices and methods are necessary to treat these people.

One of the key challenges relates to the small blood vessels containing the blood clots. These blood vessels may have internal diameters of about 2 mm or less. The vessels are often deep inside the brain and the path to reach them is tortuous. These realities create great challenges. But the reward for solving these problems is immense for those unfortunate enough to suffer a stroke.

Most strokes are treated with constant suction pressure proximal to the clot. The suction is provided by a catheter placed near or proximate the clot. If this is not sufficient, or if the interventionist prefers, a guidewire is passed adjacent to or through the clot and then distally beyond the clot. This guidewire is then used to guide the delivery of a stent-triever inside a small catheter. A stent-triever is deployed adjacent to the clot and is used to trap and physically remove the clot. The stent-triever may cause complications by breaking up the blood clot into pieces that travel distally or downstream into even smaller brain vessels. This causes obstruction of distal blood vessels and can cause more brain damage and disability for the patient. It would be useful to remove the blood clot while minimizing further risk of such additional harm to the patient.

The stent-triever involves an additional step. The guidewire must be introduced into the blood vessel proximate the blood clot. A stent-triever is then passed over the guidewire to the site of the clot. It would be advantageous to provide devices that simplify this procedure.

Adding too much suction to a blood vessel may cause the vessel to collapse, making it even harder to remove the clot. Therefore, a physician using current systems, devices and methods based on constant suction fluid pressure must balance the need for using sufficient pressure to dislodge the blood clot with the competing need to avoid blood vessel collapse. Unfortunately, many cases can involve a blood clot that is securely attached to and/or lodged against the interior wall surface of the blood vessel making removal with current techniques very difficult or impossible. Aggressive use of current techniques in an effort to remove strongly adhered or lodged clots can result in complications harmful to the patient.

For these and other reasons, it would be desirable to provide systems, devices and methods for more effectively treating stroke by removing blood clots during a catheter procedure.

SUMMARY

In a first illustrative embodiment, a system is provided for removing a blood clot from a blood vessel of the patient. The system comprises a catheter having a distal end portion. A fluid pressure delivery apparatus is operative to apply suction fluid pressure intravascularly through the distal end portion of the catheter to a proximal side of the blood clot. A blood clot retrieval element captures the blood clot in the blood vessel. A control is operatively coupled with the fluid pressure delivery apparatus and/or the catheter to repeatedly cycle the suction fluid pressure in the blood vessel between different pressure levels for assisting with dislodgement and removal of the blood clot.

Optionally, the system may further comprise a radially expandable distal seal deployable from the distal end portion of the catheter. The radially expandable seal includes a proximal end portion and a distal end portion and is configured to expand radially in use and engage with the interior wall surface of the blood vessel. The seal is open at its proximal end portion. As another option, the distal radially expandable seal may self-adjust in size to accommodate blood vessels of differing diameter. For example, this self-adjustment may occur as the blood clot is pulled proximally during removal and the blood vessel enlarges. In that case, the expandable seal will also enlarge in size to maintain the seal. A fluid pressure delivery apparatus may then apply positive fluid pressure intravascularly into an area of the blood vessel contained by the radially expandable seal. A control is operatively coupled with the fluid pressure delivery apparatus to repeatedly cycle the positive fluid pressure in the blood vessel between different pressure levels distal to the blood clot for assisting with dislodgement and removal of the blood clot.

In another illustrative embodiment, a system is provided for removing a blood clot from a blood vessel of the patient and includes a catheter with a distal end portion, a radially expandable seal, a fluid pressure delivery apparatus, and a blood clot retrieval element. The radially expandable seal is deployable from the distal end portion of the catheter and is configured to expand radially in use and engage with the interior wall surface of the blood vessel. The fluid pressure delivery apparatus applies fluid pressure intravascularly through the catheter to an area of the blood vessel between the radially expandable seal and the blood clot. The blood clot retrieval element captures the blood clot in the blood vessel. In this embodiment, the seal may be deployed proximal or distal to the blood clot, and in various embodiments, two seals may be deployed with one being deployed proximal to the blood clot and the other being deployed distal to the blood clot. As another option, one or both radially expandable seals may self-adjust in size to accommodate blood vessels of differing diameter. For example, this self-adjustment may occur as the blood clot is pulled proximally during removal and the blood vessel enlarges such that the seals will also enlarge in size to maintain engagement with the interior wall surface of the vessel.

In another illustrative embodiment, a system for removing a blood clot from a blood vessel of the patient is provided and includes a catheter having a distal end portion, a radially expandable seal, a fluid pressure delivery apparatus, and a control. The radially expandable seal is deployable from the distal end portion of the catheter and includes a proximal end portion and a distal end portion. The radially expandable seal is configured to expand radially in use on a distal side of the blood clot, and engage with the interior wall surface of the blood vessel. The seal is open at its proximal end portion. The fluid pressure delivery apparatus applies positive fluid pressure intravascularly into an area of the blood vessel between the radially expandable seal and the blood clot. The control is operatively coupled with the fluid pressure delivery apparatus to repeatedly cycle the positive fluid pressure in the blood vessel between different pressure levels distal to the blood clot for assisting with dislodgement and removal of blood clot.

In another illustrative embodiment a system for removing a blood clot from a blood vessel of the patient is provided and includes a catheter, a fluid pressure delivery apparatus, a blood clot retrieval element, and a radially expandable and emboli capturing element. The catheter has a distal end portion. The fluid pressure delivery apparatus applies fluid suction pressure intravascularly through the distal end portion of the catheter to a location in the blood vessel proximal to the blood clot. The blood clot retrieval element captures a dislodged blood clot in the blood vessel. The radially expandable emboli capturing element is deployable from the distal end portion of the catheter and includes a proximal end portion and a distal end portion. The radially expandable emboli capturing element is configured to expand radially in use and engage with the interior wall surface of the blood vessel. The emboli capturing element is open at its proximal end portion such that the proximal end portion can radially expand on a distal side of the blood clot to capture emboli and prevent the emboli from traveling in a distal direction through the blood vessel. As another option, the radially expandable emboli capturing element may self-adjust in size to accommodate blood vessels of differing diameter. For example, this self-adjustment may occur as the blood clot is pulled proximally during removal and the blood vessel enlarges. In that case, the expandable emboli capturing element will also enlarge in size to prevent escape of emboli in a distal direction.

In another illustrative embodiment an intravascular device is provided for removing a blood clot from a blood vessel. The device comprises an elongate intravascular element sized and configured to be introduced into the blood vessel. The elongate intravascular element includes a distal end portion. A radially expandable seal is carried at the distal end portion of the elongate intravascular element. The radially expandable seal includes a proximal end portion and a distal end portion and is configured to expand radially in use such that at least the proximal end portion or the distal end portion of the seal forms a fluid pressure seal against the interior wall surface of the blood vessel. In various embodiments, the elongate intravascular element may further comprise a catheter, such as a small diameter catheter or what is sometimes referred to herein as a "microcatheter." A guidewire may be used to guide the microcatheter into position proximate the blood clot. In other embodiments, the elongate intravascular element is a guidewire. As another option, the radially expandable seal may self-adjust in size to accommodate blood vessels of differing diameter. For example, this self-adjustment may occur as the blood clot is pulled proximally during removal and the blood vessel enlarges. In that case, the expandable seal will also enlarge in size to maintain the seal.

In some embodiments, various options are available depending on the clinical needs of the patient and/or the desired surgical techniques of the physician. As examples, the radially expandable seal may be open at its distal end portion and the distal end portion may be sized and configured to provide a fluid pressure seal against the interior wall surface of the vessel to allow suction to be applied to a proximal side of the blood clot. In other embodiments the radially expandable seal is open at its proximal end portion and the proximal end portion is sized and configured to provide a fluid pressure seal against the interior wall surface of the blood vessel to allow positive fluid pressure to be applied to a distal side of the blood clot. As will be appreciated from further description provided below, the physician may choose a system that applies either suction pressure or positive pressure, or both suction pressure and positive pressure, proximal and/or distal to the blood clot for assisting with dislodgement and removal of the blood clot. As will be further described herein, the suction and/or positive fluid pressure may be constant pressure, cycled or pulsed pressure, or a combination of both during the clot dislodgement and removal procedure.

The radially expandable seal may take many possible forms depending on the desired characteristics and surgical techniques. For example, the radially expandable seal may comprise an elongate tubular shape for covering openings to one or more side vessel branches of the blood vessel. The radially expandable seal may be further configured to radially retract to allow for delivery through a delivery catheter to the site of the blood clot and then retracted or collapsed into the delivery catheter for removal. At least one tether may couple the radially expandable seal to the elongate intravascular element. The radially expandable seal may comprise a proximal end portion of various configurations, for use at a location distal to the blood clot. For example, the proximal end portion may be oriented either perpendicular to or generally at an acute angle relative to the longitudinal axis of the elongate intravascular element upon expansion of the radially expandable seal. Various shapes, such as sigmoid or other curved or straight lines may define the proximal end portion. The radially expandable seal may be formed in discrete, lengthwise extending sections. The radially expandable seal may be configured to unroll in a direction extending along the longitudinal axis of the elongate intravascular element during deployment and radial expansion of the seal. The radially expandable seal may expand from a location on the elongate intravascular element in opposite directions to at least partially surround the blood clot generally between the blood clot and the interior wall surface of the blood vessel.

The radially expandable seal may be separable from the elongate intravascular element, especially when the elongate intravascular element is a standard catheter. This form of separable seal may be pushed to the distal end portion of the elongate intravascular element and secured in place at the distal end portion. In other embodiments, the radially expandable seal is fixed for delivery with the elongate intravascular element, such as by being formed integrally with the elongate intravascular element, e.g., a catheter.

The radially expandable seal may further include a reinforcing structure, such as a radially expandable stent structure. The radially expandable seal may self-expand in a radial direction as the radially expandable seal is directed out from a delivery catheter. As another option, the radially expandable seal may self-adjust in size to accommodate blood vessels of differing diameter. For example, this self-adjustment may be provided by adding a spring-bias or resilient feature to the seal, such as one or more super-elastic wire elements that will maintain and adjust the radial expansion such that the seal engages the interior wall surface of the vessel even as the vessel diameter changes. Depending on the needs of the application, the material forming the radially expandable seal may take many forms. In cases in which the radially expandable seal must provide a robust fluid pressure seal, the seal may be formed from a membrane material that is highly flexible but imperforate. In other applications where the fluid pressure seal need not be extremely robust, or when the seal is used as an emboli capturing element, a mesh or stent-like structure may be used to accomplish the objectives.

The systems and devices of the many embodiments may further include other optional components and/or features. For example, a guide may be positioned at the distal end portion of the elongate intravascular element. The guide may include at least one guiding portion to steer a second elongate intravascular element sideward toward a periphery of the blood clot. The device may further comprise an inflatable balloon element carrying the guide. The elongate intravascular element may include at least one fluid channel for communicating a fluid pressure change within the blood vessel proximal to and/or distal to the blood clot. The elongate intravascular element may further comprise a plurality of perforations in the distal end portion communicating with the at least one fluid channel. The perforations may be contained in an area of the radially expandable seal to expand the radially expandable seal upon direction of positive fluid pressure through the perforations. The device may further comprise a radially expandable blood clot retrieval element for engaging and retrieving the blood clot in a proximal direction within the blood vessel. The device may further comprise a plurality of expandable projections carried by the elongate intravascular element for engaging and assisting removal of the blood clot. The elongate intravascular element may further include a non-linear section for engaging generally between the blood clot and the interior wall surface of the blood vessel. The non-linear section may further comprise a generally sinusoidal or helical section. The device may further include a positive pressure tube for delivering positive fluid pressure proximate the blood clot to thereby assist with removal of the blood clot. An elongate blood clot dislodging element may be provided and configured to extend between the blood clot and the interior wall surface of the blood vessel for dislodging the blood clot from the interior wall surface. A guide may be provided and configured to direct the elongate blood clot dislodging element sideward generally toward a periphery of the blood clot.

In other aspects and illustrative embodiments methods of removing a blood clot from a blood vessel of the patient are provided. For example, in one general method suction fluid pressure is applied within the blood vessel on the proximal side of the blood clot. The suction fluid pressure is repeatedly cycled between different pressure levels proximal to the blood clot for assisting with dislodgement and removal of the blood clot using a pulling force. The blood clot is dislodged from an interior wall surface of the blood vessel, and the blood clot is removed from the blood vessel with a catheter.

Various secondary features and steps of the method may be provided. For example, the suction fluid pressure may be cycled at a frequency exceeding 1 Hz. The amplitude or difference between the higher and lower pressures may, for example, be 20 mm Hg or more. Generally, fluid pressures may be used in accordance with any levels deemed not to be harmful to the patient. This may include fluid pressures above, at, or below the normal blood pressure range for the patient. The method may further comprise using a tool to assist with dislodging the blood clot from the interior wall surface of the blood vessel. The method may further comprise using a retrieval tool to remove the blood clot from the blood vessel. The suction fluid pressure may be repeatedly cycled in a pressure range below the normal blood pressure range of the patient. Removing the blood clot may further comprise directing the blood clot into and through the catheter. Alternatively, removing the blood clot may further comprise retaining the blood clot at the distal end portion of the catheter and then withdrawing the catheter from the blood vessel.

Another method in accordance with an illustrative embodiment comprises deploying a radially expandable seal in engagement with an interior wall surface of the blood vessel proximate the blood clot. Fluid pressure is then applied in an area of the blood vessel between the radially expandable seal and the blood clot to at least assist with this engaging the blood clot from the interior wall surface. The blood clot is then removed from the vessel with the catheter.

In secondary or optional steps of the method, any of the other features as discussed herein may be employed. For example, the steps of deploying the radially expandable seal and applying fluid pressure may respectively further comprise engaging the expanded seal on a proximal side of the blood clot, and applying suction fluid pressure. In another optional aspect, applying suction fluid pressure may further comprise applying constant fluid pressure and/or cycled or pulsed suction fluid pressure. When cycling the suction fluid pressure, the suction fluid pressure may be cycled in a range below the normal blood pressure of the patient. Alternatively, or additionally, the steps of deploying the radially expandable seal and applying fluid pressure may respectively further comprise engaging an expanded seal on a distal side of the blood clot, and applying positive fluid pressure. Again, this positive fluid pressure may be comprised of constant fluid pressure and/or cycled or pulsed fluid pressure. When cycling the positive fluid pressure, the cycled fluid pressure may be in a range above the normal blood pressure of the patient.

Another method in accordance with an illustrative embodiment involves deploying a radially expandable emboli capturing element in engagement with an interior wall surface of the blood vessel distal to the blood clot. This element may also be referred to as a "seal" even though it may not provide any fluid sealing function but, instead, seals the vessel distal to the blood clot against emboli migrating distally and causing further stroke. Suction fluid pressure is applied in an area of the blood vessel proximal to the blood clot to at least assist with disengaging the blood clot from the interior wall surface. The blood clot is then removed from the blood vessel with the catheter. In this embodiment, the radially expandable emboli capturing element is used to capture emboli that may travel in a distal direction during the method or procedure. Any of the secondary or other optional features or steps discussed above or in the detailed description to follow may be used in this method, as well as in any other disclosed methods.

Various other aspects, advantages, features, or combinations of features and/or steps will be appreciated from the detailed description of the illustrative embodiments to follow, taken in conjunction with the accompanying drawings.

BRIEF DESCRIPTION OF THE DRAWINGS

FIG. 2A is a is a longitudinal cross-sectional view schematically illustrating a system in accordance with another embodiment being used to dislodge and remove a blood clot.

FIG. 2B is a view similar to FIG. 2A but illustrating a subsequent step in the method of dislodging and removing the blood clot.

FIG. 3A a is a longitudinal cross-sectional view schematically illustrating a system in accordance with another embodiment being used to dislodge and remove a blood clot.

FIG. 3B is a view similar to FIG. 3A but illustrating a subsequent step in the method of dislodging and removing the blood clot.

FIGS. 3E and 3F are respectively similar to FIGS. 3B and 3C, but illustrate another embodiment of the radially expandable seal.

FIG. 4A is a longitudinal cross-sectional view schematically illustrating a system in accordance with another embodiment for dislodging and removing a blood clot.

FIG. 4B is a view similar to FIG. 4A but illustrating a subsequent step in the method.

FIG. 5A is a longitudinal cross-sectional view schematically illustrating a system in accordance with another embodiment for dislodging and removing a blood clot.

FIG. 5B is a view similar to FIG. 5A but illustrating a subsequent step in the method.

FIG. 7A is a longitudinal cross-sectional view schematically illustrating another embodiment showing a system for dislodging and removing a blood clot.

FIG. 7B is a view similar to FIG. 7A but illustrating a subsequent step in the method.

FIG. 9A is a longitudinal cross-sectional view schematically illustrating another embodiment in the form of a system for dislodging and removing a blood clot.

FIG. 9B is a view similar to FIG. 9A but illustrating another subsequent step in the method.

FIG. 10A is a longitudinal cross-sectional view schematically illustrating another illustrative embodiment in the form of a system for dislodging and removing a blood clot.

FIG. 10B is a view similar to FIG. 10A but illustrating a subsequent step in the method.

FIG. 10C is a view similar to FIG. 10B but illustrating another subsequent step in the method.

FIG. 10D is a view similar to FIG. 10C but illustrating another subsequent step in the method.

FIG. 11A is a longitudinal cross-sectional view schematically illustrating another illustrative embodiment in the form of a system for dislodging and removing a blood clot.

FIG. 11B is a view similar to FIG. 11A but illustrating a subsequent step in the method.

FIG. 12A is a longitudinal cross-sectional view schematically illustrating another illustrative embodiment in the form of a system for dislodging and removing a blood clot.

FIG. 12B is a view similar to FIG. 12A but illustrating a subsequent step in the method.

FIG. 13A is a longitudinal cross-sectional view schematically illustrating another illustrative embodiment in the form of a system for dislodging and removing a blood clot.

FIG. 13B is a view similar to FIG. 13A but illustrating a subsequent step in the method.

FIG. 13C is a view similar to FIG. 13B but illustrating another subsequent step in the method.

FIG. 13D is a view similar to FIG. 13C but illustrating another subsequent step in the method.

FIG. 14A is a longitudinal cross-sectional view schematically illustrating another illustrative embodiment in the form of a system for dislodging and removing a blood clot.

FIG. 14B is a view similar to FIG. 14A but illustrating a subsequent step in the method.

FIG. 16A is a longitudinal cross-sectional view schematically illustrating another illustrative embodiment of a blood clot removal or extraction system.

FIG. 16B is a view similar to FIG. 16A but illustrating a subsequent step in the method.

FIG. 17A is a longitudinal cross-sectional view schematically illustrating another illustrative embodiment of a blood clot removal or extraction system.

FIG. 17B is a view similar to FIG. 17A but illustrating a subsequent step in the method.

FIG. 19A is a longitudinal cross-sectional view illustrating another embodiment of an elongate intravascular element and radially expandable seal or blood clot extraction element.

FIG. 19B is a side elevation illustrating full deployment of the radially expandable element shown in FIG. 19A.

FIG. 19C is a longitudinal cross-sectional view schematically illustrating the device of FIGS. 19A and 19B being used to dislodge and remove a blood clot.

FIG. 20A is a longitudinal cross-sectional view schematically illustrating another illustrative embodiment of a blood clot dislodging and removal element being used to extract a blood clot.

FIG. 20B is a view similar to FIG. 20A but illustrating a subsequent step in the method.

FIG. 21A is a longitudinal cross-sectional view schematically illustrating another illustrative embodiment of a blood clot dislodging and removal element being used to extract a blood clot.

FIG. 21B is a view similar to FIG. 21A but illustrating a subsequent step in the method.

FIG. 22A is a longitudinal cross-sectional view schematically illustrating another illustrative embodiment of a blood clot dislodging and removal element being used to extract a blood clot.

FIG. 22B is a view similar to FIG. 22A but illustrating a subsequent step in the method.

FIG. 24A is a longitudinal cross-sectional view schematically illustrating another illustrative embodiment of a blood clot dislodging and removal element being used to extract a blood clot.

FIG. 24B is a view similar to FIG. 24A but illustrating a subsequent step in the method.

FIG. 25A is a longitudinal cross-sectional view schematically illustrating another embodiment of an elongate intravascular element being used to extract and remove a blood clot.

FIG. 25B is a view similar to FIG. 25A but illustrating a subsequent step in the method.

FIG. 26A is a longitudinal cross-sectional view schematically illustrating another embodiment of an elongate intravascular element being used to extract and remove a blood clot.

FIG. 26B is a view similar to FIG. 25A but illustrating a subsequent step in the method.

FIG. 28C is a view similar to FIG. 28B but illustrating a subsequent step in the method.

FIG. 28D is a view similar to FIG. 28C but illustrating a subsequent step in the method.

FIG. 29A is a longitudinal cross-sectional view schematically illustrating another embodiment of an elongate intravascular element being used to extract and remove a blood clot.

FIG. 29B is a view similar to FIG. 29A but illustrating a subsequent step in the method.

DESCRIPTION OF ILLUSTRATIVE EMBODIMENTS

The detailed description herein serves to describe non-limiting embodiments or examples involving various inventive concepts and uses reference numbers for ease of understanding these examples. Common reference numbers between the figures refer to common features and structure having the same or similar functions, as will be understood. While various figures will have common reference numbers referring to such common features and structure, for purposes of conciseness, later figure descriptions will not necessarily repeat a discussion of these features and structure.

Figure 1A:
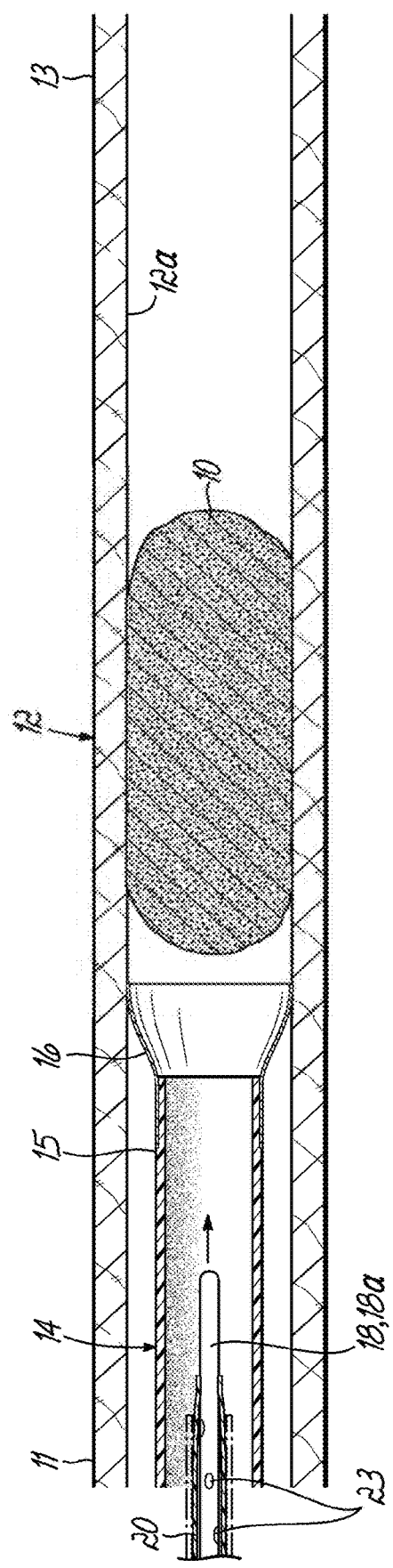
FIG. 1A is a longitudinal cross-sectional view schematically illustrating a system in accordance with one illustrative embodiment being used to dislodge and remove a blood clot.
Figure 1B:
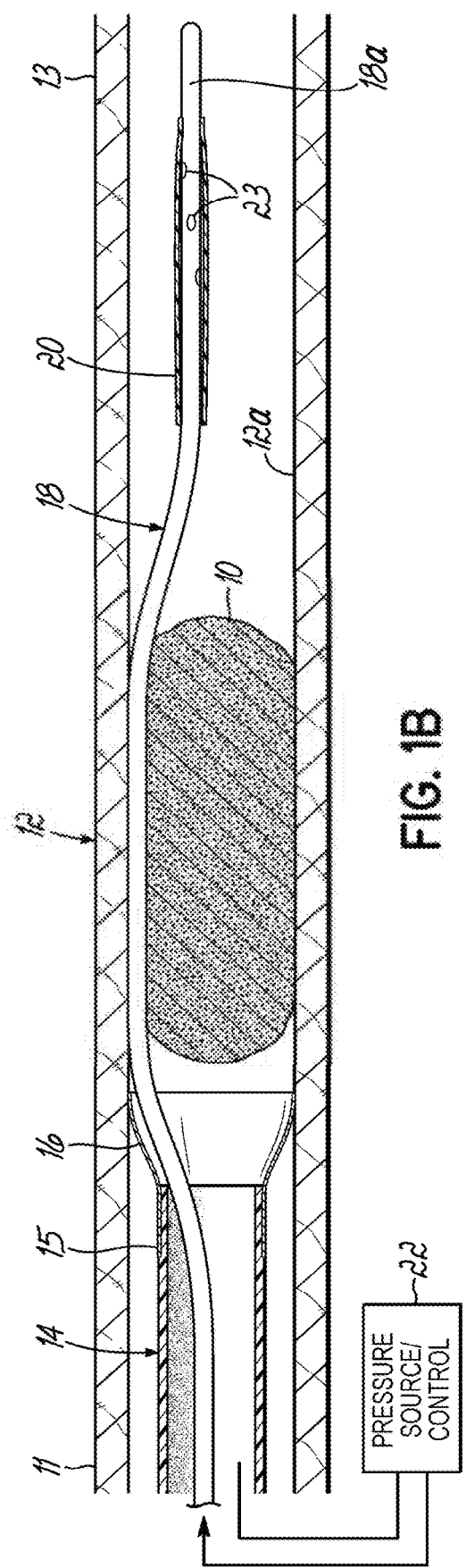
FIG. 1B is a view similar to FIG. 1A but illustrating a subsequent step in the method of dislodgement and removal of the blood clot.

FIGS. 1A and 1B

FIGS. 1A and 1B illustrate an obstruction or blood clot 10 in a blood vessel 12 having an interior wall surface 12a. The blood vessel 12 can comprise a proximal portion 11 and a distal portion 13, and can contain the blood clot 10 in the vessel between the portions 11, 13. As used herein, the term "blood clot" means any obstruction or clot material impeding the flow of blood in the vessel 12 regardless of the material forming the obstruction. An illustrative embodiment or example of a clot removal system is shown and includes an elongate intravascular element in the form of a suction catheter 14. The suction catheter 14 can comprise a distal end 15, which in turn can comprise a mouth or seal 16. The distal end 15 of the suction catheter 14 is circular. The mouth or seal 16 can be funnel-shaped and radially expandable by having a stent-like structure which can self-expand upon being directed out from a delivery catheter (not shown). During an operation to remove the blood clot 10, a user inserts the distal end 15 of the suction catheter in its unexpanded form into the blood vessel 12 through the proximal portion 11. The mouth or seal 16 can be expanded radially to contact the interior wall 12a of the blood vessel 12 and create a seal against fluid flow at the proximal side of the blood clot 10. Next, a guidewire 18 can be passed through the length of the suction catheter 14 out of the mouth or seal 16 and directed distally beyond the clot 10 (FIG. 1B). The guidewire 18 can comprise a thin and radially expandable distal seal membrane 20 at its distal end portion 18a. The guidewire 18 can comprise a wire core that is made of a small hollow tube with one or more slots or slits (not shown) cut into at least the distal end portion 18a to allow the guidewire 18 to bend or flex easily. The hollow tube can also contain a solid core wire that fills the lumen or void of the tube. In some embodiments, the wire core can be solid but flexible, and wrapped around helically by thin, flexible wire. The guidewire 18 can comprise a U-shaped tip (not shown) that also has an internal wire with wraps of wire surrounding it. This prevents the distal tip 18a of the guidewire 18 from penetrating through the wall of the vessel 12. In some embodiments, the hollow guidewire 18 is not filled with a solid core wire but, instead, is open to allow transmission of fluid, such as $CO_2$, to create a change in pressure within the blood vessel 12. In some embodiments, the outer surface of the guidewire 18 can be coated with a low friction material that helps in directing the wire and avoiding clotting.

FIG. 1C

Figure 1C:
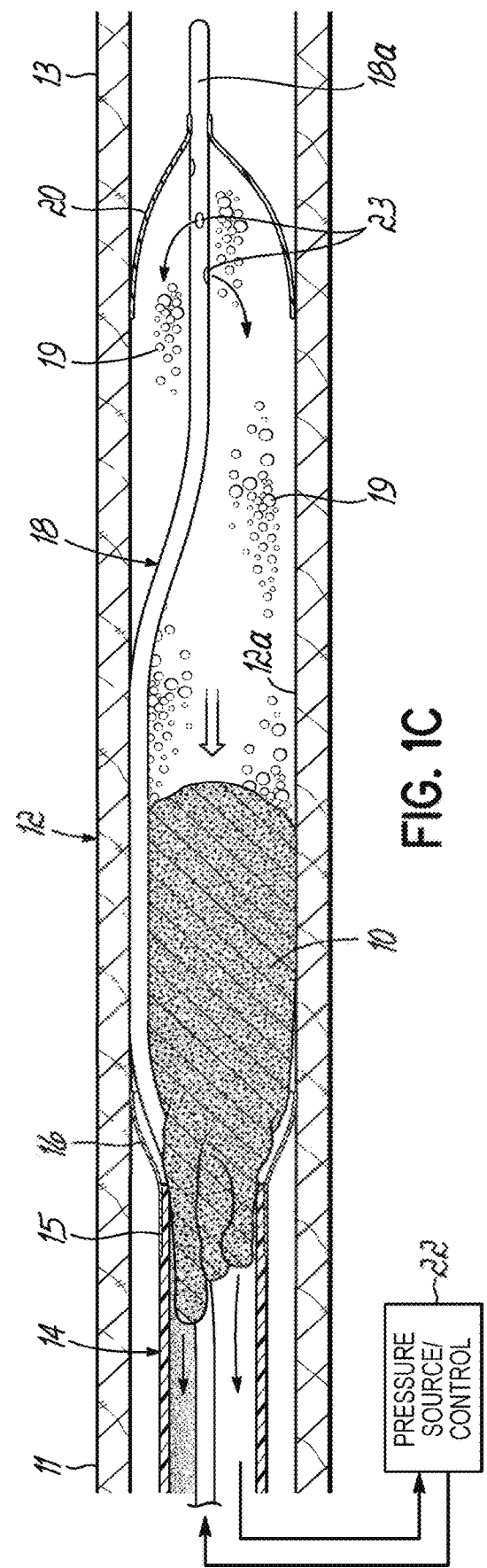
FIG. 1C is a view similar to FIG. 1B a but illustrating a subsequent step in the method.

As shown in FIG. 1C, a system can comprise a guidewire 18 connected to a pressure source 22. The guidewire 18 can be passed through a mouth 16 of a suction catheter 14 and stopped on a distal side of a blood clot 10. The mouth or seal 16 can be expanded to create a seal against a blood vessel wall at a proximal side of the blood clot 10. The guidewire 18 can comprise a distal seal or membrane 20, and perforations 23 of any desired number, shape and/or configuration at its distal end portion 18a. For example, the perforations 23 can be substituted by one or more slits or slots in the guidewire distal end portion 18a within the inflation or expansion area of the seal 20. The perforations 23 are located proximal to the attachment point of the distal seal 20 to the guidewire 18 or other elongate intravascular element. The seal 20 can comprise many embodiments. In some embodiments, the distal seal or membrane can be expanded radially to create a seal at the distal side of the blood clot 10. The proximal end of the seal can be open to the blood clot 10.

A pressure source 22 can release $CO_2$ 19 out of the perforations 23 on guidewire to positively pressurize the distal seal or membrane 20 by pressure on the distal side of the clot 10. Applying positive pressure instead of suction within a vessel 12 may avoid collapse of the vessel 12 and allow easier removal of blood clots 10. Applying positive pressure within the vessel 12 distal to the clot 10 can radially expand the vessel 12, free the clot 10 from its lodged location against the interior wall surface 12a of the vessel 12, and force the clot 10 in a proximal direction back to the suction catheter 14 which can provide relative negative pressure at its own funnel-shaped distal end 16.

One or more pressure sources and controls 22 are provided, such as schematically shown in FIG. 1C for providing and controlling the suction and/or positive fluid pressure provided as disclosed herein and/or providing other control and operational functions. Although the pressure source/control 22 is not illustrated in every embodiment, for conciseness, it will be appreciated that every embodiment of system disclosed herein preferably includes components for providing negative and/or positive pressure and one or more controls 22 associated with the source (e.g., one or more pumps), and/or associated with the elongate intravascular element (e.g., a catheter and/or guidewire) delivering the pressure. The control 22 may also provide other capabilities. Vessels that are ischemic may be prone to spasm. Positive fluid pressure may help to expand the vessel 12 and improve the chance of clot removal. Pressurizing the blood vessel 12 distal to the clot 10, and suctioning or aspirating the blood clot 10 proximal to the clot 10 may be a successful combination of actions to remove a clot 10—as a large pressure gradient can be produced.

As used herein, the term "fluid" means a liquid, a gas, or a combination of liquid and gas. Liquids may be any desired biocompatible liquid. Gas such as air, $CO_2$, $O_2$, an anesthetic gas or any other biocompatible gas can be used and may provide protection against brain injury. $CO_2$ is absorbed very rapidly inside the body and may be a very good gas to use for pressurization. $CO_2$ can be nontoxic and is often available in hospitals in tanks and/or in other gas supplies. It can also be generated locally by adding an acid to bicarbonate. Nitric oxide is a powerful vasodilator gas. It may be useful to pressurize and physically and chemically dilate blood vessels. Aerosolized drugs can also be delivered. These could be used to dilate the vessel 12 and protect the brain. Fluids with medications could also be directed into the vessel 12, such as in the examples shown and/or otherwise described herein.

The distal guidewire membrane 20 seals anywhere along its length generally, but is open at its proximal end in this embodiment. The gas or other fluid such as delivered through perforations 23 may be continuous (constant) or pulsed (cycled) at one or more desired frequencies and amplitudes of pressure, such as controlled by the pressure source/control 22. The fluid pressure may be directed slowly to avoid vessel over-distention and rupture. Slow pressurization can avoid these undesirable effects. The pressure will generally be equal at the opposite ends of the guidewire 18 so adding gas or fluid slowly should be safe. The fluid should distend or radially expand the vessel 12 at the location of the applied pressure, thereby assisting to free or at least loosen the clot 10 from the vessel wall surface 12a, and force the clot 10 in a proximal direction back to the suction catheter 14 which is providing relative negative pressure at its own funnel-shaped distal end 16. One or both of the suction and positive fluid pressure levels and/or type (e.g., constant pressure and/or pulsed or cycled pressure) may be adjusted during the procedure as desired or deemed necessary by the physician or in accordance with an algorithm.

FIG. 1D

Figure 1D:
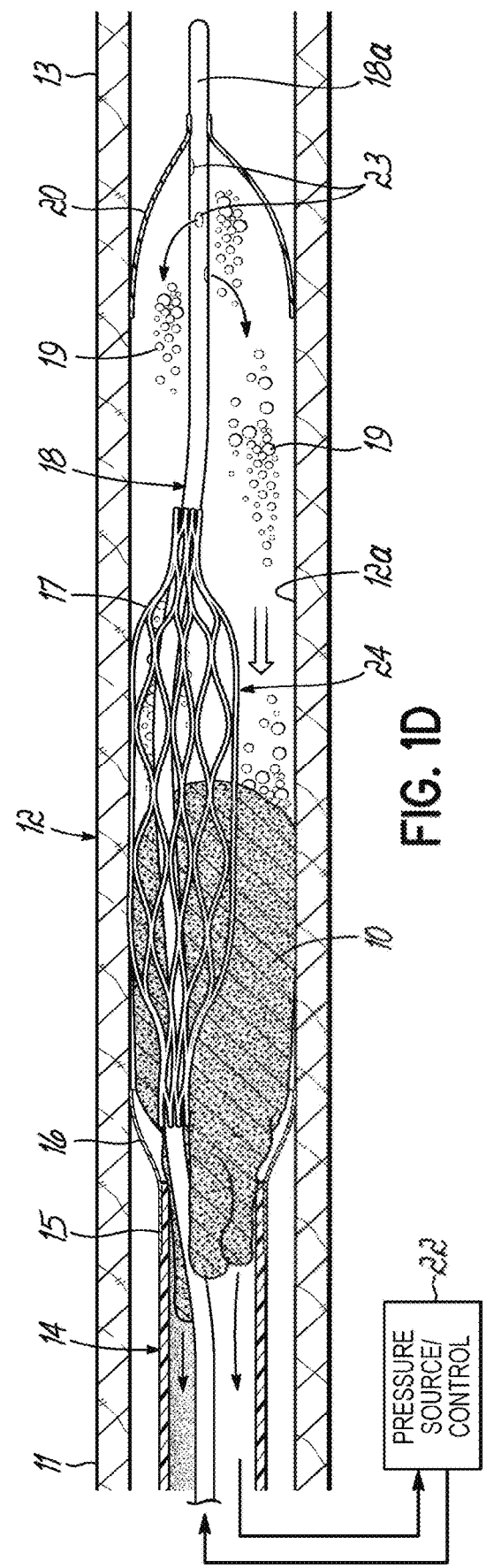
FIG. 1D is a view similar to FIG. 1C but illustrating the optional use of a stent-like retrieval device for removing the blood clot.

FIG. 1D illustrates removal of a blood clot 10 from a blood vessel 12 with a system comprising a stent-triever 24. In some embodiments, the system can further comprise a pressure source 22 that provides a positive pressure in addition to a negative pressure or suction provided by the catheter 14. In certain embodiments, the pressure source may not provide a positive pressure. The stent-triever 24 can comprise a guidewire 18 and a mesh 17 proximal to the distal end of the guidewire 18. When deployed, the guidewire 18 can be passed through the catheter 14 to the distal side of the blood clot 10 and the mesh 17 can be located near the site of clot 10. When the pressure source 22 applies suction through the catheter 14 to dislodge the blood clot 10, the mesh 17 can physically trap the blood clot 10, allowing for easier removal. In some embodiments, a positive pressure can be applied from a pressure source 22 through guidewire 18 to help in dislodging the blood clot 10. The guidewire 18 can further comprise a seal 20. The seal 20 can comprise many embodiments. In some embodiments, the seal can be proximally open-ended and flexible. The seal can be expanded to help protect against broken pieces of clot 10 or emboli traveling distally, such as into the brain of the patient.

Figure 2C:
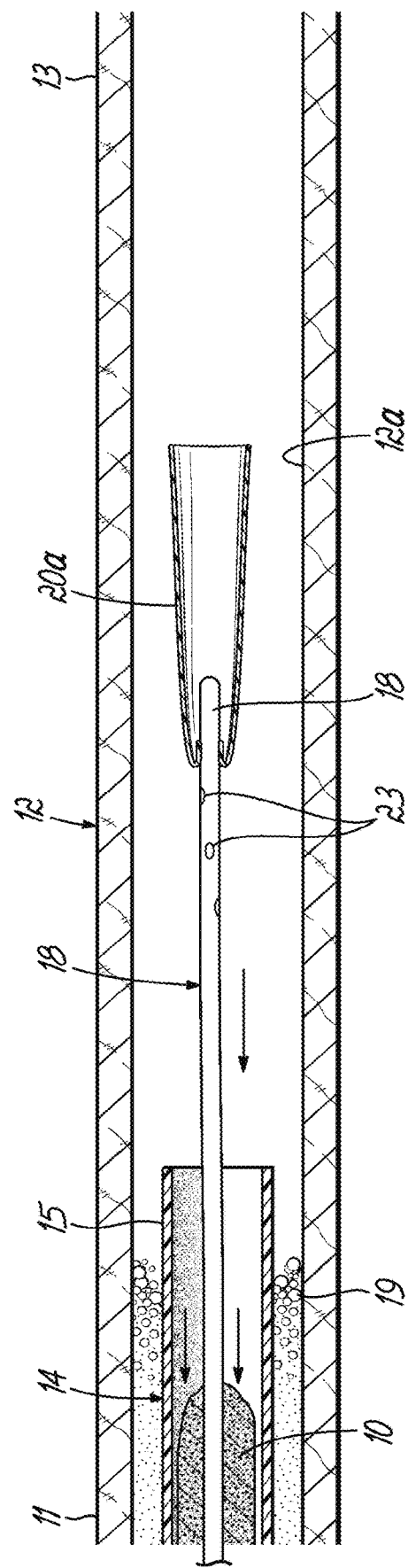
FIG. 2C is a view similar to FIG. 2B but illustrating the withdrawal of the elongate intravascular element at the end of the procedure.

FIGS. 2A, 2B and 2C

Here, a balloon-shaped or more spherical radially expandable seal 20a is shown with an annular hole or aperture 21 at its proximal end. The balloon membrane 20a or seal may have one hole or multiple holes 21, especially proximally. The end of the membrane 20a near the perforations 23 may expand first (for example, by being more compliant) and the other, more proximal portion with the hole 21 may expand at a later time or subsequently. The balloon-shaped membrane 20a can seal the blood vessel 12 where the contacts the vessel wall surface 12a (FIG. 2B). The membrane 20a can help to prevent broken pieces of blood clot 10 from traveling distally. Suction is applied through the catheter 14 to dislodge and remove the blood clot 10. As a user removes guidewire 18 after the procedure, the membrane 20a may invert such that the membrane may or may not contact the interior wall 12a of blood vessel, allowing for easier removal of the guidewire 18 (FIG. 2C).

FIGS. 3A and 3B

These figures illustrate that a distal seal or membrane 20b may be elongate or tubular so as to cover or overlap intersections or openings of side vessel branches 12b communicating with the main vessel 12 containing the clot 10. This keeps the fluid 19 from leaking out through side branches 12b and causing the main vessel 12 lose positive pressure. Shape variations for the distal seal 20b or membrane, such as generally cylindrical or other shapes, may provide additional assistance. Also, different thicknesses of the membrane 20b and differences in the flexibility or compliance may assist to ensure that the membrane 20b inflates near the fluid source hole or holes 23 first, and before the remainder of the membrane 20b inflates or expands.

Figure 3C:
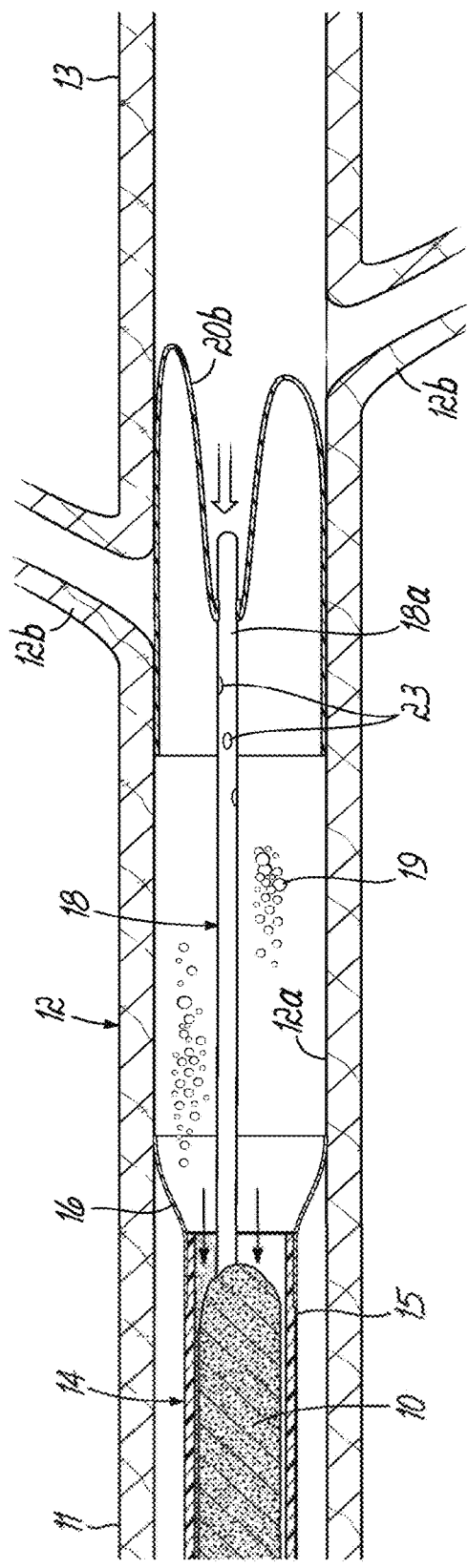
FIG. 3C is a view similar to FIG. 3A but illustrating a subsequent step in the method of dislodging and removing the blood clot.
Figure 3D:
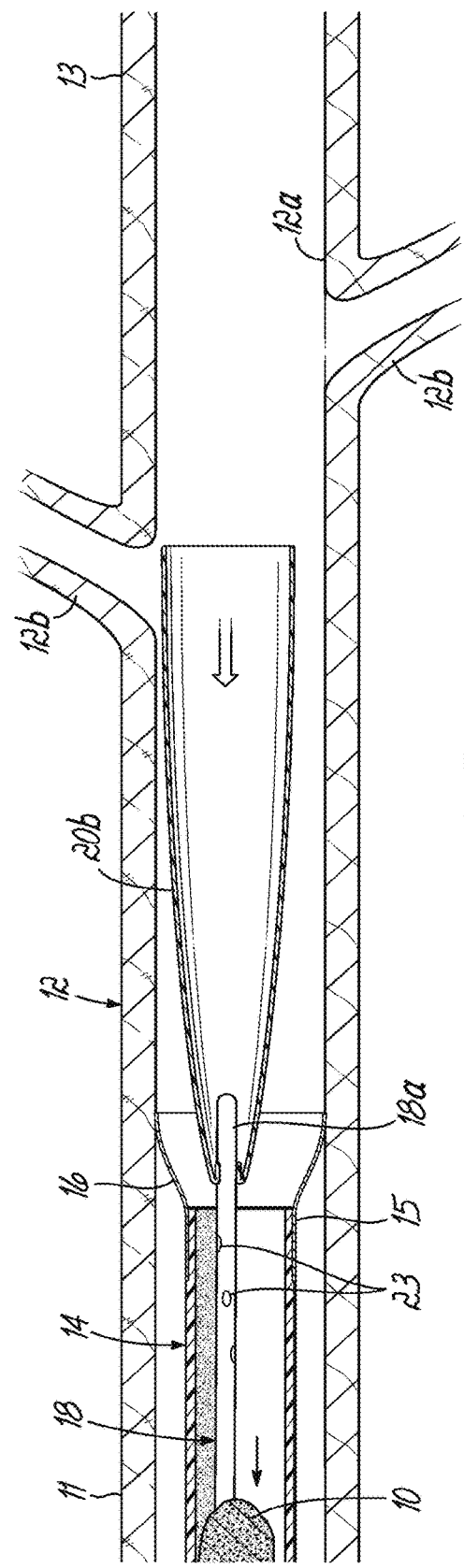
FIG. 3D is a view similar to FIG. 3C but illustrating a subsequent step including withdrawal of the elongate intravascular element at the end of the procedure.

FIGS. 3C and 3D

Here, the clot 10 is shown to be forced into the distal end of the suction catheter 14 for removal purposes. The membrane or seal 20b is allowed to depressurize and to invert for removal purposes. If the gas used for positive pressurization is $CO_2$, it should absorb in a short period of time. When the clot 10 is removed, there is no longer a closed space around the membrane 20b and the gas or other fluid may escape. Imaging of the clot 10 is useful, with $CO_2$, for example, on one side of the clot 10 and dye on the other, as $CO_2$ can be seen on X-ray as a lucent area. This may highlight the distal end of the clot 10, and dye shows the proximal end.

FIG. 3E

Here, the inflating or expanding distal membrane 20c is shown as an elongate tube also acting as a piston against a distal end of the clot 10. For example, a tubular membrane 20c that sequentially inflates in a direction toward the clot 10 (proximally) and pushes the clot 10 in a proximal direction toward the suction catheter 14 may be used. This is better illustrated and described below. The membrane or seal 20c may be fashioned to impact the clot 10 in a manner similar to a piston. The open, proximal end of the seal 20c is attached to the guidewire 18 by one or more tethers 25.

FIG. 3F

As shown in this figure, the membrane 20c may not invert for removal purposes. Here, the tethers 25 allow the seal 20c to be pulled into the suction catheter 14 in a proximal direction. A noninverting membrane may be beneficial as it can continue to prevent migration of clot material downstream into the brain vessels even during removal.

FIG. 3G

Here, the proximal, open end 27 of a radially expandable distal seal 20d is oriented generally at an acute angle to the longitudinal axis of the elongate intravascular element e.g., guidewire 18. In other words, the proximal, open end 27 is bevel shaped. The bevel shape may be a linear or straight cut end, or it may be of any curved or other shape. The radially expandable seal or tubular element 20*d* in this embodiment, is shown as attached to the elongate intravascular element guidewire 18 by a single tether 25. Optionally, multiple tethers 25 may be used. In either case, the tether(s) 25 may be integrally formed with the membrane or seal 20*d*, or may be separate and then suitably attached to the seal 20*d* and to the elongate intravascular element or guidewire 18, such as with adhesive. The elongate tubular seal 20*d* may be formed by cutting a tube to form an opening at the proximal end 27 of a desired shape. The tubular seal may comprise a suitable flexible frame, such as formed by super-elastic wire elements (e.g., see FIG. 3H). This would assist with support and self-adjusted expansion in a radial direction to accommodate different sized blood vessels 12. The generally bevel-shaped proximal end 27 assists with automatically collapsing and withdrawing the seal/tube 20*d* into the catheter 14 at the end of the procedure.

FIG. 3H

Figure 3G:
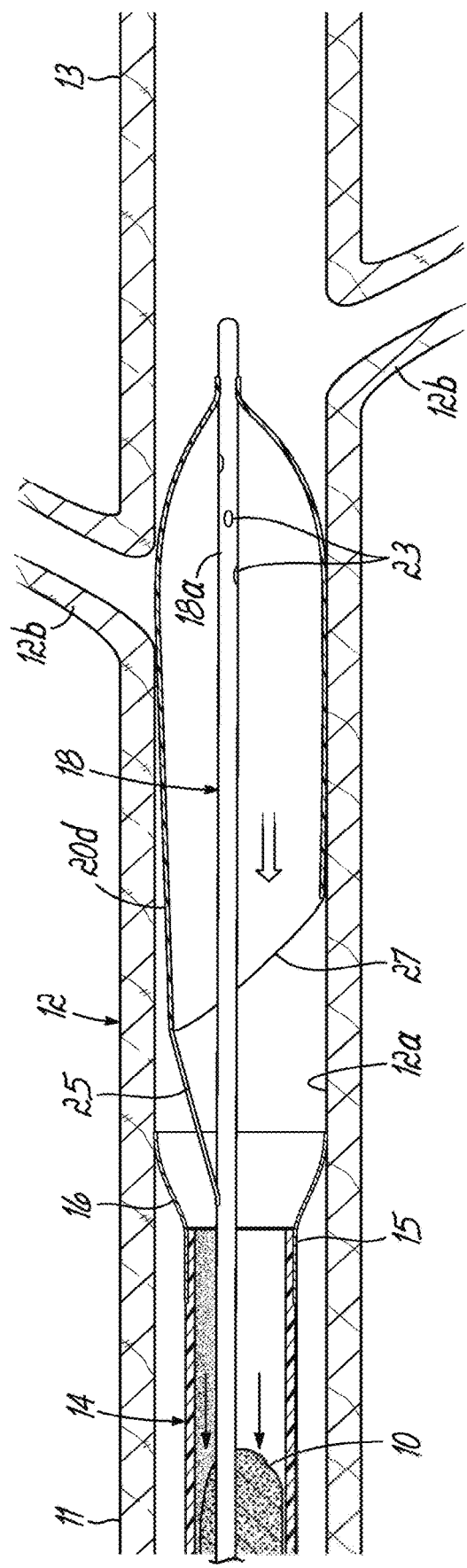
FIG. 3G is a view similar to FIG. 3E but illustrating another embodiment of the system.
Figure 3H:
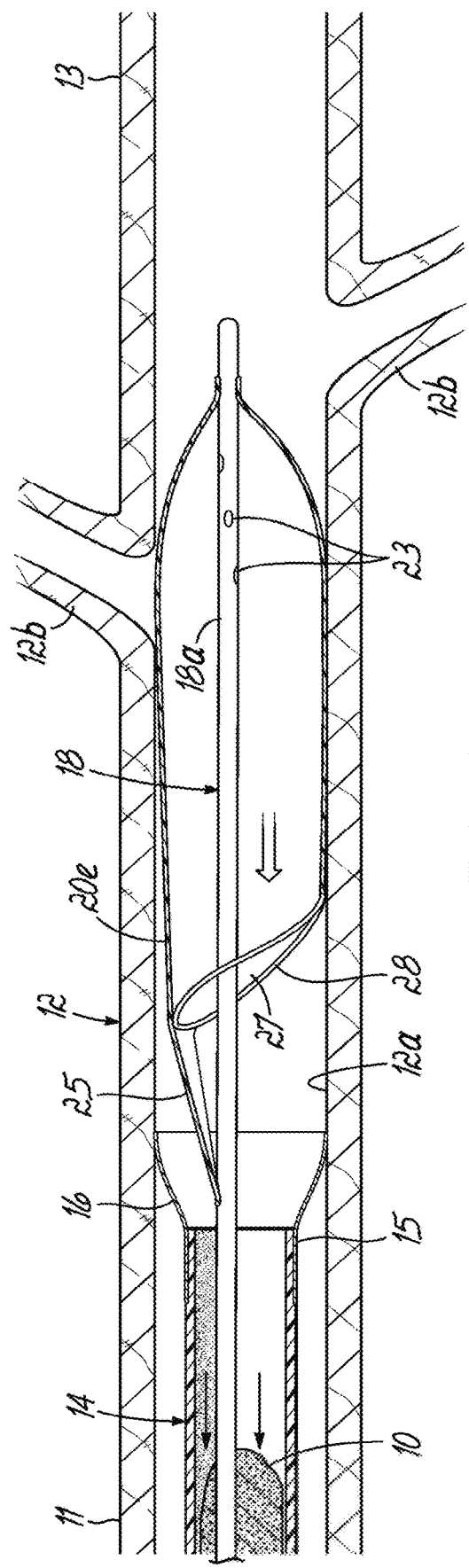
FIG. 3H is a view similar to FIG. 3G but illustrating another embodiment of the system.

In this embodiment, as generally mentioned with respect to FIG. 3G, the open proximal end 27 has a generally beveled shape, but the shape is curvilinear or sigmoid. The tether 25 is integrally formed from the seal/20*e* during manufacture to simplify the manufacturing process. In addition, a flexible frame is provided for the seal/tube structure 20*e* and includes a ring-shaped support element 28 affixed at the open, proximal end 27. The ring-shaped structure 28 may be formed from a super-elastic wire, for example. When the ring-shaped wire 28 sits in a vessel 12 having the typical circular cross-sectional shape, it will be oriented obliquely where its diameter is greater than the internal diameter of the vessel 12. However, as the vessel internal diameter increases, the wire 28 will re-orient itself to be less oblique and maintain engagement with the internal wall surface 12*a* of the vessel 12. The reverse will occur as the vessel diameter decreases. This results in a self-adjusting size feature for the distal seal 20*e*.

FIGS. 4A and 4B

Here, a double membrane 20*f* is shown and occludes the vessel 12 sequentially. For example, there may be a first, more spherical distal balloon section 20*f*1 and then a second, elongate tubular or generally cylindrical proximal section 20*f*2 that expands due to the introduction of fluid through perforations 23. Other shapes may be used for a "piston effect" to remove the clot 10.

Figure 5C:
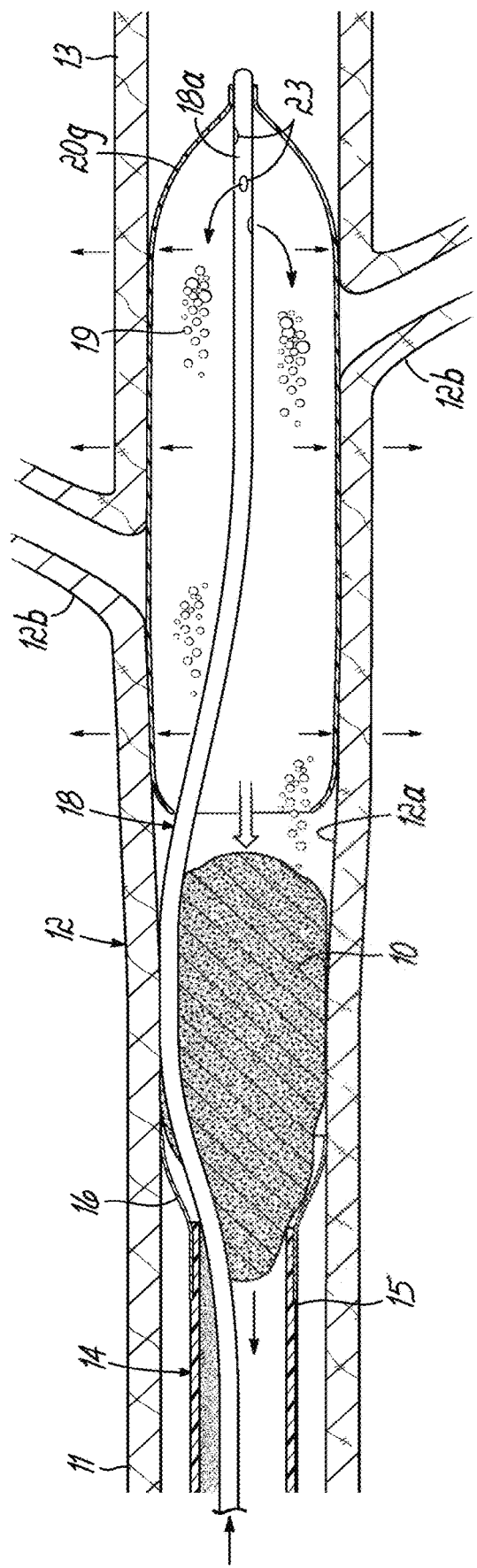
FIG. 5C is a view similar to FIG. 5A but illustrating a subsequent step in the method.

FIGS. 5A, 5B and 5C

These figures illustrate that the balloon or membrane seal 20*g* may unravel at its open proximal end so that it is used as a "piston." The unravelling may be variable. The length of the clot 10 generally is unknown and, therefore, as the guidewire 18 passes distally beyond the clot 10 the unraveling balloon may expand to adjust the distance to the clot 10.

Figure 6A:
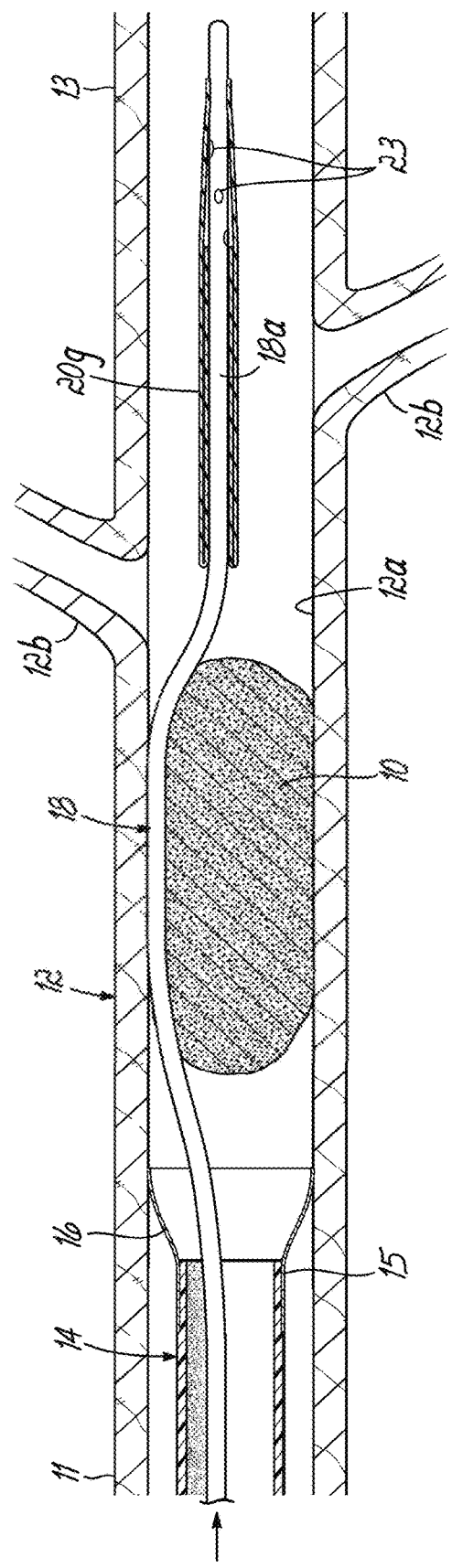
FIG. 6A is a longitudinal cross-sectional view schematically illustrating another embodiment showing a system for dislodging and removing a blood clot.
Figure 6B:
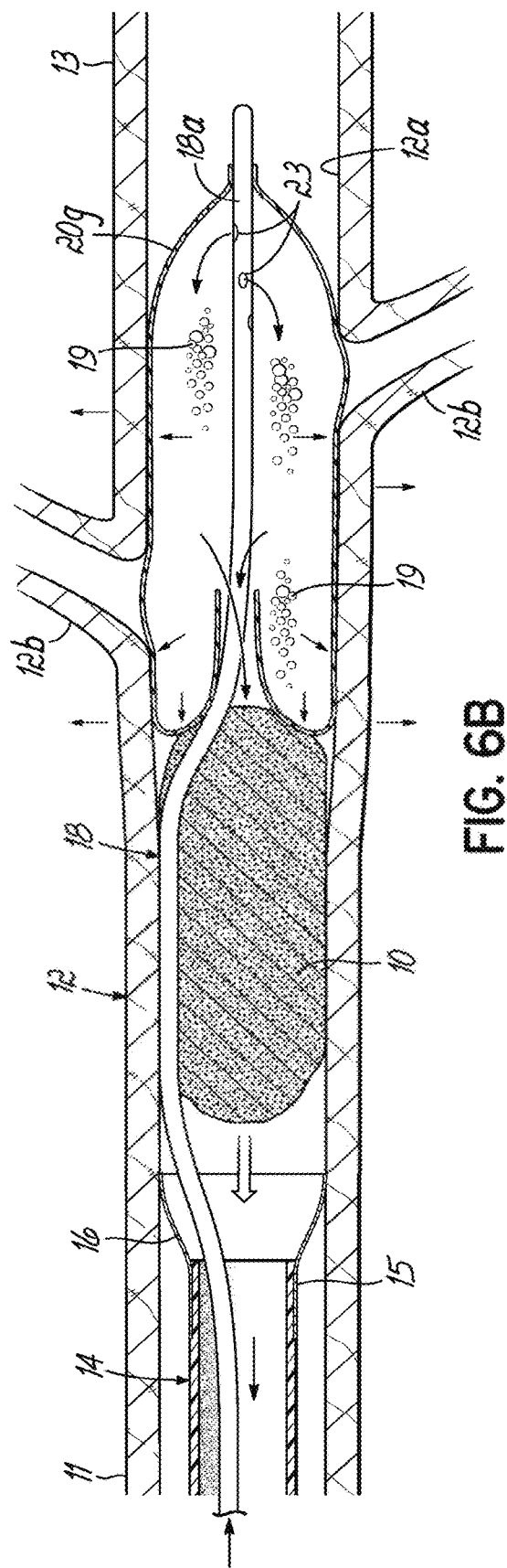
FIG. 6B is a view similar to FIG. 6A but illustrating a subsequent step in the method.

FIGS. 6A and 6B

FIGS. 6A and 6B show another embodiment of the tubular, distal seal 20 that can be unfolded or unrolled in a proximal direction. The folded seal may be expanded in a proximal direction as the guidewire 18 passes distally beyond the clot 10, so that one or more unravelling proximal end portions of the seal 20*g* can contact the blood clot 10, forcing the clot 10 in a proximal direction to assist with dislodgement and/or removal.

FIGS. 7A, 7B, 7C and 7D

Figure 7C:
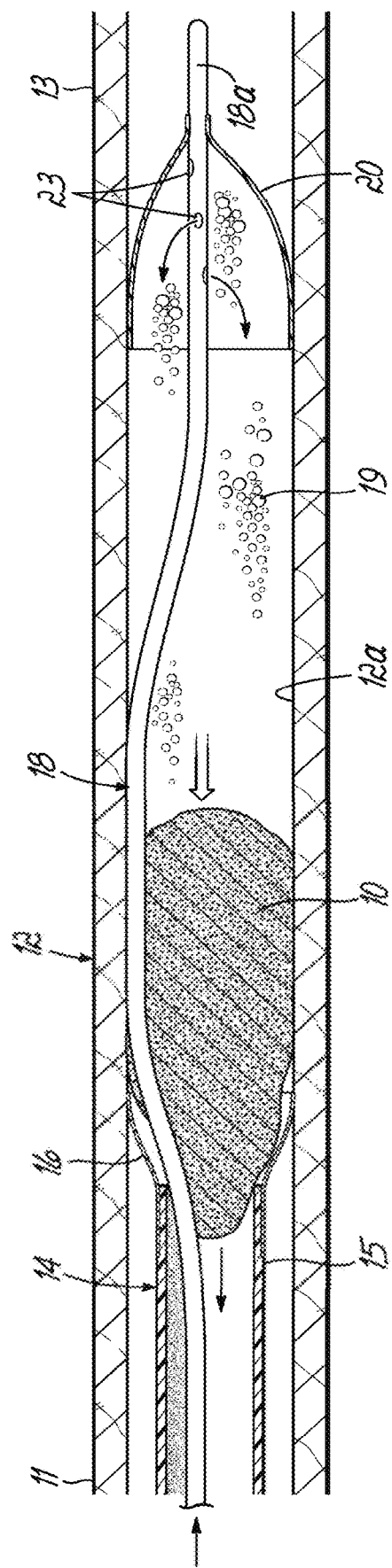
FIG. 7C is a view similar to FIG. 7B but illustrating a subsequent step in the method.
Figure 7D:
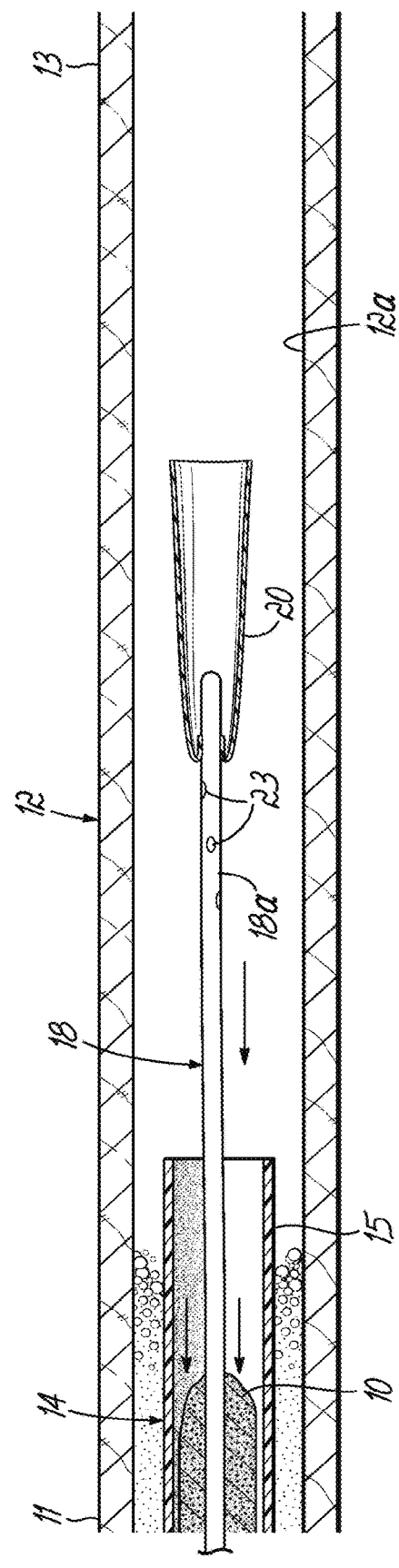
FIG. 7D is a view similar to FIG. 7C but illustrating a subsequent step in the method including withdrawal of the elongate intravascular element.

Guidewire 18 may comprise a tip that bends into a J-shape. This is to avoid puncturing a vessel 12 as the distal end of the guidewire 18 is directed through the vessel 12 or vessel structures of the patient. However, the guidewire 18 must pass around the clot 10. Sometimes, the physician cannot pass the wire distally beyond the clot 10 as blood flow forced the clot 10 farther and farther into a tapering vessel lumen. The vessel 12 may also go into spasm. Therefore, it would be useful to be able to stabilize and guide a guidewire 18 to allow it to be directed more accurately between the vessel wall surface 12*a* and the clot 10 when that clot 10 is tightly fitted into the vessel 12. This embodiment provides a guide 30, which may be either a mechanical device or a balloon-type structure, or a combination of both, at the distal end of the suction catheter 14 to help guide the wire past the clot 10. The guidewire 18 and guide 26 can both be positioned within the catheter 14 with the guidewire 18 passing between the catheter and the guide 30 (FIG. 7B). The guide 30 includes a guide portion that may be a channel 32 for receiving and steering the guidewire 18 in a sideward direction toward a periphery of the clot 10. The guide 30 further includes an inflatable portion 34 that is inflated for use as shown, and deflated for delivery and removal through catheter 14. FIGS. 7C and 7D respectively illustrate positive pressure pushing and negative pressure suctioning of the clot 10 into the distal end of the suction catheter 14, and then subsequent removal of the clot 10 and distal seal 20 or membrane through the suction catheter 14.

Figure 7F:
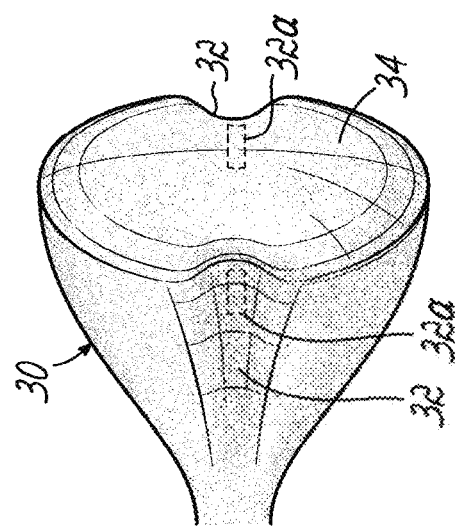
FIG. 7F is a perspective view of the guide illustrated in FIG. 7E.
Figure 7E:
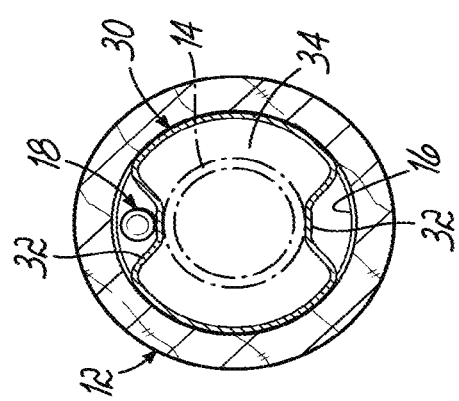
FIG. 7E is a cross-sectional view taken along line 7E-7E of FIG. 7B.

FIGS. 7E and 7F

These views better illustrate the use of a guide 30. The guide 30 may be passed through the suction catheter 14 in a deflated state, then inflated for use at the site of the clot 10, and then deflated again and removed. The guide 30 may straighten the U-shaped or J-shaped distal end of the guidewire 18 and brings it directly adjacent the clot 10 so that the distal end of the guidewire 18 can find the space between the clot 10 and the interior wall surface 12*a* of the vessel 12. The channel 32, or other guide portion such as an indentation, may be used to help steer the guidewire past the clot 10. This may be used when the guidewire 18 will not pass through the clot 10 or between the clot 10 and the vessel wall surface 12*a*, or it may be used in every case.

Figure 8A:
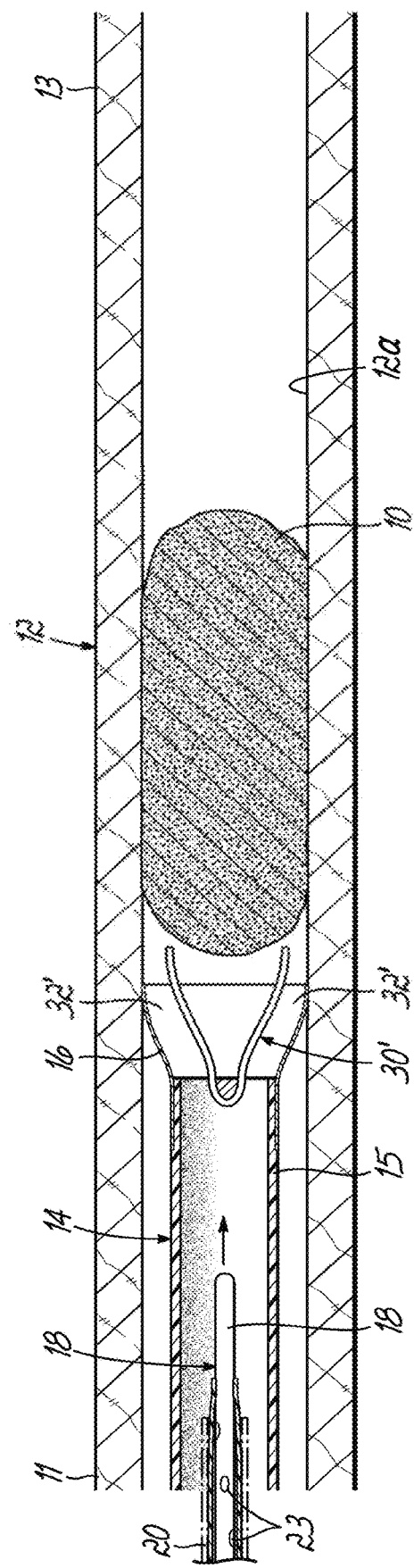
FIG. 8A is a longitudinal cross-sectional view schematically illustrating another embodiment in the form of a system for dislodging and removing a blood clot.
Figure 8B:
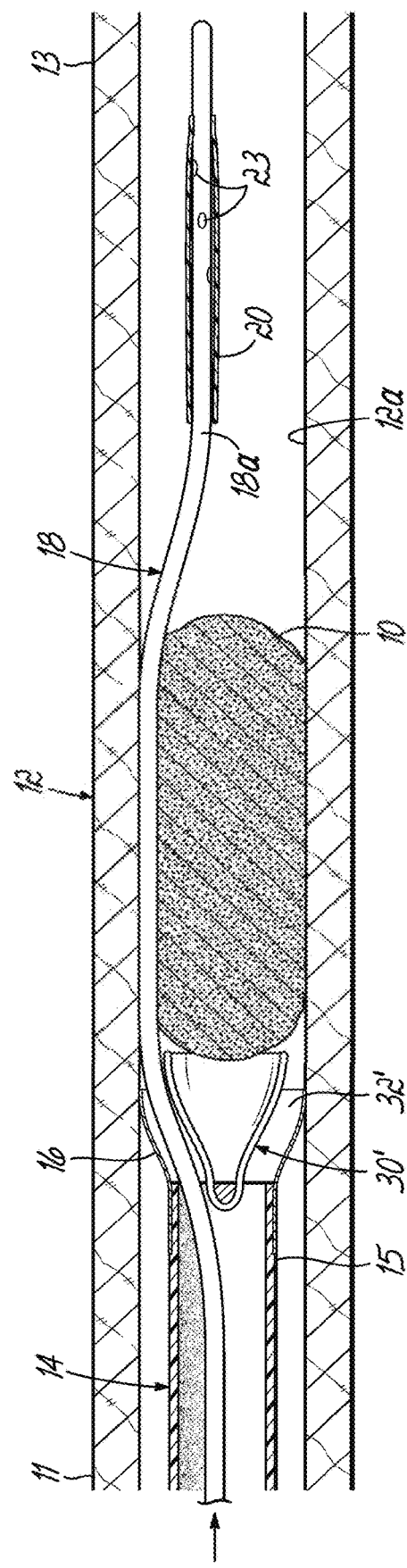
FIG. 8B is a view similar to FIG. 8A but illustrating another subsequent step in the method.
Figure 8C:
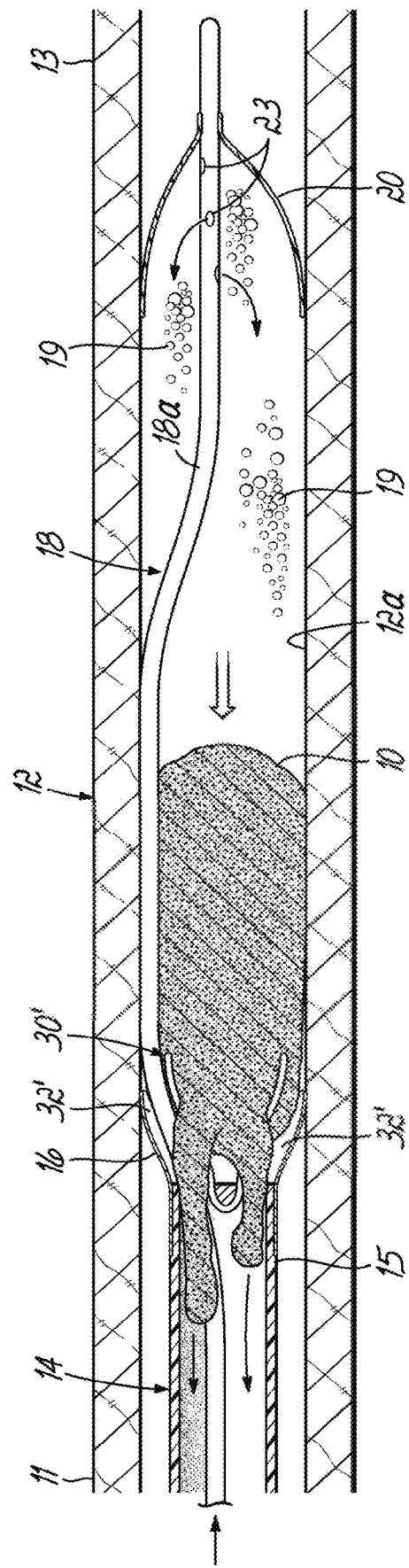
FIG. 8C is a view similar to FIG. 8B but illustrating another subsequent step in the method.

FIGS. 8A, 8B and 8C

These figures illustrate the use of an alternative guide 30', having a guide channel 32' defined by rails or other structure, for receiving and steering an elongate intravascular element in the form of a distal guidewire 18. The guide 30' would be best removed before suction is applied by the catheter 14 as it may otherwise block the effects of the suction. The guide 30' may be mechanically collapsible for suitable delivery and removal through the catheter. The guide 30' may use the funnel-shaped seal 16 as a part of the channel 32'.

FIG. 9A

The previous figures show an elongate intravascular element in the form of a guidewire 18 with a distal membrane added to provide a seal of various desirable but merely illustrative forms. The distal ends of the seal can be attached to the microcatheter 26 while the proximal ends are left unattached such that when the membrane is expanded, it can be partially open through the unattached ends. Guidewires are generally constructed with steel and it may be difficult to reliably make holes in the side of the guidewire 18 to deliver fluid. It may be more useful to construct one or more systems generally described above from a catheter in place of or in addition to a guidewire 18.

A catheter is generally made from a polymeric material. This would better allow suitable fluid apertures to be formed in the wall of the catheter. The catheter also generally has a larger diameter than a guidewire 18, but catheters are routinely directed alongside and past clots when stent-trievers 24 are delivered through the catheters.

Figure 9C:
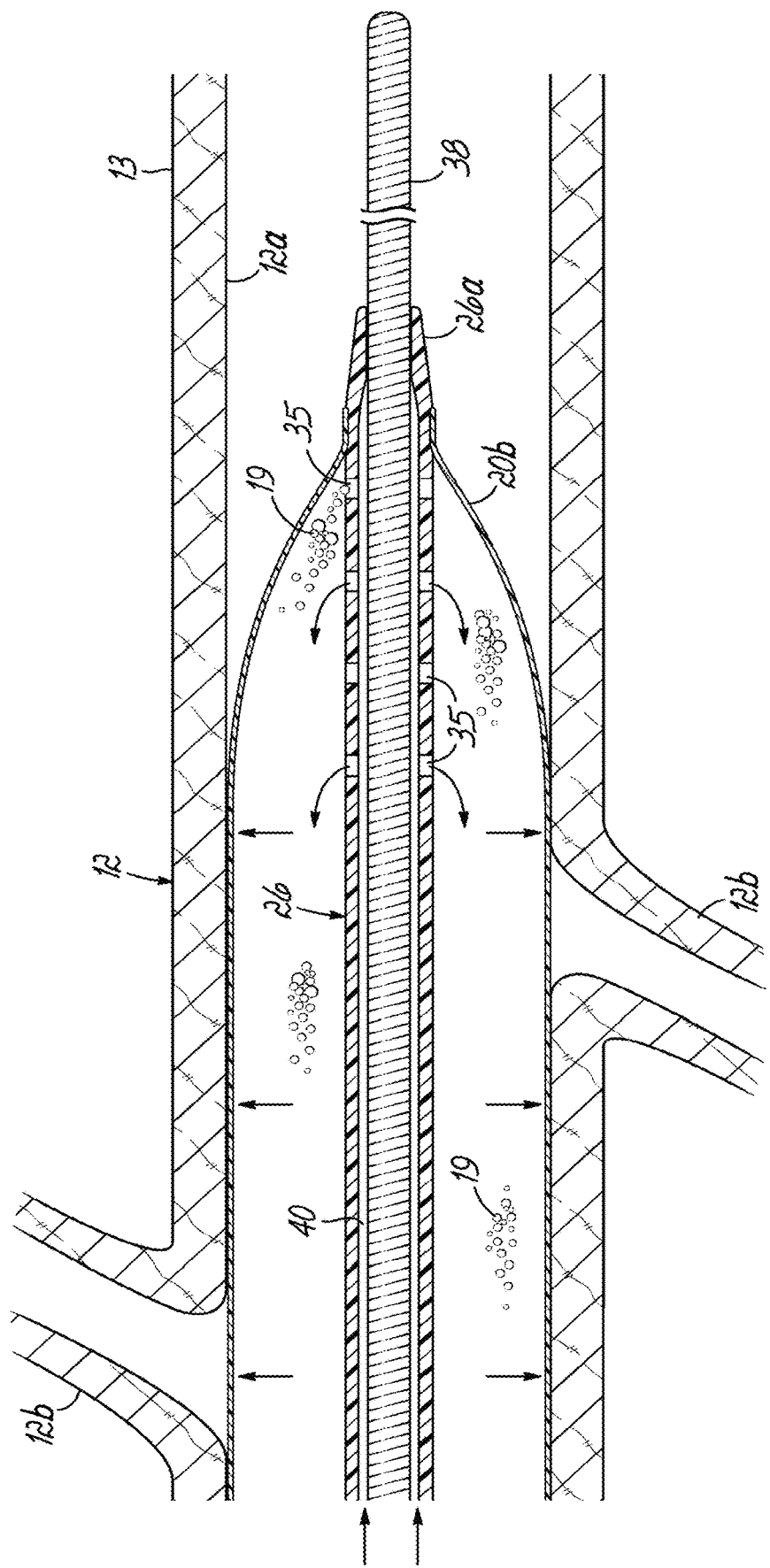
FIG. 9C is a view similar to FIG. 9B but is an enlarged view showing another embodiment.
Figure 10E:
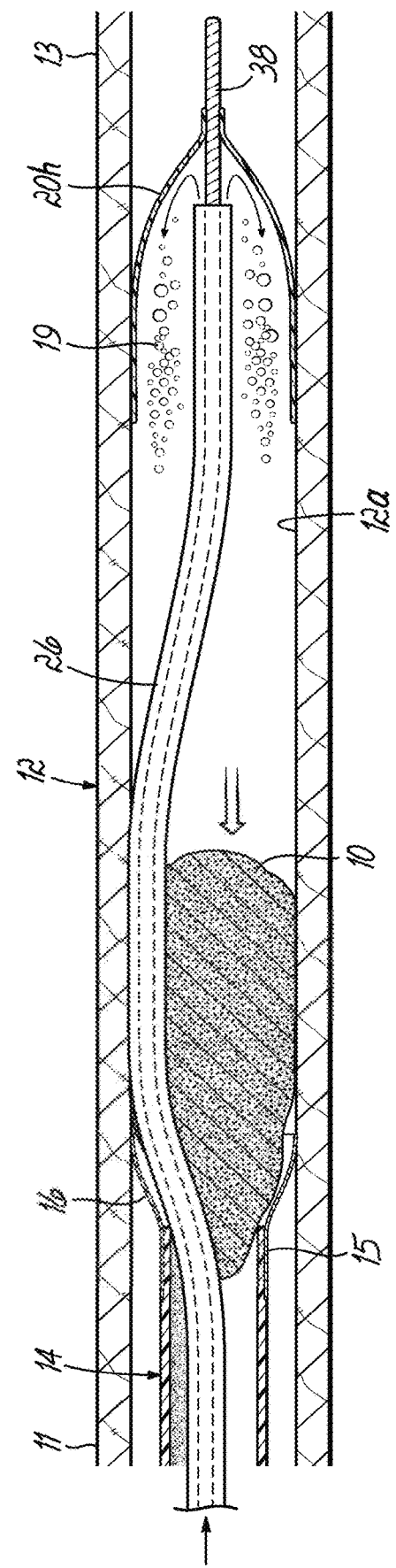
FIG. 10E is a view similar to FIG. 10D but illustrating another subsequent step in the method.
Figure 12C:
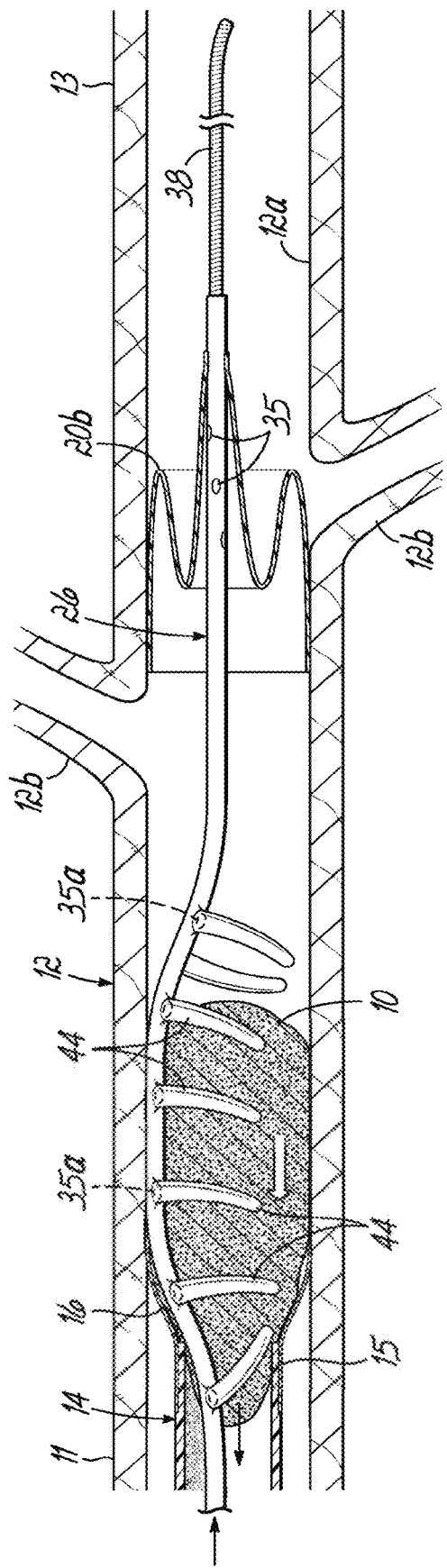
FIG. 12C is a view similar to FIG. 12B but illustrating another subsequent step in the method.
Figure 12D:
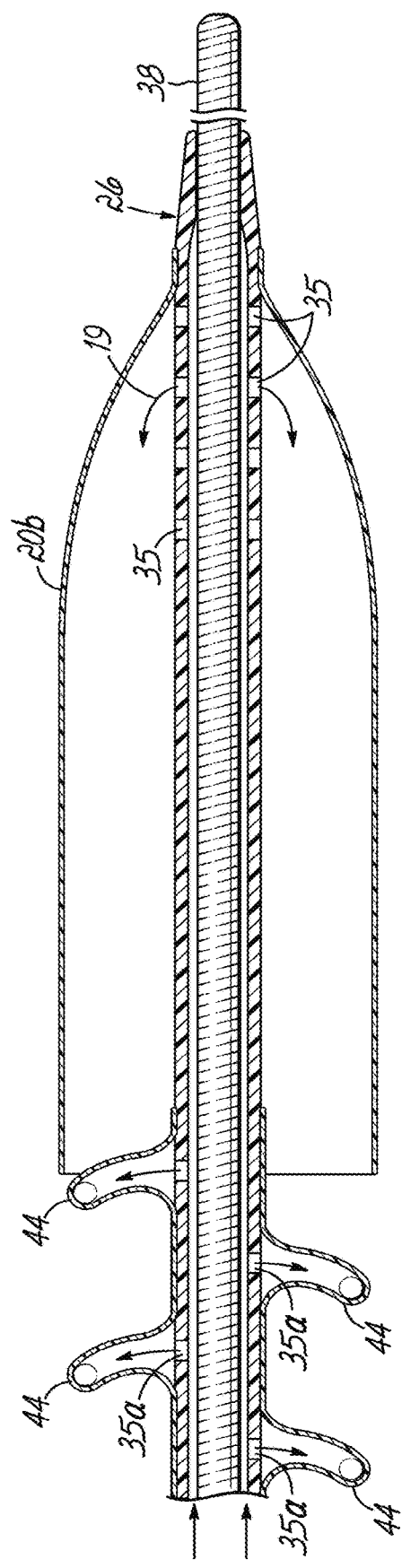
FIG. 12D is an enlarged cross-sectional view showing the system of FIGS. 12A through 12C.
Figure 14C:
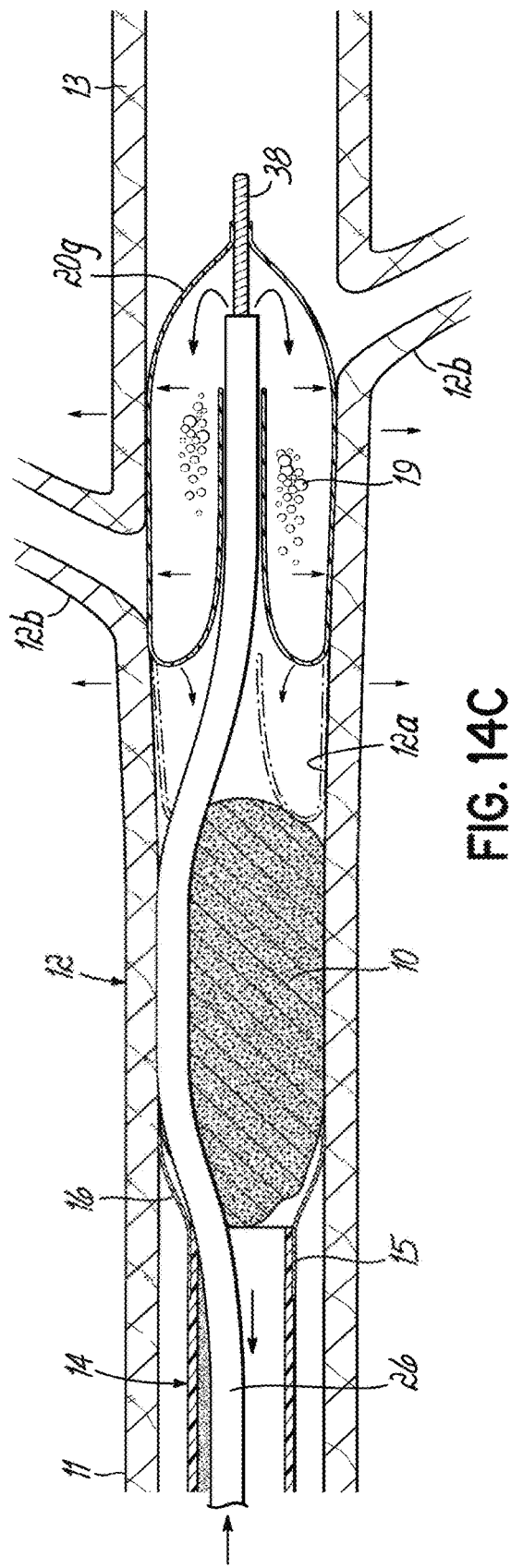
FIG. 14C is a view similar to FIG. 14B but illustrating another subsequent step in the method.
Figure 14D:
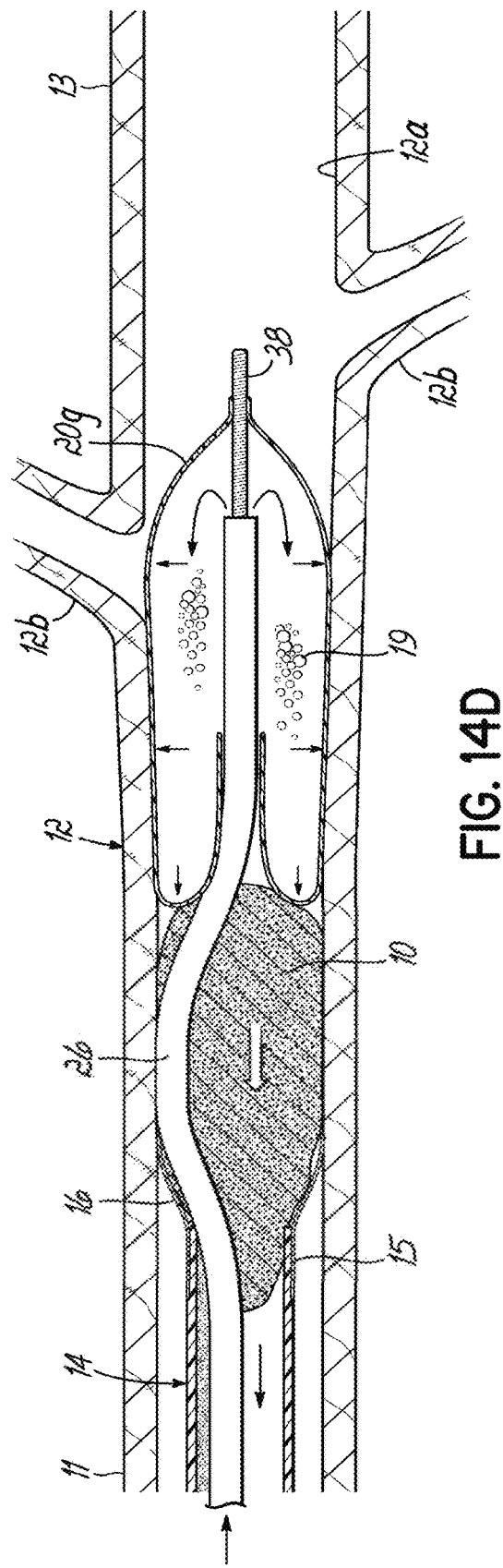
FIG. 14D is a view similar to FIG. 14C but illustrating another subsequent step in the method.
Figure 15:
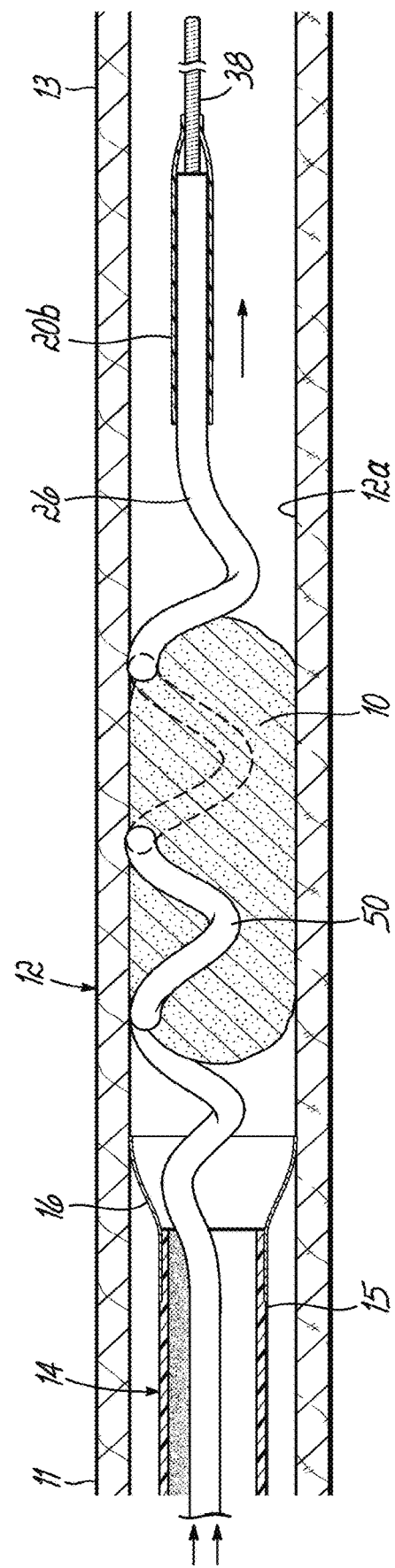
FIG. 15 is a longitudinal cross-sectional view schematically illustrating another illustrative embodiment of a blood clot removal or extraction system.

FIG. 9A shows a microcatheter 26 with a radially expandable seal membrane 20b attached at its distal end portion. It will be appreciated that any other configuration of the seal 20b may be used instead. There are holes or apertures 35 in the microcatheter 26 under or within the area of the expanded membrane 20b to infuse fluid such as gas. FIG. 9A also shows that a small guidewire tip 36 extends beyond the distal end of the microcatheter 26 to help deliver the microcatheter 26 beyond the clot 10. This may be a guidewire portion suitably affixed to the distal end of the microcatheter, or may be the tip portion of a more conventional guidewire extending the length of the microcatheter 26. To avoid a "step up" at the junction of the guidewire tip with the catheter, there may need to be a filler placed at the junction such as a glue or polymer to smooth the transition. Also, the guidewire tip 36 and/or the microcatheter distal tip 26a could comprise tapers that are matched so there is a minimal transition. The microcatheter 26 is inserted and extends distally beyond the clot 10 as shown and described previously.

FIG. 9B

FIG. 9B shows that the microcatheter 26 has been passed distally beyond the clot 10. Fluid is infused through side holes 35 to expand the membrane 20b and create a seal against the interior wall surface 12a of the vessel 12 so that positive pressure can be applied in a proximal direction to extract the clot 10. The number of side holes 35 can be varied. Additional holes (not shown) can also be placed in the microcatheter 26 between the clot 10 and the vessel wall surface 12a to help liberate the clot 10 from a strong attachment to the vessel wall surface 12a. It may be useful to rotate the microcatheter 26 to help separate the clot 10 circumferentially so it is free for removal. To encourage the catheter 26 to encircle the clot 10 when it is turned, the catheter 26 could be made with a gentle spiral or turn or a bend along its length. Vibration applied to the catheter 26 may assist clot separation. Oscillation of the pressure and fluid infusion may help to separate the clot 10 from the vessel wall surface 12a. Positive pressure is applied distal to the clot 10 (such as gas infusion shown by arrows) and suction is applied through the suction catheter 14 (vacuum). The clot 10 can then be removed. As described previously, variations and oscillations (i.e., cycling or pulsing the pressure) in the pressure (positive pressure and/or suction) on each side of the clot 10 may be useful in removing the clot 10.

FIG. 9C

This figure shows a device similar to the one shown in FIGS. 9A and 9B. This microcatheter 26 has a guidewire 38 is passed through the length of the device. The guidewire 38 also serves to seal the distal end 26a of the catheter 26 so that positive pressure can be developed inside the catheter 26 to pressurize the seal membrane 20b. There is space 40 between the guidewire 38 and the inside of the catheter 26 to inject fluid such as gas to expand and pressurize the membrane 20b. The infused gas presses the radially expandable membrane 20b against the vessel wall surface 12a to create a seal and allow pressure to be generated to push the clot 10 proximally. In performing the procedure, the guidewire 38 first could be directed distally beyond the clot 10. The catheter 26 could then be fed over the guidewire 38 distally beyond the clot 10. Gas could then be infused as shown and described at the location distal to the clot 10.

FIG. 10A

Construction of a system to remove clot 10 in which a guidewire type element or a catheter type element is part of the system could be difficult, expensive and perhaps unstable in some situations. As an option, the elongate intravascular element could be a standard microcatheter 26 and the lumen of the standard microcatheter 26 could be used as a flow channel to inflate or radially expand a distal seal or membrane 20h and positively pressurize the area between the 20h and the clot 10. It may be less expensive and easier to attach a membrane 20h to a guidewire 18 and pass this beyond the clot 10. This would be a relatively simple device to create. A relatively cylindrical seal or membrane 20h could be attached to a guidewire 18 near its distal tip and sealed to guidewire 38. The guidewire 38 with the attached membrane 20h is contained and delivered from inside a microcatheter 26, as shown in this figure. The guidewire 38 and microcatheter 26 are further contained and delivered from inside the suction catheter 14 and proximal to the clot 10. It will be appreciated that any other suitable delivery component(s) and method may be used instead for inserting and operating the microcatheter 26.

FIG. 10B

This figure shows the guidewire 38 (with attached seal or membrane 20h) inside the microcatheter 26. These devices have been directed distally beyond the clot 10. The membrane 20h is inside the microcatheter 26 during the delivery to make it easy to insert distally beyond the clot 10.

FIG. 10C

The guidewire 38 with the attached seal or membrane 20h is pushed out of the microcatheter 26 at a location distal to the clot 10. The membrane 20h is fashioned so that its open, proximal end is stiffer than its distal end and springs radially outward or open once outside of the microcatheter 26. To encourage the proximal end of the membrane 20h to open, a tiny super-elastic spring element (not shown) could be attached to the proximal end of the membrane 20h to help it maintain the shape shown in the figure. Previous figures shown and described herein have shown tethers 25 that are used to close the membrane 20h, and these could be used in this embodiment as well. The tether(s) 25 could be stiff and made of fine wires that are pushed or otherwise moved to open the membrane 20h.

FIG. 10D

The microcatheter 26 is then pushed toward the end of the guidewire 38 under the membrane or seal 20h to further open the seal into engagement with the interior wall surface 12a of the vessel 12.

FIG. 10E

Fluid, such as $CO_2$ gas or another fluid, is then injected through the microcatheter 26 and out the distal end thereof to more fully expand the membrane 20h in a radial direction to form a fluid seal between the membrane 20h and the interior wall surface 12a, and positively pressurize the area distal to the clot 10. There is enough space between the wire 38 and the inside of the catheter 26 to inject gas or other fluid. The advantage of this alternative is that no side holes are needed in a catheter or guidewire. A guidewire 3 can be made with an attached membrane or seal 20h as shown in the figures. The membrane 20h can be compressed and folded to deliver it from inside the microcatheter 26.

FIG. 11A

In this figure an alternative way of deploying the membrane or seal 20 is shown. The system comprises a guidewire 18 with an attached membrane 20 which is folded or collapsed on top of the microcatheter 26. The tip of the microcatheter 26 is advanced under the membrane 20 and close to the point of the attachment of the membrane 20 with the guidewire 38. At this point, the membrane 20 is located radially outside the microcatheter 26. The microcatheter 26 and the guidewire 38 are pushed distally beyond the clot 10. In a typical situation, there is an abrupt diameter change where the guidewire 38 passes through the microcatheter 26 and this can make directing the catheter 26 more difficult. The membrane or seal 20 is located to smooth the passage of the microcatheter 26 by covering this transition. An advantage to this arrangement is that the microcatheter 26 does not have to be advanced inside the seal or membrane 20. The membrane construction is more simple and the risk of the microcatheter 26 missing the inside of the membrane 20 to inflate the membrane 20 is eliminated.

FIG. 11B

This figure shows that gas or other fluid has been infused through the microcatheter 26. The gas comes out the distal tip 26a of the microcatheter 26 which is deep inside the membrane 20. This expands the membrane 20 and creates a distal seal 20. Pressure on the system then encourages the clot 10 to exit the vessel 12.

Once the membrane 20 is deployed by injecting $CO_2$ or other fluid, the microcatheter 26 may be moved toward the clot 10 and the tip of the microcatheter 26 may be brought back into the clot 10—between the clot 10 and the vessel wall surface 12a. $CO_2$ or other fluid may be injected to help separate the clot 10 from the vessel wall surface 12a. As explained previously, the $CO_2$ could be pulsed with oscillations in pressure to help detach the clot 10 from the vessel wall surface 12a. As with all other embodiments, the pressure could instead be constant or nearly constant, or a combination of pulsed and constant pressure may be used during different portions of the procedure. Also, vibration could be applied to the wire 38 or the catheter 26 to rapidly move the clot 10 and the vessel wall surface 12a and help to free the clot 10. The combination of fluid infusion, vibration and/or oscillation of pressure may be very useful.

As also discussed herein, positive pressure and suction can be provided proximal to the clot 10 through the suction catheter 14. Pulsations in the vacuum and positive pressure may enhance the effectiveness of this clot removal system. The microcatheter 26 and/or the guidewire 38 could comprise one or more steps. In this case, when the catheter 26 is rotated it would tend to encircle the clot 10 to separate it from the vessel wall surface 12a.

The microcatheter 26 could comprise oscillations also with a slightly serpentine shape or with U-shaped turns. The configuration would be designed generally to deviate from the line of the central axis of the catheter 26. For example, the deviations could alternate left and right or side-to-side similar to the teeth of a saw. The result would be to allow the microcatheter 26 to be rotated and/or otherwise moved relative to the clot 10 such that it helps separate the clot 10 from the vessel wall surface 12a by forcing the catheter 26 gradually between the clot 10 and the vessel wall surface 12a during rotation. An example is further discussed and shown herein.

The microcatheter 26 could also be moved back and forth over the clot 10 to help free or dislodge the clot 10. Combining negative or suction pressure, positive pressure, oscillation or pulsing of suction and/or positive pressure and/or vibration may be used. Also, rotation of one or more components around the clot 10 may help for the guidewire 38 or the catheter to travel around the circumference of the clot 10 and help to remove it.

A control 22 (such as illustrated in FIG. 1B) may be provided for various purposes with respect to any and/or all embodiments. For example, the control 22 may provide for pressure level changes, frequency and amplitude variations in the pulsing or and oscillations of pressure, type of pressure (suction and/or positive pressure), provision of vibrations and/or other aspects directly relevant to clot removal techniques. In addition or alternatively, the control 22 could measure blood loss to ensure that the patient does not lose too much blood during the procedure, and/or a control 22 could measure pressure in the system in order to monitor status of the clot 10. In this latter regard, zero pressure could indicate that the clot 10 is secured against the distal end of the suction catheter 14, while continuous suction pressure of a certain level may indicate that the clot 10 is traveling proximally through the suction catheter 14 during removal. The vibration could be applied to any device near the clot 10—the suction catheter 14, the microcatheter 26 and/or the guidewire 38.

$CO_2$ is absorbed rapidly. But it is possible that gas could remain under the membrane 20 where the gas does not contact tissue to absorb it. To remove the catheter system after clot removal, suction could be applied to the end of the microcatheter 26 to remove the gas under the membrane 20. This will flatten the membrane 20 and make removal easier. Suction can be applied to the microcatheter 26 of any of the described variations to help collapse the membrane 20 and remove it.

FIGS. 12A through 12D

These figures show side holes 35 in the microcatheter 26. The microcatheter 26 could be withdrawn proximally such that the side holes 35 are at the location of the clot 10. Or, the microcatheter 26 could be designed as shown in FIG. 12A such that proximal movement of the microcatheter 26 is not needed to align holes 35a with the clot location, e.g., between the clot 10 and the vessel wall surface 12a. This will allow for the infusion of gas or other fluid between the clot 10 and the vessel wall surface 12a.

As further shown in FIG. 12B, inflatable blades or fins 44 could be manufactured on the sides of the microcatheter 26. They could be inflated by additional side holes in the microcatheter 26 located under the fins or blades 44. These fins or blades could be made from small membranes that sit flat against the catheter 26 for insertion. The holes 35a could communicate with the holes 35 in the microcatheter 26 distally beyond the clot 10. When the distal holes 35 pressurize the area distally beyond the clot 10, the fins or blades 44 will begin to expand. The fins or blades 44 may be approximately 1 mm to 3 mm in size. The fins or blades 44 could be arranged like cleats on a shoe around the catheter 26. They could also form a structure such as a screw or helix that helps to engage the clot 10 and so the clot 10 can be pulled out proximally when the catheter 26 is pulled back. The fins or blades 44 could also be filled by a separate channel (not shown) so that they are not dependent or related to the use of holes 35 distally beyond the clot 10. The projections, such as fins or blades 44, may comprise any useful shape and the microcatheter 26 could help to trap clot 10. The projections 44 may also help to separate the clot 10 from the vessel wall surface 12a.

FIG. 13A

This figure shows a proximal seal membrane 16 that is delivered on the microcatheter 26. The microcatheter 26 sits inside the suction catheter 14. A wire 38 with a membrane 20g to seal distally has been passed beyond the clot 10. The membrane seal 20g may be expanded by a super-elastic frame that opens the seal. The membrane seal 20g could be expanded by positive pressure—by injecting fluid through the microcatheter 26. For delivery, the membrane 20g or seal could be inverted inside the microcatheter 26 and pushed out of the microcatheter 26 with a guidewire or stylet (not shown).

FIG. 13B

As shown in this figure, the proximal seal or membrane 16 has created a seal against the interior wall surface 12a of the vessel 12, such as previously shown and described.

FIG. 13C

As further shown in this figure, the distal seal 20g or membrane, as shown previously, is folded upon itself. As gas or other fluid is directed from inside the wire 38, the membrane 20g expands and begins to unroll. The membrane 20g eventually contacts the clot 10 and pushes the clot 10 in a proximal direction toward the suction catheter 14.

FIG. 13D

As shown, the clot 10 has been pushed into the receiving end of the proximal membrane 16. The proximal membrane 16 wraps around the clot 10 and helps to keep the clot 10 intact as it is pulled into the suction or vacuum catheter 14. This reduces the risk of clot break up and embolization of particles more distally in the brain. It could also be useful to have a longer proximal membrane 16. A clot 10 is often at least 10 mm in length. A membrane 16 that could fully contain the clot 10 and then sealed at the end by the unfolded distal seal membrane 20g would be completely contained and safe from embolization during removal.

FIG. 14A

As shown in this figure, the proximal seal 16 is attached to the suction catheter 14. It will be appreciated that the proximal seal or membrane 16 can take on many different shapes and sizes. For example, the proximal seal 16 could be longer than shown, and may be inverted inside the suction catheter 14 for delivery, and then pushed out for sealing. This figure also shows a clot 10 and a wire 38 carrying a distal membrane seal 20g before its deployment, e.g., rolled up or otherwise collapsed.

FIG. 14B

The proximal membrane seal 16 has been activated. Only a small amount of pressure may be needed to radially expand or unfurl this seal 16.

FIG. 14C

A microcatheter 26 has been advanced along the wire with the folded membrane 20g. $CO_2$ or other fluid may be used for inflation and the membrane 20g is expanded as shown.

FIG. 14D

As in the prior series 13 figures, the distal membrane 20g pushes the clot 10 into the proximal membrane 16 or at least toward the proximal membrane 16. Alternatively, the combined proximal suction force and distal pushing force can result in proximal movement of the clot 10. The clot 10 can then be removed.

There can also be positive pressure applied distal to the clot 10, i.e., in a proximal direction to help push the clot 10 in the proximal direction. The combination of positive pressure distal to the clot 10 and suction proximal to the clot 10 can also be very useful in clot extraction.

The suction and/or positive pressure can be altered, such as by being cycled or pulsed. The change in suction could be gentle or abrupt. It could be used in a repeated cycle or a variable cycle or any variation in suction and/or positive pressure that helps to dislodge clot 10. The suction and/or positive pressure may be applied in any pressure pattern. The positive pressure and suction can be adjusted simultaneously or as desired (cycles or pulses, pressure level or other variables) to produce the best arrangement to remove clot 10.

It can also be helpful to apply positive pressure both proximal and distal to the clot 10. This could help expand the vessel 12 and separate the clot 10 from the wall surface 12a of the vessel 12. Clot 10 inside a vessel 12 tends to become adherent to the vessel wall surface 12a. By stretching the vessel 12 with positive pressure, the vessel 12 can expand and at least part or even all of the clot 10 can be separated from the vessel wall surface 12a.

A device that is advanced down an existing or more conventional suction catheter that has a radially expandable seal such as the funnel-shaped distal end 16 shown, and helps to apply a seal at the end of the suction catheter 14 is advantageous. The funnel-shaped seal 16 could be made from shape memory or super-elastic material that collapses for insertion and opens for sealing. The shape memory or super-elastic material, such as NITINOL, may comprise a sealing membrane or cover material to produce a complete seal. The sealing material could be a plastic, such as ePTFE. A separate device like this would allow interventional radiologists and neurologists to use their existing suction catheters and then add the seal separately after the suction catheter 14 has been brought into place.

FIG. 15

This figure shows the microcatheter 26 with a non-linear section 50 which, in this illustrative embodiment, is spiral or helical shaped. Rotation of the microcatheter 26, such as while the microcatheter 26 is directed distally past the clot 10, can help disengage the clot 10 from the interior wall surface 12a of the vessel 12, making removal of the clot 10 easier.

FIG. 16A

Previous figures in the above-incorporated applications have shown inflatable or otherwise radially expandable membranes or seals 20 through 20g that provide a seal for positive pressurization at a location distal or beyond the clot 10 in a vessel 12. The distal membrane or seal can be delivered on an elongate intravascular element, such as a guidewire type structure or a catheter type structure.

As the distal membrane or seal is pressurized, one risk is that the fluid escapes distally and the seal fails to sufficiently form. A number of options to avoid this are described herein, such as double membranes, shaped membranes with a small proximal opening, etc.

Another option shown in this series of figures is to use the clot 10 to close the open proximal end of a distal membrane or seal 20i. Here, the membrane 20i is advanced so that the proximal (open) end of the membrane 20i is trapped between the interior vessel wall surface 12a and the clot 10. This closes the proximal end of the membrane 20i so that when it is inflated by fluid, the membrane 20i is guaranteed to expand and form a seal.

Figure 16C:
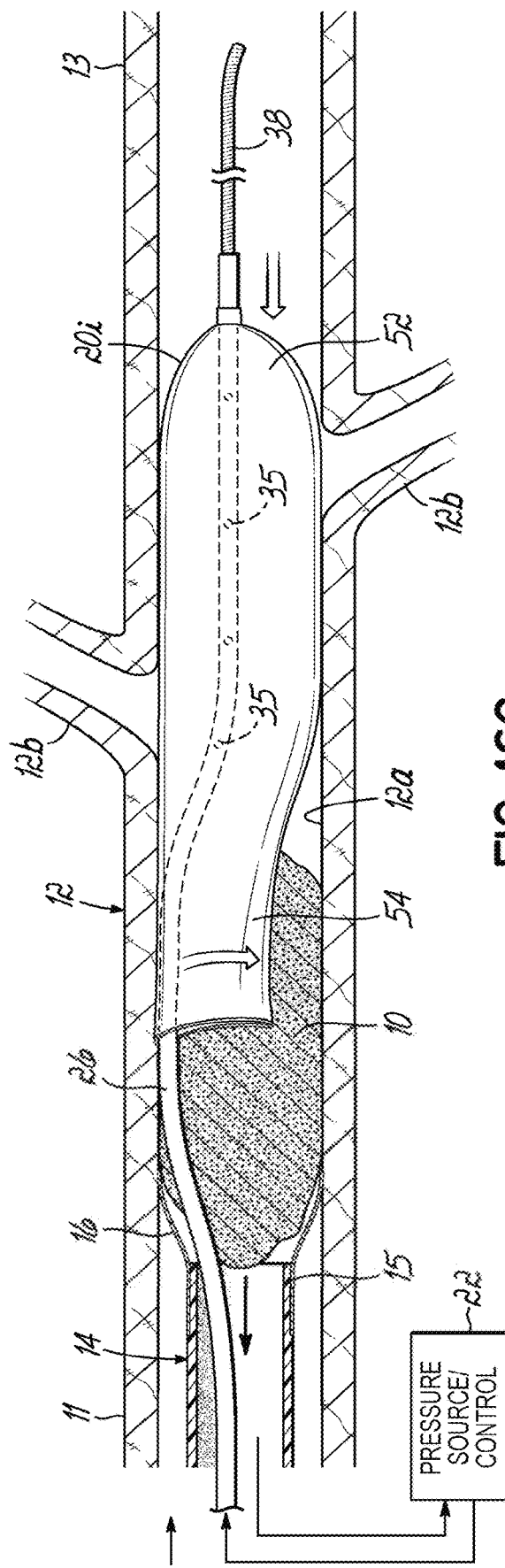
FIG. 16C is a view similar to FIG. 16B but illustrating a subsequent step in the method.
Figure 16F:
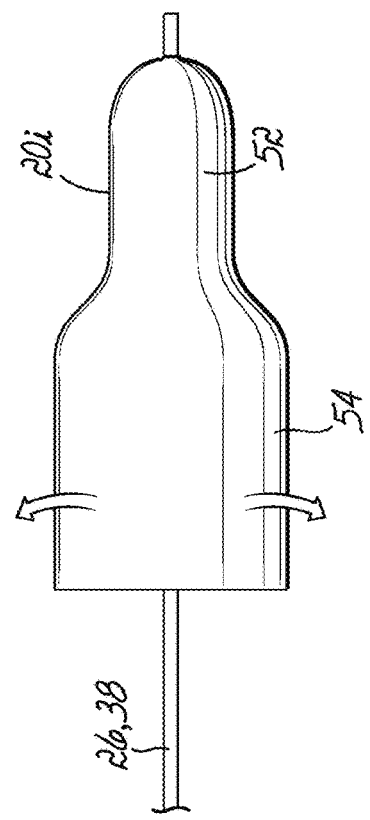
FIG. 16F is a side elevation of the radially expandable seal.
Figure 16E:
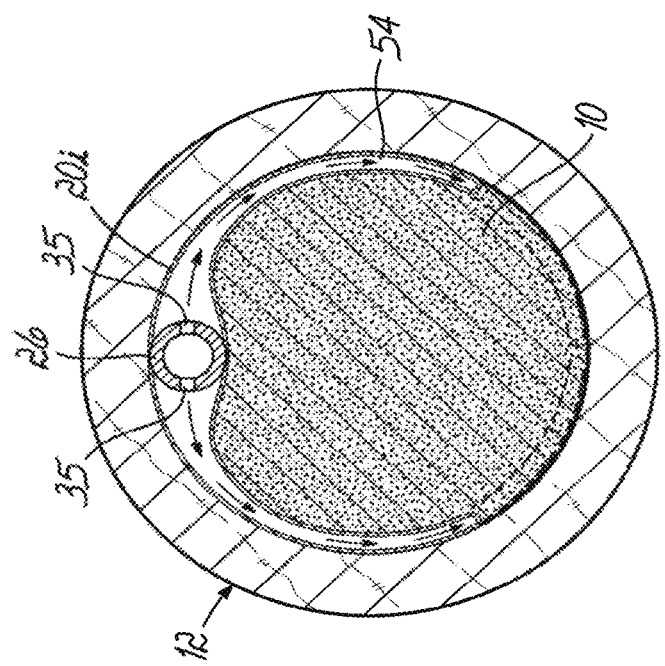
FIG. 16E is a transverse cross-sectional view similar to FIG. 16D but illustrating deployment of the radially expandable seal.

FIGS. 16A through 16C also show a suction catheter 14 with an attached or integrated funnel-shaped seal 16 to create a seal with the vessel 12 and improve the suction to remove the clot 10. Another manner of creating this proximal seal 16 would be to use a conventional off-the-shelf cylindrical suction catheter, and then add the funnel-shaped seal 16 during the surgical intervention. This option is described more fully below. The proximal seal 16 could be attached to a long wire to advance it down the suction catheter 14. The seal 16 could be made with an expandable frame of NITINOL or other shape memory material. A membrane cover could be added to enhance the seal. The shape memory mesh itself may be adequate to seal if the mesh is dense, but the addition of a solid or fluid impervious covering may create a more robust fluid pressure seal. A distal seal membrane 20i, as shown, is collapsed against the microcatheter 26 so that it can be delivered distally beyond the clot 10 in a vessel 12 of the patient.

FIG. 16B

This figure shows fluid being infused inside the membrane 20i. The fluid fills the membrane 20i distal to the clot 10 and expands the membrane 20i against the vessel wall surface 12a—producing a seal and ensuring that the membrane 20i is fully expanded and fluid does not escape distally to any significant extent.

Once the membrane seal 20i is filled distal to the clot 10, additional fluid is introduced. The membrane 20i begins to wrap around the clot 10. This is important because the movement of the membrane 20i around the clot 10 will help to separate the clot 10 from the vessel wall surface 12a. As explained previously, separating clot 10 from the vessel wall surface 12a is very important as it frees any attachments between the clot 10 and the vessel wall surface 12a to facilitate clot removal. This improves the chance that the clot 10 can be extracted. The arrow in the figure shows the course the membrane 20i will take enveloping the clot 10.

FIG. 16C

The membrane 20i has occluded the vessel 12 distal to the clot 10. The membrane 20i is shown wrapping around the clot 10 and separating the clot 10 from the wall surface 12a at least part of the way around the vessel 12. The membrane 20i is shown open at the proximal end. The membrane 20i could actually be closed (as indicated in the figure) or partially closed at the proximal end to help ensure that it wraps around the clot 10 to the fullest extent possible before fluid begins to escape proximally.

It may also be useful to fully expand the membrane 20i and keep infusing fluid. The infused fluid can help to separate the clot 10 not contacted by the membrane 20i. As explained previously positive pressure may be applied proximal to the clot 10 from the suction catheter 14 or otherwise to radially expand the vessel 12 and help separate clot 10 from the vessel wall surface 12a. The membrane 20i that wraps around the clot 10 could be wide enough to fully wrap around the clot 10. Also, pulsing/varying/cycling positive pressure and/or suction on each side of the clot 10 may also be useful in extracting clot 10.

Another way to ensure the membrane 20i fills and occludes the distal portion of the vessel 12 would be to deliver the membrane 20i out of a microcatheter 26 so that it is only partly deployed (for example, half-way deployed). This would trap fluid and inflate the membrane 20i. After the membrane 20i is expanded, the rest of the membrane 20i could be extruded out of the microcatheter 26. The microcatheter 26 could be slowly withdrawn allowing the membrane 20i to sequentially wrap around the clot 10 as the microcatheter 26 is withdrawn. In other words, an initial amount of fluid is introduced and this fluid fills or expands the membrane 20i at the distal end of the device. The catheter 26 is then withdrawn a few millimeters and an additional amount of fluid is introduced into the area contained by the membrane 20i. The membrane 20i wraps around more clot. The process is repeated until all the clot 10 is separated from the vessel wall surface 12a.

FIG. 16D

This figure is a cross-sectional view showing initial insertion of the microcatheter 26 alongside the clot 10 and initial deployment of the annular seal membrane 20i.

FIG. 16E

Figure 16D:
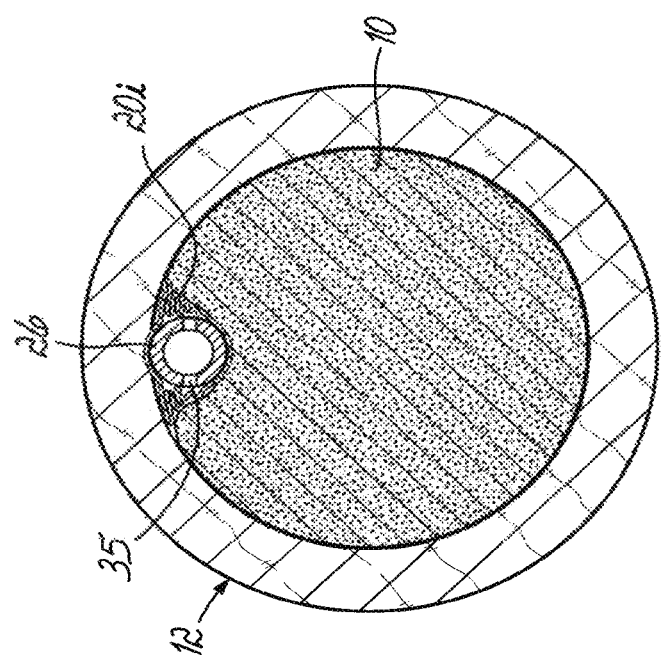
FIG. 16D is a transverse cross-sectional view showing the radially expandable seal prior to deployment.

This figure is a cross-sectional view of the membrane 20i wrapping around the clot 10 during further deployment as compared to FIG. 16D. The membrane 20i is inflated and sequentially extends around the clot 10 as more fluid is introduced. The shape of the membrane 20i can be sized so that the membrane 20i even fully envelops and wraps around the clot 10. This would separate the clot 10 circumferentially from the vessel wall surface 12a. It would also result in the clot 10 being fully enveloped by the membrane 20i. This could allow the clot 10 to be removed inside a "cocoon" like membrane enclosure that prevents the clot 10 fragmenting as it is kept in one piece for removal. The dotted lines show a variation of the membrane 20i that could fully wrap around the clot 10.

This membrane 20i is shown attached to a microcatheter 26. A guidewire type structure or other type of elongate intravascular element could instead be used to attach a membrane 20i to produce a similar device. The arrows in FIGS. 16A and 16C show suction being applied from the suction catheter 14 to remove the clot 10 once it has been freed partly or completely from the vessel wall surface 12a. Again, the funnel-shaped seal 16 proximate a distal end of the suction catheter 14 may be integral or otherwise affixed for delivery with the suction catheter 14, or it may be delivered as a separate component in which case the suction catheter 14 itself may be of a conventional type.

FIG. 16F

This shows the general shape of the membrane seal 20i. The distal end 52 is tapered. It can comprise a more pointed tip, a rounded tip or any useful shape such as a bullet type shape. At a proximal portion 54, the membrane 20i is more of a cylinder shape. Proximally, the membrane 20i might be useful to have a wider cylinder to wrap around more clot 10.

Figure 17D:
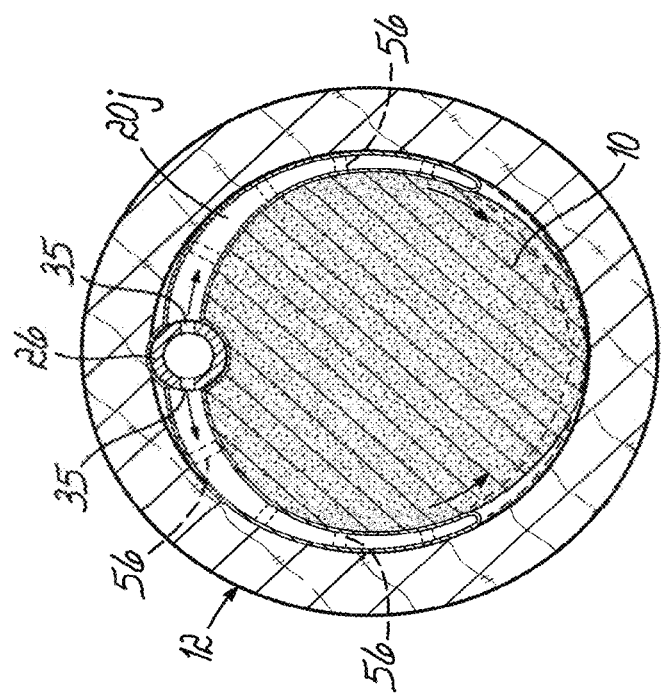
FIG. 17D is a transverse cross-sectional view similar to FIG. 17C but illustrating another embodiment of the radially expandable seal.

FIGS. 17A and 17B

These figures show a device similar to the previous arrangement. Here, a membrane 20j wraps around the clot 10 but the membrane 20j is closed at its ends. The membrane 20j that wraps around the clot 10 is coupled to or otherwise carried on a microcatheter 26, a guidewire 38 or other form of elongate intravascular element. In this regard, with respect to all embodiments the form of elongate intravascular element may take on many variations. There are openings 35 in the guidewire or catheter that communicate with the space inside the membrane 20j, so that fluid can be introduced down the catheter or guidewire to expand the membrane 20j.

In FIG. 17B, the membrane 20j has been expanded and it has wrapped around and enveloped the clot 10. The clot 10 is shown inside the membrane 20j in dashed lines. The ends of the membrane 20j are shown open. It would also be possible to have the inflated membrane 20j closed at one or both ends of the clot 10 to prevent any part of the clot 10 from escaping.

FIG. 17C

This figure shows a transverse cross section of the membrane seal 20j wrapping around the clot 10.

FIG. 17D

Figure 17C:
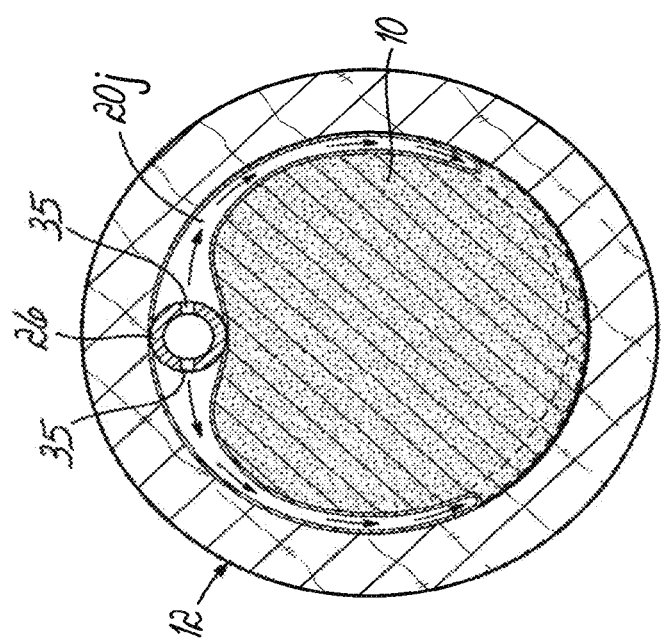
FIG. 17C is a transverse cross-sectional view showing deployment of the radially expandable seal.

In this variation of FIG. 17C, the membrane 20j has "welds" or attachments 56 that keep the membrane 20j in a flat shape as it expands. This will help to make sure the membrane 20j wraps around the clot 10 circumferentially. These attachments 56 could be point attachments or lines or circles or any useful shape to achieve this result. The figure shows the "weld points" 56 in dashed lines.

FIG. 18A

This shows a side view of a microcatheter 26 or guidewire 60 that is in a form allowing it to be inserted inside a patient. An inflatable membrane 20k has a connection to a lumen that allows the membrane 20k to be expanded once inside a patient's blood vessel (not shown).

FIG. 18B

This figure shows the membrane 20k expanded. The membrane 20k forms a closed space that can retain introduced fluid. The membrane 20k communicates with the microcatheter lumen for filling with the fluid. The figure shows weld points 62 of various shapes that keep the membrane 20k from expanding to a more spherical shape. In general this membrane 20k expands in a plane that can be used to separate the clot 10 from the vessel wall surface 12a (see other figures herein).

The weld shapes can vary to help maintain the shape of the inflated membrane 20k. It may also be useful for the membrane 20k to inflate into a cylindrical shape so that it generally inflates following the interior wall surface 12a of the vessel 12 and holds the clot 10 inside. This could be accomplished by making one side of the membrane 20k shorter than the other, or by adjusting the welds to guide the inflated structure into a cylindrical or other tubular shape. Once the clot 10 is contained inside the membrane 20k it will help prevent emboli from traveling distally and causing stroke or damage downstream in the brain. In this regard, the membrane 20k acts as a radially expandable seal.

FIG. 18C

This figure shows a cross section view of the expanded membrane 20k. Weld points 62 serve to control the expanded shape of the membrane 20k, i.e., a generally cylindrical shape for enveloping the clot 10.

FIG. 19A

This figure again shows a clot extraction device or membrane 201 that is in a collapsed state ideal for insertion inside a patient. An elongate intravascular element, such as a guidewire or a microcatheter 60, provides a channel to fill the membrane 201 with fluid. The elongate intravascular element, e.g., guidewire 60, communicates with one or more interior voids or spaces in the membrane 201 for inflating the initially closed or collapsed membrane 201.

FIG. 19B

Figure 18A:
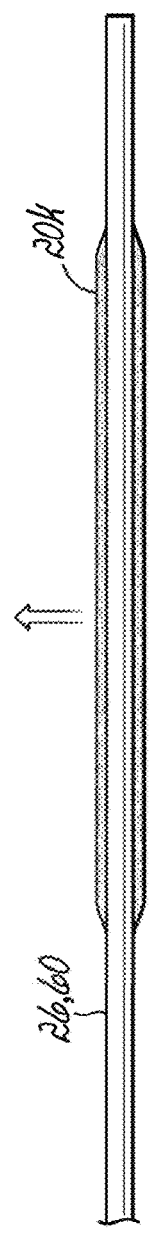
FIG. 18A is a longitudinal cross-sectional view illustrating another embodiment of an elongate intravascular element and radially expandable seal or blood clot extraction element.
Figure 18B:
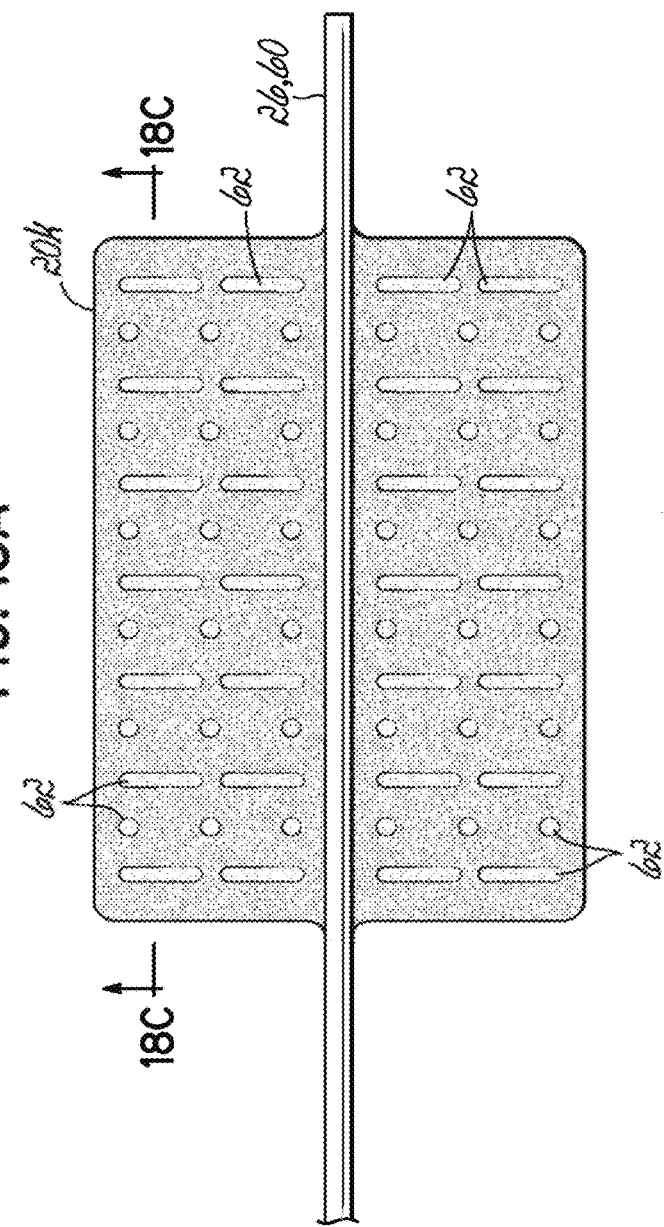
FIG. 18B is a side elevation illustrating full deployment of the radially expandable element shown in FIG. 18A.
Figure 18C:
FIG. 18C is a longitudinal cross-sectional view illustrating the radially expandable element of FIG. 18B.
Figure 21C:
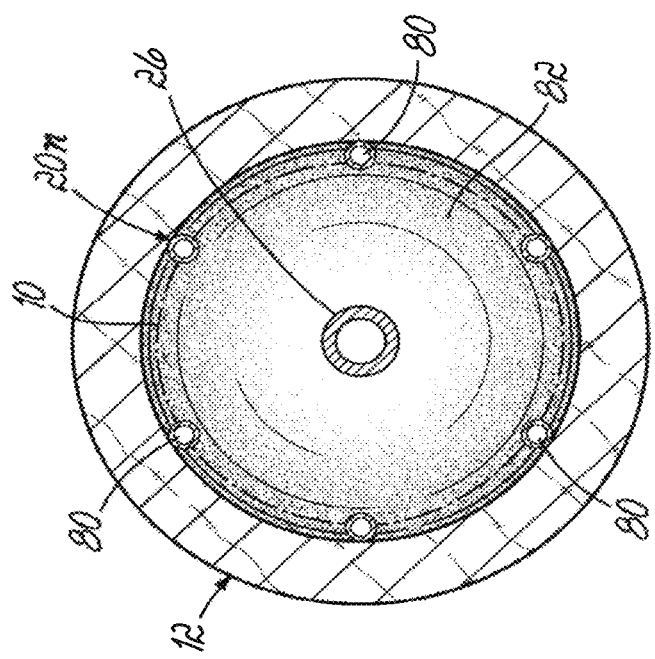
FIG. 21C is a transverse cross-sectional view of FIG. 21B showing the fully deployed blood clot dislodging and removal element.

The prior FIGS. 18A and 18B show a membrane 20k designed to wrap around clot 10. It may be difficult to collapse this extensive membrane 20k for insertion, as there is a large amount of membrane 20k to collapse. FIG. 19B shows a membrane 201 with numerous sealed cut outs separated by fluidly connected series of link elements 64 inflated from the central lumen of the guidewire or microcatheter 60. The inflatable link elements 64 may be shaped in three dimensions to form a tube or cylinder to wrap around the clot 10. The shape of pentagons and hexagons is shown here, but any shape of this type of lattice structure may be used. An advantage of the open lattice is reduced material to allow crimping for delivery.

It should be noted that this same shape of device could be constructed without needing a fluid inflation. The lattice could be constructed from a collapsible material such as NITINOL or other super-elastic material. The lattice could be crimped inside a catheter for delivery, and may self-expand into this shape once released from the catheter.

FIG. 19C

This figure shows the device inside a vessel 12, inflated and wrapping around a clot 10. The device is mounted on a combined guidewire and microcatheter 26. An attachment at the distal tip 26a of the catheter 26 to the guidewire 38 produces a seal that prevents leakage of the introduced fluid at the tip.

The microcatheter 26 is hollow and allows fluid to fill the membrane 201 that wraps around the clot 10. The membrane 201 is fluidly coupled to the lumen of the microcatheter 26 in a manner that allows fluid to fill, i.e., expand the membrane 201 generally as described herein.

The membrane 201 that wraps around the clot 10 could form an enclosure at either or both of the proximal or distal ends. This would further help keep pieces of the clot 10 from escaping.

The figure also shows an arrow showing the microcatheter 26 being withdrawn to remove the clot 10 inside the enclosed inflated membrane structure.

There is a suction catheter 14 with a funnel-shaped proximal seal 16 or mouth. The assembly 201, 26, 38 can be pulled through the suction catheter 14 if desired. The arrow shows the direction of travel of the microcatheter 26 to remove the clot 10 inside the lattice structure. Alternatively, as with all other embodiments, the clot 10 may affix itself to the distal tip or end of the suction catheter 14 and the suction catheter 14 may then be withdrawn with the attached clot 10.

FIG. 20A

This figure shows another way to remove clot 10 from a vessel 12. A suction catheter 14 with a funnel mouth 16 is shown proximal to the clot 10, and constructed such as in any of the manners described herein. The clot 10 is impacted in the vessel 12. A microcatheter tip 26a has been passed distally beyond the clot 10. This microcatheter 26 has a guidewire tip 36. The microcatheter 26 has a hollow lumen to fill a clot extraction or removal device 70 with fluid. It should be noted that the device core or spine could be constructed from a guidewire entirely, or from a microcatheter without a tip of guidewire. Inflatable structures are shown and may comprise an annular inflatable membrane 20m. The membrane 20m may entrap and/or surround the clot 10.

FIG. 20B

This figure shows the annular inflatable membrane 20m expanded. When expanded, the membrane 20m forms "fingers" 72 that wrap around the clot 10 and contain it. The fingers 72 expand toward the clot 10 and then wrap around as shown to contain the clot 10. Alternatively (not shown in the figure), the fingers 72 could be inserted and fully expanded along the length of the microcatheter spine or core, so as to then wrap around the clot 10 as they are inflated. Proximal and distal membrane portions 74, 76 could be continuous (i.e., joined proximal and distal finger segments). When inflated, the fingers 72 would completely cover and trap the clot 10 for sealing purposes. The figure shows an arrow indicating that the clot 10 is being pulled out.

FIG. 21A

This figure shows a variation on the inflatable finger structure shown in the prior figures. A clot 10 is inside a vessel 12 and a funnel-shaped seal 16 and suction catheter 14 are proximal to the clot 10 as previously described. A core or spine is shown composed of a hollow and fillable microcatheter 26 with a guidewire tip 36. Fine rods 80, composed of polymer gas fillable tubes or most likely composed of wire or also polymers like suture material (such as polypropylene), extend between inflatable bulbous ends 82, 84. At their ends, the rods 80 engage with or attach to the inflatable bulbous ends 82, 84. To help splay open the rods 80, the rods 80 may wrap over the distal end of the inflatable bulbous ends 82, 84. The rods 80 are collapsed against the spine provided by the catheter 26.

FIG. 21B

The inflatable ends 82, 84 are expanded. The rods 80 sweep around the interior perimeter of the vessel 12 and scrape the clot 10 from the vessel wall surface 12a. The inflatable ends 82, 84 may also expand the vessel wall to help the rods 80 wrap around the clot 10. The rods 80 are shown surrounding the clot 10 and trapping the clot 10 inside for extraction. The rods 80 have been moved into position by the inflation of the inflatable bulbous ends 82, 84. The inflation carries the rods 80 around the clot 10. The clot 10 can be extracted in or attached to the distal end of the suction catheter 14.

FIG. 21C

This cross-sectional view shows one of the inflatable bulbous ends 82 with a microcatheter 26 attached. The rods 80 are shown in a radially expanded position to surround the clot 10. The rods 80 may be located or wrapped over the ends 82, 84.

FIGS. 22A and 22B

This variation of a membrane 200 shows inflatable bulbous ends 86, 88 that do not wrap around the microcatheter 26. The inflatable bulbous ends 86, 88 move wires or rods 90 which can be inflatable or just composed of metal wire or polymer wire to wrap around the clot 10. There is a fluid connection between the catheter 26 and the bulbous ends 86, 88 to allow them to be filled with fluid and expanded in the positions shown to seal the vessel 12 on opposite proximal and distal ends of the clot 10.

Figure 23A:
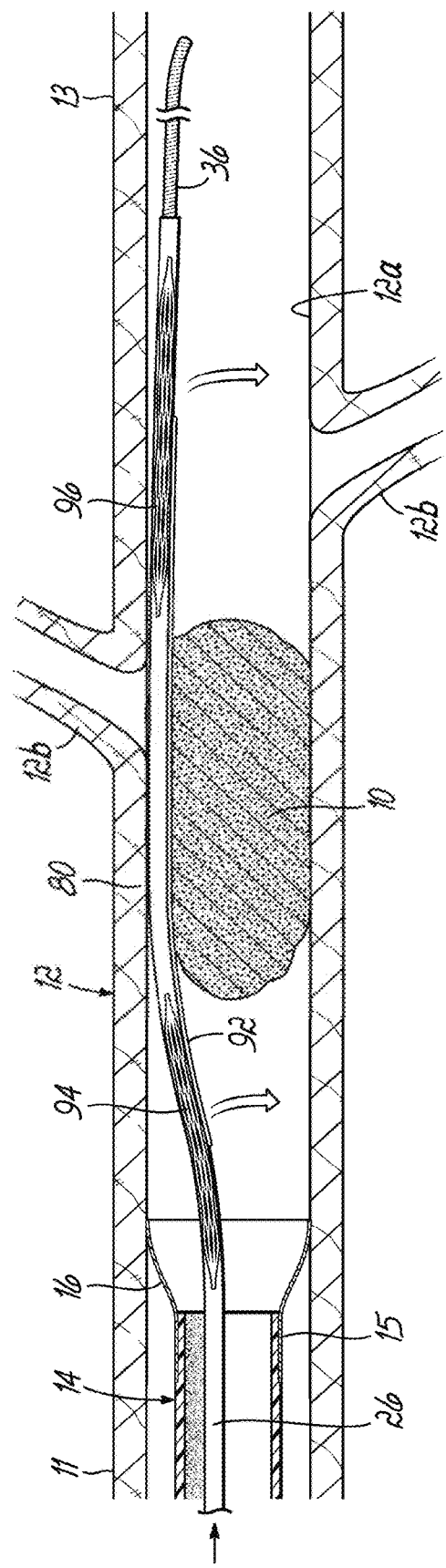
FIG. 23A is a longitudinal cross-sectional view schematically illustrating another illustrative embodiment of a blood clot removal or extraction system.
Figure 23B:
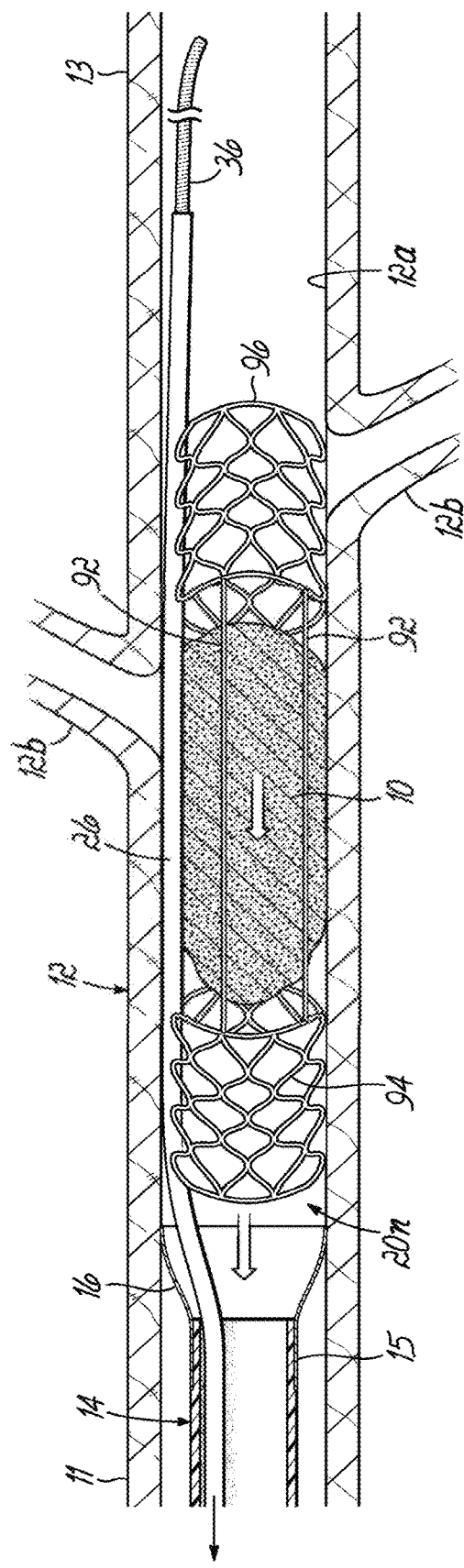
FIG. 23B is a view similar to FIG. 23A but illustrating a subsequent step in the method.

FIGS. 23A and 23B

Rods that wrap around clot 10 can be activated by means other than fluid inflation. In these figures, a clot extraction device is shown as including rods 92 that a wrap around a clot 10 are carried inside a microcatheter 26 with a guidewire tip 36. The rods 92 are attached at each end to a collapsible stent 94, 96 (with one stent at each end of the rods). The proximal and distal stents 94, 96 are collapsed inside the microcatheter 26 for insertion. The microcatheter 26 can be withdrawn allowing the stents 94, 96 to self-expand. In this regard, any of the stents or stent-like structures described herein may be of the self-expanding type. The stents 94, 96 and their attachment to the rods 92 expand and wrap the rods 92 around the clot 10. The stents 94, 96 could be made of shape memory material like NITINOL, or any other super-elastic material that automatically expand to the desired shape when released from a catheter.

This separates the clot 10 from the vessel wall surface 12a, and then the rods 92 trap the clot 10 inside. The open stents 94, 96 can also help with clot extraction. They can comprise tapered ends to allow the stent to be pulled back to remove the clot 10 easily. The stents 94, 96 could be shaped differently. Any stent variation that moves the rods 92 around the stent would be satisfactory. The microcatheter 26 could be removed once the stent is deployed. Then the stent/rod device could be pulled to remove the clot 10. Not shown in the figures is a pull wire to withdraw the trapped clot 10. Ideally, the proximal end of the proximal stent 94 has a wire (not shown) attached to its end and this wire would pass through the suction catheter 14 so that the interventionist could pull on the wire and retrieve the clot 10.

Figure 23D:
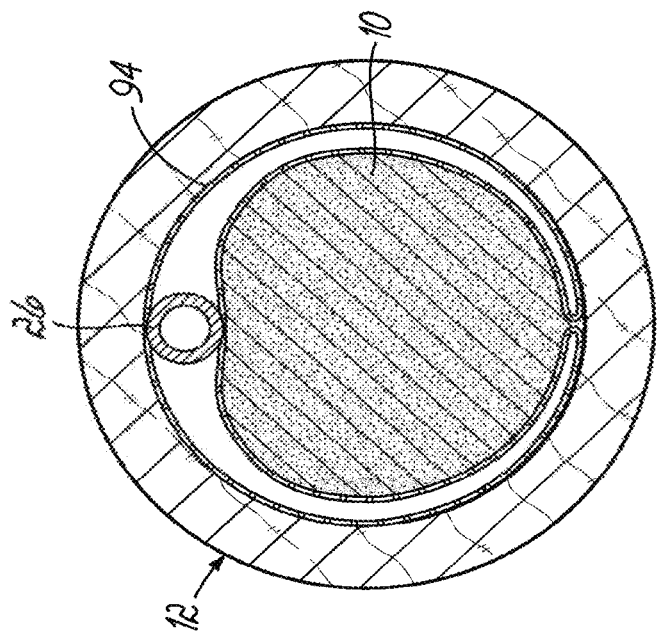
FIG. 23D is a transverse cross-sectional view similar to FIG. 23C but illustrating further deployment of the radially expandable extraction element.
Figure 23C:
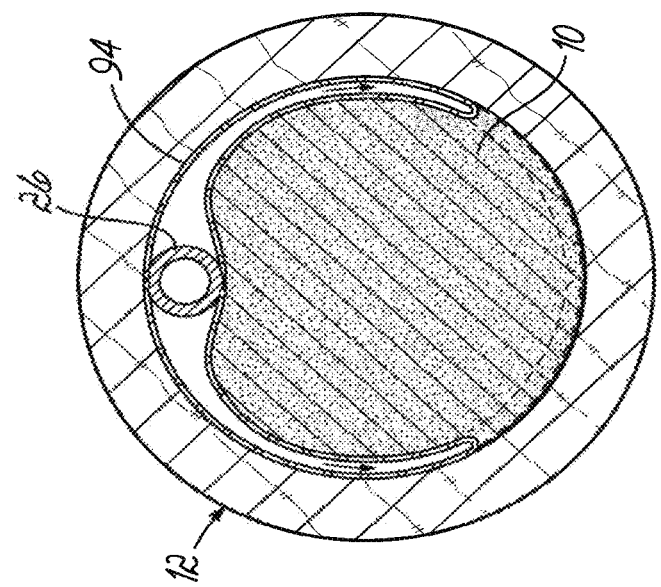
FIG. 23C is a transverse cross-sectional view showing initial deployment of the radially expandable blood clot extraction element.
Figure 26C:
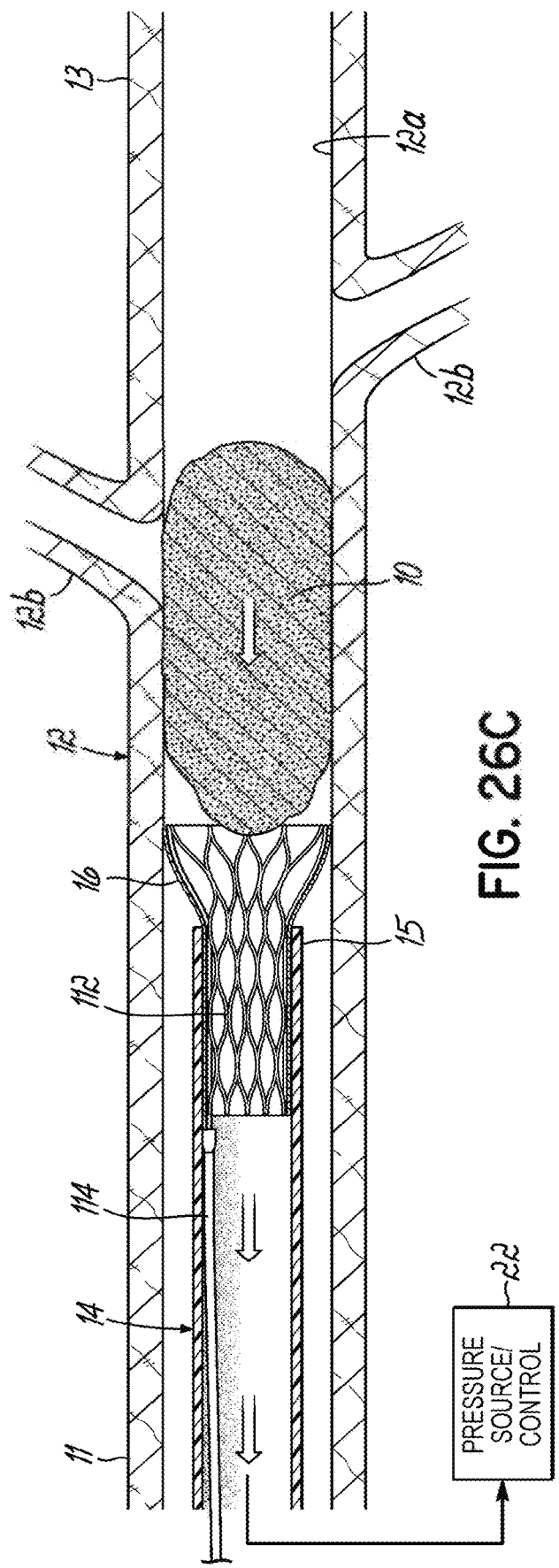
FIG. 26C is a view similar to FIG. 25B but illustrating a subsequent step in the method.

FIGS. 23C and 23D

It would be helpful for the stents 94, 96 at opposite ends of the clot 10 to expand following the inner lumen of the vessel 12 and along a curved wall of the vessel 12. Since these stents 94, 96 carry the rods 92, this will ensure the clot 10 is separated by the rods 92 from the vessel wall surface 12a and that the rods 92 will entrap the clot 10. These cross-sectional views show the stent 94 unfolding in a circumferential pattern to carry the rods 92 around the perimeter of the clot 10.

FIGS. 24A and B

Using rods (wire, polymer etc.) to wrap around a clot 10 is useful to separate clot 10 from the wall surface 12a of the vessel 12 and trap it for removal. The prior series 23 figures show a pair of expandable stents 94, 96 that carry the rods 92 so they wrap around the clot 10. FIGS. 24A and 24B show an alternative to stents or fluid inflation. This system uses two loops 100, 102—respectively located at proximal and distal positions and separated by rods or wires 104. The loops 100, 102 could self-activate as the system is released from inside a microcatheter 26 or other elongate intravascular element. The loops 100, 102 instead could be activated by a pull wire (not shown) so that the loops 100, 102 move into the active position. The loops 100, 102 could be formed from wire, such as stainless steel or from shape memory material, such as NITINOL or other super-elastic material.

In FIG. 24B, the microcatheter 26 is still in place. If the system was delivered from inside the microcatheter 26 instead of carried by the microcatheter 26, the microcatheter 26 may be removed. The loops 100, 102 perform the same or similar function as the stents 94, 96. The loops 100, 102 guide the rods 104 around the clot 10 to separate and extract the clot 10. Also shown is an optional distal membrane or seal 20, such as a bag-like component that is attached to the distal loop 102 to ensure that debris or clot material does not pass downstream from the clot 10.

FIGS. 25A and 25B

These figures show an alternative funnel-shaped distal end configuration 16 for the suction catheter 14. Instead of a stent activation, there is a wire loop or hoop 110 that flips into position and opens up the funnel mouth or proximal seal 16. The seal 16 is, in this embodiment, a separate component from the suction catheter 14 and pushed into place at the distal end of the suction catheter 14 where the wire loop 110 is activated to secure the proximal membrane or seal 16 to the distal end portion of the suction catheter 14. This progression of the seal is shown in these figures. The funnel-shaped seal 16 then performs the functions as described herein.

FIG. 26A

This figure shows a clot 10 trapped in a vessel 12. A conventional cylindrical suction catheter 14 has been advanced proximate the clot 10. If suction is applied to a standard catheter some of the suction will be lost because there is no occlusion of the vessel 12. It would be very useful to 1) seal the vessel 12 so that all the suction is applied;
 2) increase the surface area at the tip of the catheter to apply more suction force on the clot 10.

Typical suction catheters are very carefully engineered to be ultra-thin yet able to withstand suction without collapse. Also, these catheters must be maneuverable through vessels that are small and at a long distance from the operators. Interventionists become very facile manipulating these catheters and custom manufacturing a suction catheter 14 with a funnel-shaped distal end 16 may disrupt the deliverability of the suction catheter 14. Thus, adding a funnel-shaped radially expandable seal tip 16 to an existing catheter may be a better alternative.

This figure shows a collapsed tube 112, formed from a shape memory material such as NITINOL, or other suitable material, with a radially expandable seal 16 or funnel mouth and a cylindrical body. The figure shows a membrane or cover material on the funnel-shaped portion or mouth 16. This covering material is optional but it can improve the seal. A fine layer of GORE-TEX/ePTFE may be a good choice but other materials could be used such as biologic materials (pericardium) or other polymers. There is a push wire 114 attached to the stent structure 112 to allow the stent structure 112 to be inserted and removed. The stent structure or tube 112 is shown inside a catheter 116 (dotted). It may be possible to insert this device without a catheter-such as from directly inside the suction catheter 14.

FIG. 26B

The funnel tip 16 is being extruded out the end of the suction catheter 14. It is more specifically extending from a microcatheter 26. It may be possible to deliver this funnel tip 16 directly down the suction catheter 14. The funnel-shaped seal 16 forms or takes the illustrated shape in a self-expanding manner due to the preformed shape allowed by the use of shape memory material. The membrane is shown over the shape memory material stent but it could be inside the stent or it could be between the wires of the stent.

FIG. 26C

The funnel stent-like seal 16 has been fully deployed. The arrow shows suction being applied by the suction catheter 14. The funnel mouth 16 has formed a seal by radially expanding in engagement against the interior wall surface 12a of the vessel 12. The funnel-shaped seal 16 has thereby increased the suction surface area to allow greater pull force on the clot 10. The funnel-shaped seal 16 may also stretch the vessel wall slightly during this step to help separate clot 10 from the vessel wall surface 12a. The funnel-shaped seal 16 could be withdrawn inside the suction catheter 14. Or the funnel tip 16 could be left in place inside the suction catheter 14 and the entire catheter system withdrawn together.

The distal end of the funnel-shaped seal 16 is shown flat, e.g., perpendicular to a lengthwise axis of the catheter 14. The distal end of the seal 16 could instead comprise any other desired shape, such as flat but angled relative to the perpendicular direction, and/or including any other shapes or distal end configurations. For example, there may be one or more indentations on the distal end, such as one or more U-shaped indentations. Such a shape may allow the distal end to better wrap around or otherwise make engagement between the clot 10 and the vessel wall surface 12a. One or more U-shaped or other suitably shaped indentations or recesses that open in a distal direction could allow at least part of the funnel-shaped seal 16 to separate clot 10 from the wall surface 12a while another part of the clot 10 would sit inside the seal 16.

Figure 27A:
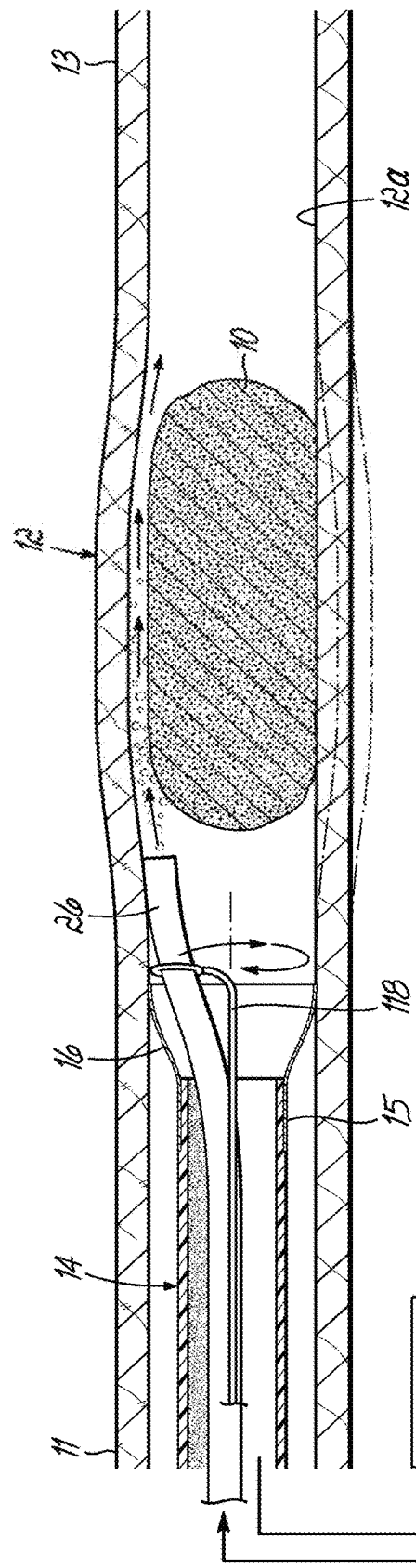
FIG. 27A is a longitudinal cross-sectional view schematically illustrating another embodiment of an elongate intravascular element being used to extract and remove a blood clot.
Figure 27B:
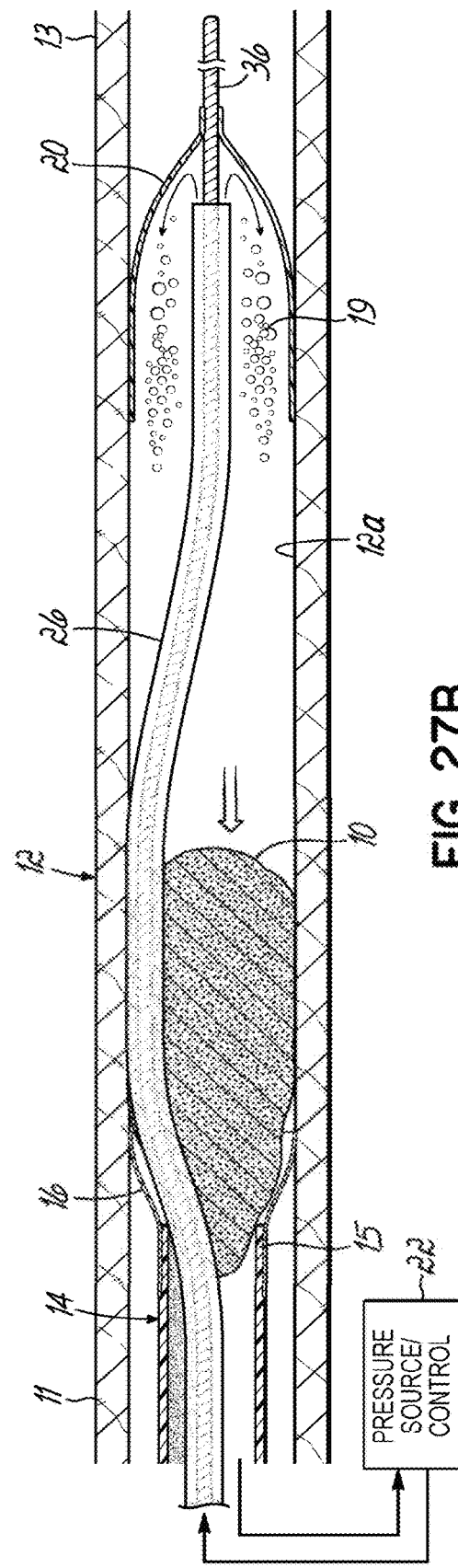
FIG. 27B is a view similar to FIG. 27A but illustrating a subsequent step in the method.

FIGS. 27A and 27B

These figures show the use of positive pressure (e.g., injection of fluid) between the clot 10 and the vessel wall surface 12a to separate the clot 10 from the vessel wall surface 12a. This positive pressure is directed through a microcatheter 26. Then, the positive pressure catheter 26 may be extended beyond the clot 10, as shown in FIG. 27B and a distal funnel-shaped or tubular seal 20 is deployed. Further positive pressure and/or suction applied proximal to the clot 10 causes the clot 10 to move proximally for capture and extraction. One or more physically (as opposed to fluidically) operating tools may be used to help with clot separation from the vessel wall surface 12a and/or extraction. One example would be to form a distal end portion (i.e., distal to the clot 10) of the positive pressure tube or catheter 26 into an S-shape or other non-linear shape that will help separate the clot 10 from the vessel wall surface 12a upon rotation and proximal movement alongside the clot 10. A wire 118 or similar element may be used to rotate the catheter 26 around the clot 10 to separate the clot 10 from the vessel wall surface 12a.

FIGS. 28A Through 28E

Figure 28A:
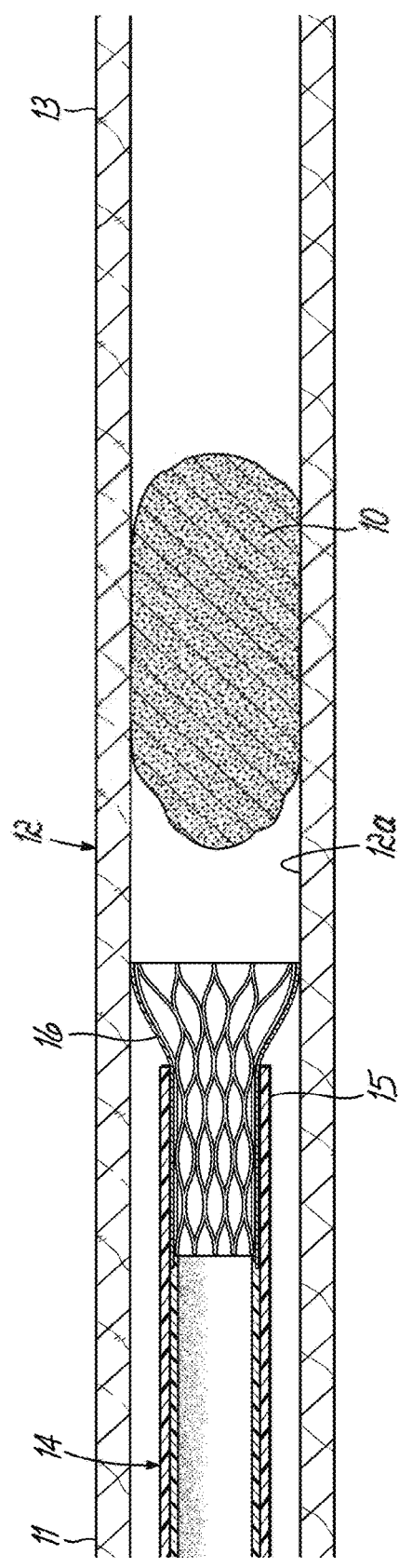
FIG. 28A is a longitudinal cross-sectional view schematically illustrating another embodiment of an elongate intravascular element being used to extract and remove a blood clot.
Figure 28B:
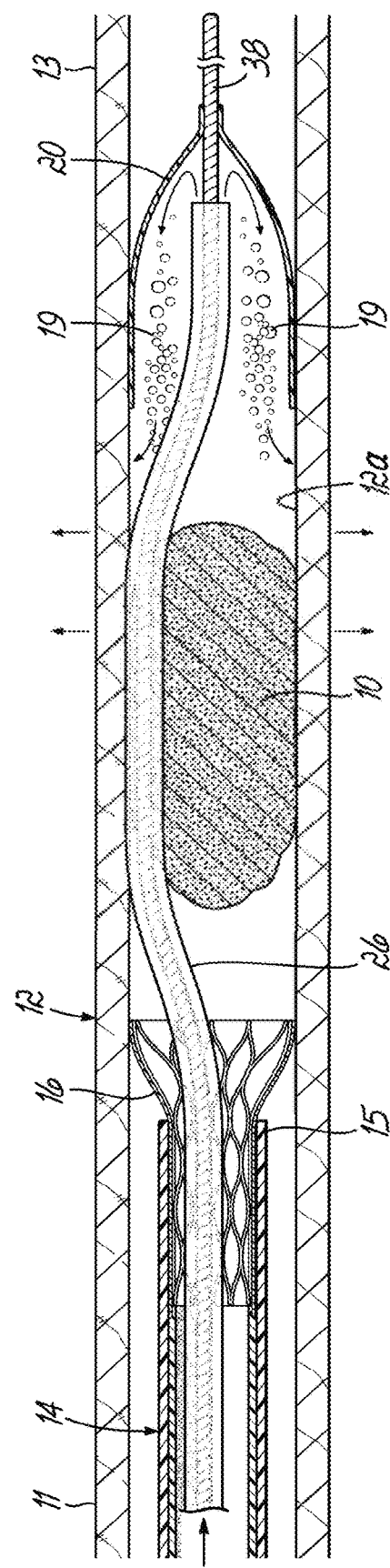
FIG. 28B is a view similar to FIG. 28A but illustrating a subsequent step in the method.
Figure 28E:
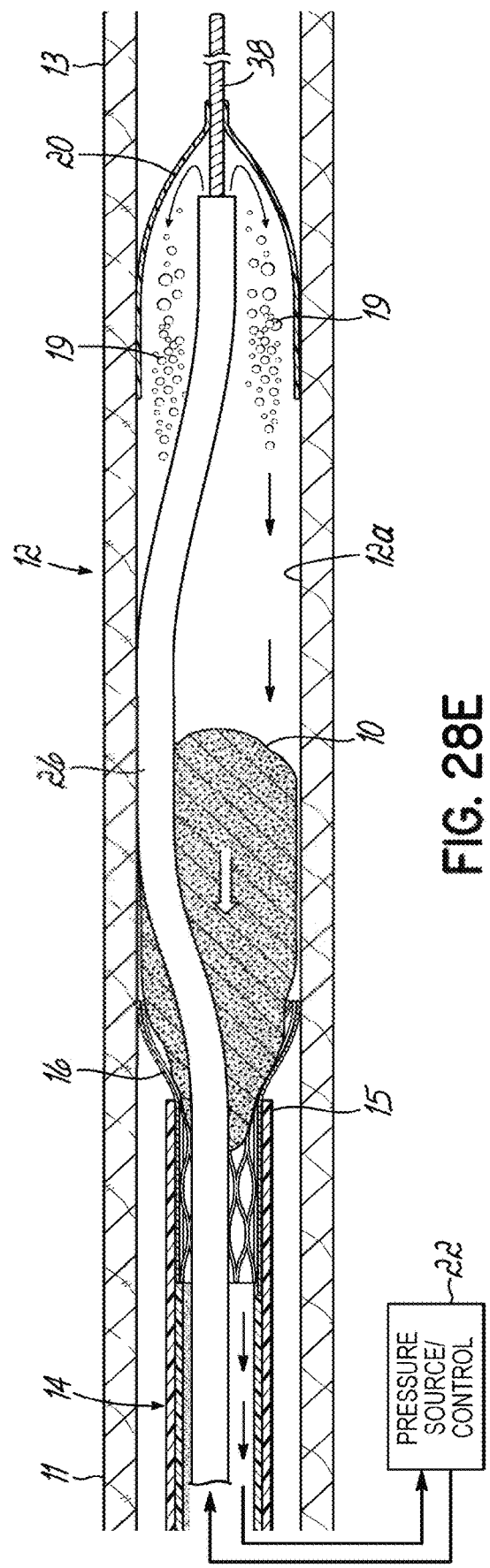
FIG. 28E is a view similar to FIG. 28D but illustrating a subsequent step in the method.

These figures show an illustrative method for removing a blood clot 10. As shown in FIG. 28A, a suction catheter 14 is passed into the venous system of the patient to the site of the blood clot 10 as shown. The suction catheter 14 either includes a radially expandable seal 16 at its distal end, as shown, such as by having the seal 16 affixed thereto or integrally formed therewith, or the seal 16 is passed separately through the catheter and fixed in place, such as in a manner previously described or another suitable manner. As shown in FIG. 28B, a distal seal 20 is passed to a distal side of the clot 10 and pressurized with a fluid, as shown, such that the seal 20 radially expands and self-adjusts to seal against the interior wall surface 12a of the vessel 12. The positive fluid pressure is then directed by the microcatheter 26 in a proximal direction push against the clot 10 and also radially expands or dilates the vessel 12 to stretch the vessel wall away from the clot 10. See, FIGS. 28B, 28C, and 28D. For example, the clot 10 may be 7 mm long and 2.5 mm wide and it may be lodged in a vessel 2.5 mm wide. The vessel 12 should stretch to 3.0-3.5 mm wide and could separate the clot 10 from the vessel interior wall surface 12a most of the circumferential way. As shown in FIG. 28E, the clot 10 may be removed proximally with suction, combined with positive fluid pressure, as necessary or desired. As with all embodiments, the fluid suction and pressure may be constant, varied (cycled or pulsed), or both, depending on the needs of the case.

Figure 29C:
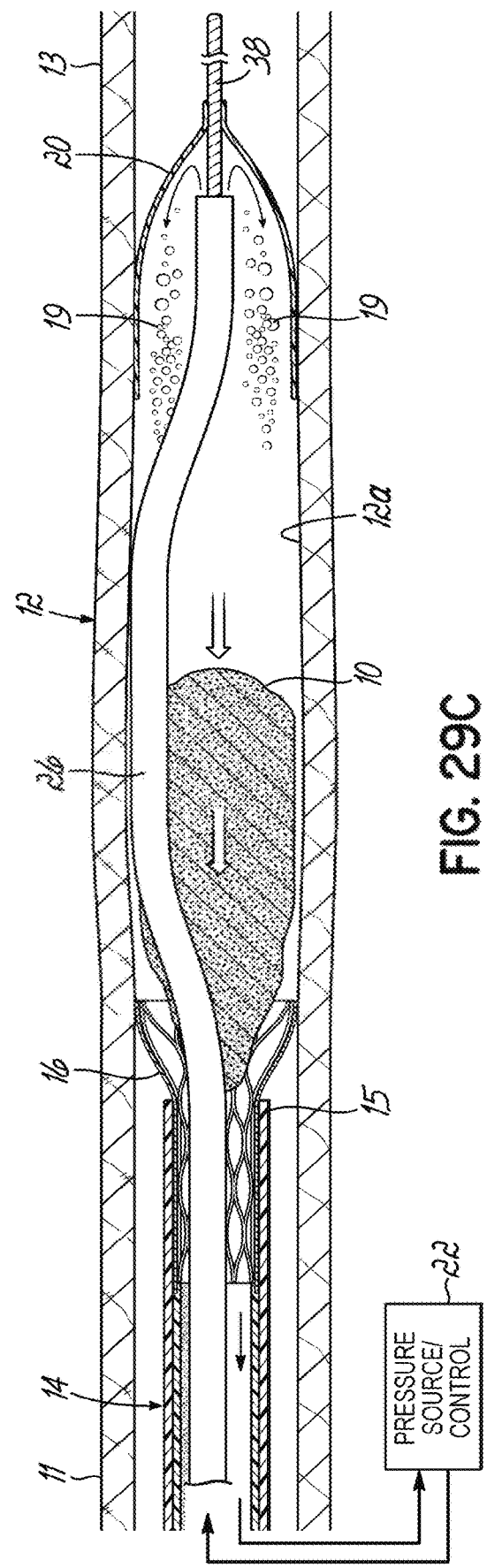
FIG. 29C is a view similar to FIG. 29B but illustrating a subsequent step in the method.

FIGS. 29A, 29B and 29C

These figures show an illustrative method for removing a blood clot 10 that is similar to that shown in FIGS. 28A-28E, except that a mechanical clot dislodging device 120 is further used to help separate the clot 10 from the vessel interior wall surface 12a. As shown in FIG. 29A, a suction catheter 14 is passed into the venous system of the patient to the site of the blood clot 10 as shown. The suction catheter 14 may be constructed in one of the manners described above in connection with FIG. 28A, or in any other suitable manner. As shown in FIGS. 29A-C, a distal seal 20 is passed to a distal side of the clot 10 and pressurized with a fluid, as shown, such that the 20 radially expands and self-adjusts to seal against the interior wall surface 12a of the vessel 12. The positive fluid pressure is then directed proximally against the clot 10 and also radially expands or dilates the vessel 12 to stretch the vessel wall away from the clot 10 generally as described above in connection with the FIG. 28 series. For further assisting with separation of the clot 10 from the interior wall surface 12a, a circular or partially circular tipped element, such as a wire 120, is passed back and forth along a periphery of the clot 10 as shown in FIGS. 29A and 29B, preferably while suction and/or positive fluid pressure continues to be applied as illustrated. The curved wire or element 120 may have a radius of curvature greater than the internal radius of curvature of the vessel 12 to ensure that the wire or element 120 bears against the interior wall surface 12a slightly, and without damaging the vessel 12. As shown in FIG. 29C, the clot 10 may be removed proximally with suction, combined with positive fluid pressure, as necessary or desired.

Figure 30A:
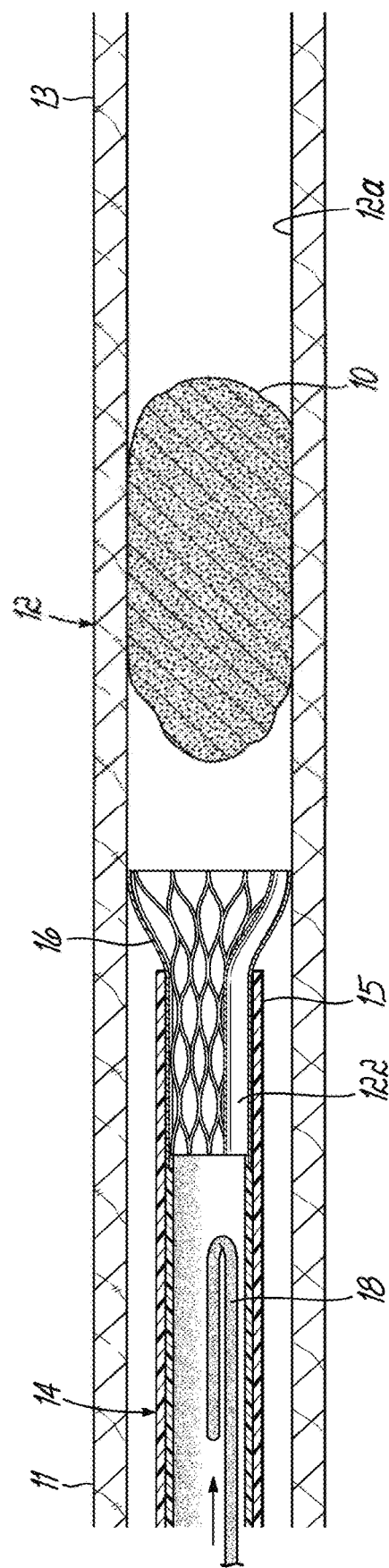
FIG. 30A is a longitudinal cross-sectional view schematically illustrating another embodiment of an elongate intravascular element being used to extract and remove a blood clot.
Figure 30B:
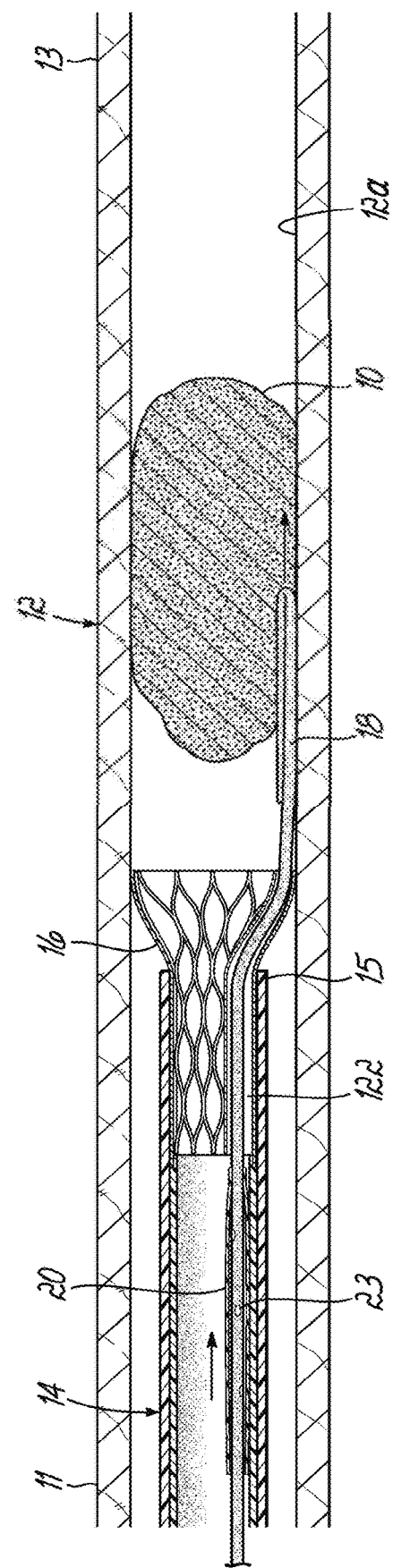
FIG. 30B is a view similar to FIG. 30A but illustrating a subsequent step in the method.
Figure 30C:
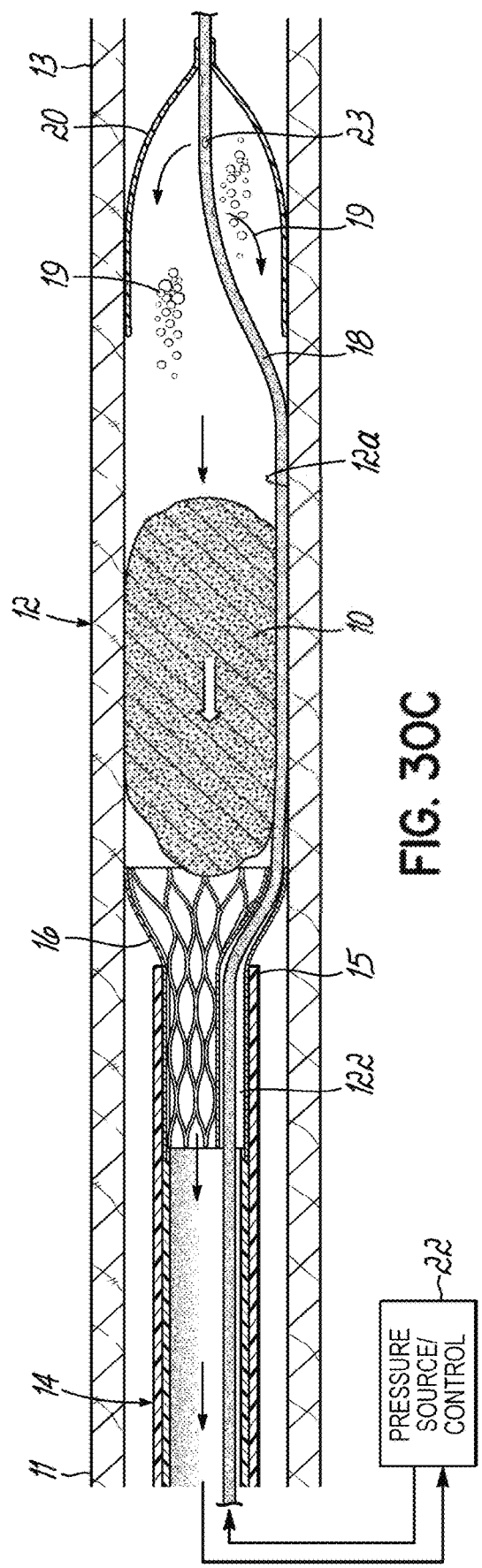
FIG. 30C is a view similar to FIG. 30B but illustrating a subsequent step in the method.

FIGS. 30A, 30B and 30C

This series of figures is similar to the series of FIGS. 28 and 29, and repeated description is therefore unnecessary in regard to common steps that may be undertaken, consistent with the illustrations. The difference in FIGS. 30A-30C is that a guide 122 has been provided on the suction catheter 14. This guide 122 may be provided on any other component used in the method, instead, and the location of the guide 122 on the suction catheter 14 is therefore just one example. The guide 122 comprises a channel provided at the distal end of the catheter 14 and, more specifically, in the radially expanded element or seal 16. This guide 122 receives the elongate intravascular element in a manner that directs the distal end of the element 18 in a sideward direction toward a periphery of the blood clot 10. The distal end of the guidewire 18 ideally passes generally between the periphery of the clot 10 and the interior wall surface 12a of the vessel 12 and exits on the distal side of the clot 10, with the radially expandable seal 16 ready for deployment. The radially expandable seal 16 is then deployed in one of the manners previously described, as examples. The elongate intravascular element or guidewire 18 may then be used to inject positively pressurized fluid in a manner and for purposes previously described, or the element may instead be used as a component to capture emboli released from the clot 10 during the method of removal.

The description herein shows and describes clot removal devices that take advantage of pressure generated by a gas and/or other fluid such as a liquid. The gas could be air or any other useful gas. Helium is used in medical applications because of its low density and because it is easy to infuse in small catheters where the channel for infusion is small and long. The intra-aortic balloon pump uses this gas which can be shuttled very rapidly in and out of the balloon inside a patient due to its low viscosity. A mixture of gases such as $CO_2$ and Helium may be useful to maximize the absorption by tissue ($CO_2$) and improve injectability (Helium).

A fluid such as saline or a dye can also be injected distal to the clot 10 to pressurize the membrane seals shown and described herein.

In one alternative method of operating the devices, positive fluid pressure may be applied only distally beyond the clot 10. The positive fluid pressure may be pulsed or oscillated distally beyond the clot 10 or the pressure may be generally constant, or a combination of pulsed/oscillated fluid pressure and constant pressure may be used, as desired by the physician.

The clot 10 may become adherent to the intimal (interior) wall surface 12a of the blood vessel 12. A positive fluid pressure can be applied proximal to the clot 10 to help stretch the vessel 12 and/or otherwise to free the clot 10. Combined positive pressure proximal and distal to the clot 10 can potentially help free the clot 10 from the vessel wall surface 12a to help with extraction. Clot 10 that is inside an artery becomes quite adherent to the vessel wall surface 12a in a short time. It may be useful to oscillate/pulse/cycle the pressures distal and proximal to the clot 10 to loosen it for extraction. Or, suction applied proximal to the clot 10 can be alternated with cycled/pulsed positive fluid pressure distally to free and remove clots. Suction can also be used proximal to the clot 10 to remove the clot 10. The suction can be oscillated/pulsed/cycled or constant depending on the combination of features used in accordance with this disclosure.

A combination of proximal and distal pressure manipulations (positive and negative, as well as oscillations in pressure) may indeed improve clot removal. Pressure can be constant or oscillated on each side of the clot 10 to help dislodge the clot 10.

A control unit 22 can also be added to the system to control the pressures proximal to the clot 10 and the positive pressure distally beyond the clot 10. This control unit 22 may consist of pumps and vacuums that can be used to deliver the ideal pressures and pressure fluctuations.

It may also be useful to have gas or other fluid(s) positively infused around the clot 10. Holes in the pressure inflation catheter that is passed distally beyond the clot 10 may also include holes adjacent or proximate the clot 10 to impact the clot 10. This may help to separate the clot 10 from the vessel wall surface 12a and help with clot removal. When removing a clot surgically, the surgeon has spatula-shaped tools to separate clot from the vessel wall. Gas infusion or other fluid infusion around the clot 10 may be advantageous for similar effect without similar risk of vessel damage.

To maintain ideal clot removal conditions, it may be useful to add pressure sensors to the control 22. These sensors can be inside a control unit or attached to or included in the clot suction catheter 14 and the catheter that is placed distally beyond the clot 10. Small micro-transducers can be added to the catheters at useful locations to help monitor the pressure inside the patient. A high pressure may lead to a vessel rupture. Too low a pressure may not provide adequate force to remove the clot 10. Certain pressure levels may indicate a clot 10 has plugged the suction catheter 14 or that the clot 10 is traveling proximally through the suction catheter 14 during removal.

As described previously, $CO_2$ is a good imaging agent in radiology. When $CO_2$ is infused it provides a negative image as opposed to dyes (which typically contain iodine) which are positive images. The length of the clot 10 is often unknown because the dye stops at the clot 10. By passing a catheter distally beyond the clot 10 and infusing $CO_2$ beyond the clot 10, the distal side of the clot 10 can be imaged. This combination of imaging with dye on one side of the clot 10 (proximal) and $CO_2$ on the other side of the clot 10 (distal) may provide useful information on the length of the clot 10. This can help to position the catheters and devices to optimize removal of the clot 10.

The table below contains a number of features shown and/or described herein. Combinations of inventive systems, devices and methods may be assembled by using at least one of the features listed in the table and/or by combining two or more features from the table. Note, "RES" refers to "radially expandable seal" such as the wide variety of proximal and distal membranes or seals shown and described herein. "EIE" refers to "elongate intravascular element" such as the suction catheter 14, guidewire 18, microcatheter 26 or other EIEs contemplated herein.

A non-limiting table of features in accordance with some embodiments of this disclosure is provided below. Some of the features relate to non-structural items such as suction and/or positive pressure delivery and control. These features are discussed throughout the present specification with regard to most embodiments. For example, some embodiments will include only suction pressure on the proximal side of the clot 10. As one option, the structure in FIG. 1C may be used without the positive pressure supplied through guidewire 18, but still using suction through catheter 14. In this case, the distal seal 20 would be used as an emboli capturing element to trap emboli before they travel farther downstream into the brain. Other combinations of one or more pressure options from column 1 may be utilized to beneficial effect depending on the case. As also discussed throughout the specification, the user may choose from a variety of fluid options to deliver positive pressure proximate the clot 10. Some options are listed in column 2 and may be used alone or in combination to the desired effect by the user. Distal RES options are listed in column 3 and, for example, are shown and described as various forms of seals or membranes throughout the specification. One or more distal seals, again, may or may not be combined with other features listed in the table. Proximal RES options are listed in column 4 and, for example, are shown and described as various forms of seal 16 throughout the specification. One or more of these proximal seals configurations 16, again, may or may not be combined with other features listed in the table. Column 5 lists options for devices or components specially configured to assist with clot dislodgement and removal. For example, some specific examples are shown and described with respect to FIGS. 12B, 12C, 12D, and through 8C and 30A through 30C. Column 7 lists various control options that may be used alone or in combination with each other and with one or more of the other features/options listed in the table. In accordance with the inventive concepts, the features in any given column (1-7) below may be utilized alone or in combination, or a feature or multiple features from two or more columns may be utilized in combination to dislodge and remove a clot 10.

|   | 1 Pressure Options | 2 Fluid Options | 3 Distal RES Options | 4 Proximal RES Options | 5 Clot Dislodge/ Removal Options | 6 Guide Options | 7 Control Options |
|---|---|---|---|---|---|---|---|
| A | Constant Suction Proximal | Air | Fluid Pressure Seal | Funnel shaped | Inflatable - wrap around clot | Mechanical and non-inflatable - guide EIE to clot periphery | Level of Suction Pressure |
| B | Constant Positive Proximal | Carbon dioxide | Emboli Capture Device | Direct attachment to catheter | Mechanical elements, e.g., wire(s) extend around clot | Inflatable - guide EIE to clot periphery | Level of Positive Pressure |
| C | Cycled Suction Proximal | Nitric Oxide | Carried on a catheter | Separable from catheter | Spiral or helical element extends around clot | Channel receives and guides EIE to clot periphery | Frequency of Cycled Suction |
| D | Constant Positive Proximal | Drugs (e.g. vasodilate or blood thinner) | Carried on a wire | Membrane material - imperforate | Stent-like structure extends around clot | Rails receive and guide EIE to clot periphery | Frequency of Cycled Positive Pressure |
| E | Cycled Positive Distal | Oxygen | Tube-shaped | Perforated construction - e.g., stent-like, mesh | Element, such as wire moved axially along clot | Combine above features as desired | Amplitude of Cycled Suction |
| F | Combine above features as desired | Saline | Beveled proximal end (straight or curved) | Self-adjusting seal diameter | Combine above features as desired | | Amplitude of Cycled Positive Pressure |
| G | | Combine above features as desired | Unrolling tube | Combine above features as desired | | | Measure blood loss from patient |
| H | | | Multiple section tube | | | | Measure suction pressure for clot status |
| I | | | Combine above features as desired | | | | Provide vibration to the clot via EIE or other component |
| J | | | | | | | Combine above features as desired |

Figure series 16 through 24 where several configurations for a distal membrane 20 are shown and described. Column 6 lists various options for guiding an EIE, such as a guidewire 18 or microcatheter 26 into position near the periphery of a clot 10 such that it may be directed past the clot 10 adjacent to the vessel wall surface 12*a*. Specific examples are shown and described in connection with FIGS. 7A through 7F, 8A

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative product and method and illustrative examples shown and described. Accordingly, departures may be made from such details without departing from the scope of the general inventive concept. For example, any of the individual features or aspects described herein may be utilized alone or together in any combination depending on the desired results and attendant advantages.

The invention claimed is:

1. A system for imaging a blood clot within a blood vessel, the system comprising:
an elongate body having a radially expandable distal seal configured to be introduced into the blood vessel and beyond the blood clot such that the distal seal is disposed distal to the blood clot, the distal seal defining an opening at a proximal portion thereof and being a membrane, the elongate body defining a lumen and at least one perforation located distal to a proximal end of the distal seal and proximal to a distal end of the distal seal, the distal seal being configured to expand by introduction of a fluid imaging agent through the at least one perforation while simultaneously expelling a portion of the fluid imaging agent through the opening to enable imaging of the blood clot; and
a fluid delivery apparatus configured to deliver the fluid imaging agent through the lumen and the at least one perforation in the elongate body into an area between the blood clot and the distal end of the distal seal to increase a pressure within the area to expand the distal seal to form a fluid pressure seal against an interior wall surface of the blood vessel distal to the blood clot, the imaging agent being viewable via an imaging modality when the imaging agent is disposed within the area such that at least a portion of the blood clot within the blood vessel can be identified.

2. The system of claim 1, wherein the imaging agent includes a radiopaque dye and the imaging modality includes fluoroscopy.

3. The system of claim 1, wherein the imaging agent is viewable via fluoroscopic imaging when the imaging agent is disposed within the area such that a distal end of the blood clot and the blood vessel distal to the blood clot can be identified.

4. The system of claim 1, wherein the position of the elongate body and the position of the distal seal are adjustable based on the identification of the portion of the blood clot within the blood vessel.

5. The system of claim 1, further comprising a catheter configured to be introduced into the blood vessel proximal to the blood clot, the elongate body being slidably disposable within a lumen of the catheter.

6. The system of claim 5, wherein the catheter is configured to apply a suction fluid pressure proximal to the blood clot to urge the blood clot proximally towards the catheter within the blood vessel.

7. The system of claim 6, further comprising a control operatively coupled with the fluid delivery apparatus to repeatedly cycle the suction fluid pressure between different pressure levels proximal to the blood clot for assisting with dislodgement and removal of the blood clot.

8. The system of claim 1, wherein the distal seal defines one or more holes at its proximal end.

9. The system of claim 1, wherein the distal end of the distal seal and a portion of a circumference of the proximal end of the distal seal are attached to the elongate body.

10. The system of claim 1, wherein the imaging agent is a radiopaque dye, and the fluid delivery apparatus is configured to deliver the radiopaque dye through the at least one perforation generating sufficient pressure to move the blood clot proximally within the blood vessel.

11. The system of claim 1, further comprising a wire mesh stent-triever coupled to the elongate body proximal to the radially expandable distal seal and configured to be disposed at least partially distal to the blood clot and to trap the blood clot and facilitate its removal from the blood vessel.

12. The system of claim 1, wherein the radially expandable distal seal is configured to automatically collapse upon stoppage of introduction of the fluid imaging agent through the at least one perforation.

13. The system of claim 1, wherein the membrane is highly flexible and the radially expandable distal seal is configured to self-adjust to seal against the interior wall surface of the blood vessel.

14. The system of claim 1, wherein the imaging agent is viewable by the imaging modality when the imaging agent is disposed within the area while the distal seal is expanding.

15. A system for imaging a blood clot within a blood vessel, the system comprising:
an elongate body having a radially expandable distal seal configured to be introduced into the blood vessel and beyond the blood clot such that the distal seal is disposed distal to the blood clot, the elongate body defining a lumen, a first perforation disposed between a proximal end of the distal seal and a distal end of the distal seal, and a second perforation disposed proximal to the proximal end of the distal seal; and
a fluid delivery apparatus configured to deliver via the lumen a fluid imaging agent through the first perforation and the second perforation into an area between the blood clot and the distal end of the distal seal and to radially pressurize the distal seal against an interior wall surface of the blood vessel distal to the blood clot, the imaging agent being viewable via fluoroscopic imaging when the imaging agent is disposed within the area such that at least a portion of the blood clot within the blood vessel can be identified.

16. The system of claim 15, wherein the imaging agent is a radiopaque dye.

17. The system of claim 15, wherein the position of the elongate body and the position of the distal seal are adjustable based on the identification of the portion of the blood clot within the blood vessel.

18. The system of claim 15, wherein the distal seal is a membrane.

19. The system of claim 15, wherein the imaging agent is a radiopaque dye, and the fluid delivery apparatus is configured to deliver the radiopaque dye through at least one of the first perforation and the second perforation, generating sufficient pressure to move the blood clot proximally within the blood vessel.

20. The system of claim 15, further comprising a catheter configured to apply suction proximal to the blood clot to urge the blood clot proximally towards the catheter within the blood vessel.

21. The system of claim 20, the elongate body being slidably disposable within a lumen of the catheter.

22. The system of claim 20, further comprising a control operatively coupled with the fluid delivery apparatus to repeatedly cycle the suction fluid pressure between different pressure levels proximal to the blood clot for assisting with dislodgement and removal of the blood clot.

23. The system of 15, wherein the elongate body is configured for the fluid delivery apparatus to deliver the fluid imaging agent concurrently through the first perforation and the second perforation.

24. The system of claim 15, further comprising a wire mesh stent-triever coupled to the elongate body proximal to the radially expandable distal seal and configured to be disposed at least partially distal to the blood clot and to trap the blood clot and facilitate its removal from the blood vessel.

25. The system of claim 15, wherein the distal end of the distal seal and a portion of a circumference of the proximal end of the distal seal are attached to the elongate body.

26. The system of claim 15, wherein the distal seal defines one or more holes at its proximal end.

27. The system of claim 15, wherein the expandable distal seal is configured to automatically collapse upon completion of a procedure for imaging a blood clot in response to stoppage of introduction of the imaging through the first perforation.

28. The system of claim 15, wherein the expandable distal seal is formed of a membrane that is highly flexible and is configured to self-adjust to seal against the interior wall surface of the blood vessel.

* * * * *